United States Patent [19]

Kawamura et al.

[11] Patent Number: 5,518,994

[45] Date of Patent: May 21, 1996

[54] 2-ARYLAMINOPYRIMIDINONE DERIVATIVE, AND HERBICIDE AND PLANT GROWTH REGULATOR

[75] Inventors: Yasuo Kawamura; Jun Satow, both of Chiba; Kenzo Fukuda, Yamaguchi; Eiichi Oya, Chiba; Kaoru Itoh, Chiba; Hiroshi Kita, Chiba; Hisashi Nakata, Chiba; Tsutomu Nawamaki, Saitama; Seiichi Fujii, Saitama; Shigeomi Watanabe, Saitama; Kimihiro Ishikawa, Saitama; Yoichi Ito, Saitama, all of Japan

[73] Assignee: Nissan Chemical Industries, Ltd., Tokyo, Japan

[21] Appl. No.: 318,680

[22] PCT Filed: Apr. 13, 1993

[86] PCT No.: PCT/JP93/00482

§ 371 Date: Dec. 6, 1994

§ 102(e) Date: Dec. 6, 1994

[87] PCT Pub. No.: WO93/21162

PCT Pub. Date: Oct. 28, 1993

[30] Foreign Application Priority Data

Apr. 15, 1992 [JP] Japan ..................... 4-095441
Aug. 21, 1992 [JP] Japan ..................... 4-222657
Dec. 3, 1992 [JP] Japan ..................... 4-324141
Mar. 19, 1993 [JP] Japan ..................... 5-060336

[51] Int. Cl.⁶ .................... C07D 239/36; C07D 239/40; C07D 401/12; A01N 43/54
[52] U.S. Cl. .................. 504/242; 504/243; 544/320; 544/321; 544/323; 544/324; 544/330; 544/331; 544/332

[58] Field of Search .................... 504/242, 243; 544/320, 321, 323, 324, 330, 331, 332

[56] References Cited

FOREIGN PATENT DOCUMENTS

| 59-106472 | 8/1984 | Japan. |
|---|---|---|
| 3-127780 | 5/1991 | Japan. |
| 4-21680 | 1/1992 | Japan. |
| 20130214 | 5/1984 | United Kingdom. |

*Primary Examiner*—John M. Ford
*Attorney, Agent, or Firm*—Foley & Lardner

[57] ABSTRACT

Disclosed are a herbicide and a plant growth regulator comprising a 2-arylaminopyrimidinone derivative represented by the formula (1):

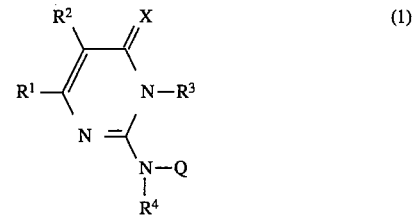

(wherein Q represents various kinds of aromatic ring or heterocyclic ring).

This compound can be used safely to main crops and shows high herbicidal effect to many weeds with a low dosage, and also shows plant growth regulating effect.

20 Claims, No Drawings

2-ARYLAMINOPYRIMIDINONE DERIVATIVE, AND HERBICIDE AND PLANT GROWTH REGULATOR

This application is a 371 of PCT/JP93/00482, filed Apr. 13, 1993.

TECHNICAL FIELD

This invention relates to a novel 2-arylaminopyrimidinone derivative, and a selective herbicide and a plant growth regulator containing said derivative as an active ingredient.

BACKGROUND ART

It is clear that accompanied with recent worldwide increase in population, productivities of important crops will influence food economy in various countries. Accompanied with these changes, a conventional agricultural system will be inevitably changed toward the 21st century. At present, development of a herbicide which can economically and efficiently kill or control weeds which are problems when crops are grown has been demanded more strongly by farm workers as compared with before.

As such a herbicide, development of a chemical which can meet the following requirements has been desired.

There have been desired a chemical having a high herbicidal effect with a small dose (it is necessary to kill weeds by. spraying a dose as small as possible particularly from the standpoint of protection of environment), a chemical having a moderate residual effect (in recent years, there has been a problem that a chemical which remains in soil for a long time causes damage to subsequent crops so that it is important to have a moderate residual effect after spraying), a chemical which can kill weeds rapidly after spraying (after treatment with a chemical, next crops can be planted or transplanted in a short period), a chemical of which the number of treatment times is small (for farm workers, it is important to reduce the number of times of cumbersome weed-controlling operation as far as possible), a chemical having weed-controlling effects on various weeds (a chemical which can control weeds having different properties such as broad-leaved weeds, grass weeds, perennial weeds, etc. by itself is desired), a chemical having many application methods (if a chemical has a soil treatment effect, a stem and foliar treatment effect, etc., a stronger herbicidal effect can be obtained) and a chemical which does not cause problematical chemical damage to crops (it is preferred to kill only weeds selectively in a cultivated field where crops and weeds coexist). However, existing herbicides cannot meet all of these requirements.

Further, in order to regulate growth of a plant by a chemical substance, there have been used conventional commercially available chemicals, for example, daminozide (general name), maleic hydrazide (general name), mefluidide (general name), etc. for the purpose of controlling growth of a plant, controlling a lateral bud, controlling growth of a lawn, etc. However, these compounds have problems that they should be used at high concentrations, their application places and application times are limited, their effects are unstable so that chemical damage is likely caused, etc.

DISCLOSURE OF THE INVENTION

In consideration of such situations, the present inventors have continued to study in order to develop a herbicide exhibiting selectivity to important crops, having excellent herbicidal effects on a large number of weeds with a small dose and having soil treatment and stem and leaf treatment effects and also in order to develop a plant growth regulator having high safety to crops and having a stable effect with a small dose, and consequently found a 2-arylaminopyrimidinone derivative (hereinafter referred to as the compound of the present invention) represented by the formula (1):

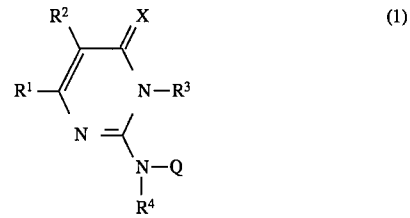

[wherein $R^1$ represents a $C_1$ to $C_4$ haloalkyl group, a $C_2$ to $C_6$ alkyl group, a $C_3$ to $C_7$ cycloalkyl group, a $C_2$ to $C_6$ alkenyl group, a $C_1$ to $C_6$ haloalkyloxy group, a $C_1$ to $C_6$ alkoxy group, a $C_3$ to $C_7$ cycloalkyloxy group, a $C_3$ to $C_6$ alkenyloxy group, a $C_1$ to $C_6$ haloalkylthio group, a $C_1$ to $C_6$ alkylthio group, a $C_3$ to $C_7$ cycloalkylthio group, a $C_3$ to $C_6$ alkenylthio group, a $C_1$ to $C_6$ haloalkylsulfinyl group, a $C_1$ to $C_6$ alkylsulfinyl group, a $C_3$ to $C_7$ cycloalkylsulfinyl group, a $C_3$ to $C_6$ alkenylsulfinyl group, a $C_1$ to $C_6$ haloalkylsulfonyl group, a $C_1$ to $C_6$ alkylsulfonyl group, a $C_3$ to $C_7$ cycloalkylsulfonyl group, a $C_3$ to $C_6$ alkenylsulfonyl group, a $C_1$ to $C_4$ alkoxy ($C_1$ to $C_4$) alkyl group, a $C_1$ to $C_4$ alkylthio ($C_1$ to $C_4$) alkyl group, a $C_1$ to $C_4$ alkoxy ($C_1$ to $C_4$) alkoxy group, a $C_1$ to $C_4$ alkylsulfinyl ($C_1$ to $C_4$) alkyl group, a $C_1$ to $C_4$ alkylsulfonyl ($C_1$ to $C_4$) alkyl group, a $C_1$ to $C_4$ alkylamino ($C_1$ to $C_4$) alkyl group, a $C_3$ to $C_7$ cycloalkyl ($C_1$ to $C_4$) alkyl group, a dimethylamino ($C_1$ to $C_4$) alkyl group, a diethylamino ($C_1$ to $C_4$) alkyl group or a halogen atom, $R^2$ represents a hydrogen atom, a halogen atom, a $C_1$ to $C_4$ alkyl group, a $C_1$ to $C_4$ haloalkyl group or a nitro group, $R^3$ represents a $C_1$ to $C_6$ alkyl group, a $C_3$ to $C_6$ alkenyl group, a $C_3$ to $C_6$ alkynyl group, a $C_3$ to $C_7$ cycloalkyl group or an amino group, $R^4$ represents a hydrogen atom, a $C_1$ to $C_6$ alkyl group, a $C_2$ to $C_6$ alkenyl group, a $C_3$ to $C_6$ alkynyl group, a $C_1$ to $C_6$ haloalkyl group, a $C_1$ to $C_4$ alkoxy ($C_1$ to $C_4$) alkyl group, a hydroxycarbonyl ($C_1$ to $C_4$) alkyl group, a $C_1$ to $C_4$ alkoxycarbonyl ($C_1$ to $C_4$) alkyl group, a formyl group, a $C_1$ to $C_4$ alkylcarbonyl group, a $C_1$ to $C_4$ alkoxycarbonyl group, an aminocarbonyl group, a $C_1$ to $C_6$ alkylaminocarbonyl group, a $C_1$ to $C_6$ alkylsulfonyl group, a dimethylaminocarbonyl group, a diethylaminocarbonyl group or a benzyl group which may be substituted, X represents an oxygen atom or a sulfur atom and Q represents a substituted phenyl ring, a naphthalene ring which may be substituted, a tetrahydronaphthalene ring which may be substituted, a benzofuran ring which may be substituted, an indane ring which may be substituted, a 2,3-dihydrobenzofuran ring which may be substituted, a methylenedioxybenzene ring which may be substituted, a 1,4-benzodioxane ring which may be substituted, a 1,3-benzodioxane ring which may be substituted, a phthalan ring which may be substituted, a phthalide ring which may be substituted, an α-coumaranone ring which may be substituted, a β-coumaranone ring which may be substituted, a 1,2-benzopyran ring which may be substituted, a 1,4-benzopyran ring which may be substituted, a chroman ring which may be substituted, a 2-chromanone ring which may be substituted, a 3-chromanone ring which may be substituted, a 4-chromanone ring which may be substituted, a coumarin ring which may be substituted, a chromone ring which may be substituted, an indene ring which may be substituted, an indenone ring which may be substituted, an α-tetralone ring which may be substituted, a 1-indanone ring which may be substituted, a 1,3-dihydroisothianaphthene ring which may be substituted or a pyridine ring which may be substituted.].

As a preferred Q, there may be mentioned the following compounds:

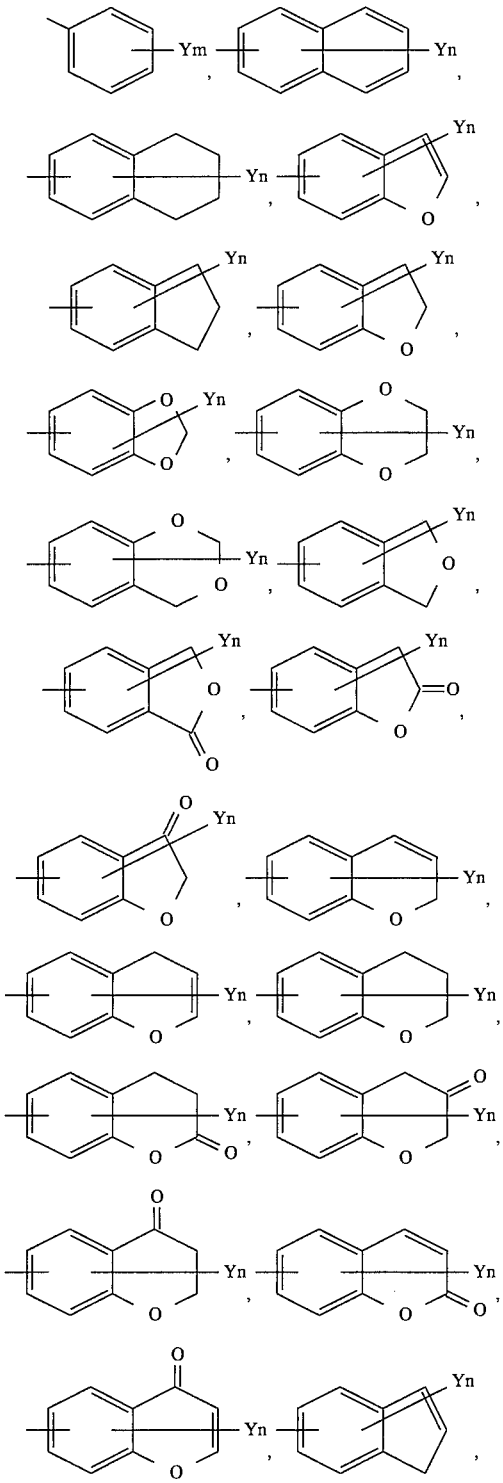

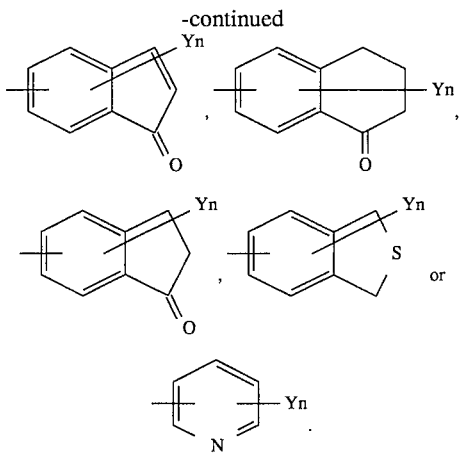

(wherein Y represents a halogen atom, a $C_1$ to $C_4$ alkyl group, a $C_1$ to $C_4$ alkoxy group, a $C_1$ to $C_4$ alkoxy ($C_1$ to $C_4$) alkyl group, a $C_1$ to $C_4$ haloalkyl group, a $C_1$ to $C_4$ haloalkoxy group, a $C_1$ to $C_4$ alkylthio group, a $C_1$ to $C_4$ alkylsulfinyl group, a $C_1$ to $C_4$ alkylsulfonyl group, a $C_1$ to $C_4$ alkylcarbonyl group, a $C_1$ to $C_4$ alkoxycarbonyl group, a $C_3$ to $C_6$ alkenyl group, a $C_3$ to $C_6$ alkenyloxy group, a $C_3$ to $C_6$ alkynyloxy group, a $C_1$ to $C_4$ alkylcarbonyloxy group, a $C_1$ to $C_4$ alkoxy ($C_1$ to $C_4$) alkoxy group, a hydroxycarbonyl ($C_1$ to $C_4$) alkyl group, a $C_1$ to $C_4$ alkoxycarbonyl ($C_1$ to $C_4$) alkyl group, a hydroxycarbonyl ($C_1$ to $C_4$) alkoxy group, a $C_1$ to $C_4$ alkoxycarbonyl ($C_1$ to $C_4$) alkoxy group, a $C_1$ to $C_4$ alkylamino group, a dimethylamino group, a diethylamino group, a $C_1$ to $C_4$ alkylcarbonylamino group, a $C_1$ to $C_4$ alkylsulfonylamino group, a thiol group, a cyano group, a carboxy group, an amino group or a hydroxy group, m represents an integer of 1 to 5, n represents an integer of 0 to 3, provided that when m is an integer of 2 to 5 or when n is 2 or 3, Ys may be the same or different).

Next, specific preferred substituents are described.

As $R^1$, there may be mentioned a trifluoromethyl group, a chlorodifluoromethyl group, a difluoromethyl group, a pentafluoroethyl group, a heptafluoro n-propyl group and a nonafluoro n-butyl group, an ethyl group, a n-propyl group, an i-propyl group, a n-butyl group, an i-butyl group, a s-butyl group, a t-butyl group, a n-pentyl group, a 1-ethylpropyl group, a 1-methylbutyl group, a 3-methylbutyl group, a 2,2-dimethylpropyl group, a 1,1-dimethylpropyl group, a n-hexyl group, a 1-methylpentyl group, a 4-methylpentyl group, a cyclopropyl group, a 1-methylcyclopropyl group, a cyclobutyl group, a cyclopentyl group, a cyclohexyl group, a 1-methylcyclohexyl group, a cycloheptyl group, a vinyl group, a 1-propenyl group, a 2-propenyl group, an i-propenyl group, a 1-butenyl group, a 2-butenyl group, a 3-butenyl group, a 1-pentenyl group, a 2-pentenyl group, a 3-pentenyl group, a 4-pentenyl group, a 1-methyl-1-butenyl group, a 3-methyl-1-butenyl group, a 1-hexenyl group, a 2-hexenyl group, a difluoromethoxy group, a trifluoromethoxy group, a 2,2,2-trifluoroethoxy group, a 2-chloroethoxy group, a 3-chloropropoxy group, a 4-chlorobutoxy group, a methoxy group, an ethoxy group, a n-propoxy group, an i-propoxy group, a n-butoxy group, an i-butoxy group, a s-butoxy group, a t-butoxy group, a n-pentyloxy group, a 2,2-dimethylpropoxy group, a n-hexyloxy group, a cyclopropoxy group, a cyclobutoxy group, a cyclopentyloxy group, a cyclohexyloxy group, a 2-propenyloxy group, a 2-methyl-2-propenyloxy group, a 2-butenyloxy group, a 2-methyl-2-butenyloxy group, a 3-methyl-2-butenyloxy group, a 2-pentenyloxy group, a 4-methyl-2-pentenyloxy group, a 2-hexenyloxy group, a difluoromethylthio group, a trifluoromethylthio group, a methylthio group, an ethylthio group, a n-propylthio group, an i-propylthio group, a n-butylthio group, an i-butylthio group, a s-butylthio group, a t-butylthio group, a n-pentylthio group, a 2,2-dimethylpropylthio group, a n-hexylthio group, a cyclopropylthio group, a cyclobutylthio group, a cyclopentylthio group, a cyclohexylthio group, a cycloheptylthio group, a 2-propenylthio group, a 2-methyl-2-propenylthio group, a 2-butenylthio group, a 2-methyl-2-butenylthio group, a 3-methyl-2-butenylthio group, a 2-pentenylthio group, a 4-methyl-2-pentenylthio group, a 2-hexenylthio group, a difluoromethylsulfinyl group, a trifluoromethylsulfinyl group, a methylsulfinyl group, an ethylsulfinyl group, a n-propylsulfinyl group, an i-propylsulfinyl group, a n-butylsulfinyl group, a i-butylsulfinyl group, a s-butylsulfinyl group, a t-butylsulfinyl group, a n-pentylsulfinyl group, a 2,2-dimethylpropylsulfinyl group, a n-hexylsulfinyl group, a cyclopropylsulfinyl group, a cyclobutylsulfinyl group, a cyclopentylsulfinyl group, a cyclohexylsulfinyl group, a cycloheptylsulfinyl group, a 2-propenylsulfinyl group, a 2-methyl-2-propenylsulfinyl group, a 2-butenylsulfinyl group, a 2-methyl-2-butenylsulfinyl group, a 3-methyl-2-butenylsulfinyl group, a 2-pentenylsulfinyl group, a 4-methyl-2-pentenylsulfinyl group, a 2-hexenylsulfinyl group, a difluoromethylsulfonyl group, a trifluoromethylsulfonyl group, a methylsulfonyl group, an ethylsulfonyl group, a n-propylsulfonyl group, an i-propylsulfonyl group, a n-butylsulfonyl group, an i-butylsulfonyl group, a s-butylsulfonyl group, a t-butylsulfonyl group, a n-pentylsulfonyl group, a 2,2-dimethylpropylsulfonyl group, a n-hexylsulfonyl group, a cyclopropylsulfonyl group, a cyclobutylsulfonyl group, a cyclopentylsulfonyl group, a cyclohexylsulfonyl group, a cycloheptylsulfonyl group, a 2-propenylsulfonyl group, a 2-methyl- 2-propenylsulfonyl group, a 2-butenylsulfonyl group, a 2-methyl-2-butenylsulfonyl group, a 3-methyl-2-butenylsulfonyl group, a 2-pentenylsulfonyl group, a 4-methyl-2-pentenylsulfonyl group, a 2-hexenylsulfonyl group, a methoxymethyl group, an ethoxymethyl group, a n-propoxymethyl group, an i-propoxymethyl group, a n-butoxymethyl group, an i-butoxymethyl group, a s-butoxymethyl group, a t-butoxymethyl group, a 2-methoxyethyl group, a 2-ethoxyethyl group, a 2-n-propoxyethyl group, a 2-i-propoxyethyl group, a 2-n-butoxyethyl group, a 2-t-butoxyethyl group, a 3-methoxypropyl group, a 4-methoxybutyl group, a methylthiomethyl group, an ethylthiomethyl group, a n-propylthiomethyl group, an i-propylthiomethyl group, a n-butylthiomethyl group, an i-butylthiomethyl group, a s-butylthiomethyl group, a t-butylthiomethyl group, a 2-methylthioethyl group, a 2-ethylthioethyl group, a 2-n-propylthioethyl group, a 2-i-propylthioethyl group, a 2-n-butylthioethyl group, a 2-t-butylthioethyl group, a 3-methylthiopropyl group, a 4-methylthiobutyl group, a methylsulfinylmethyl group, an ethylsulfinylmethyl group, a n-propylsulfinylmethyl group, an i-propylsulfinylmethyl group, a n-butylsulfinylmethyl group, an i-butylsulfinylmethyl group, a s-butylsulfinylmethyl group, a t-butylsulfinylmethyl group, a 2-methylsulfinylethyl group, a 2-ethylsulfinylethyl group, a 2-n-propylsulfinylethyl group, a 2-i-propylsulfinylethyl group, a 2-n-butylsulfinylethyl group, a 2-t-butylsulfinylethyl group, a 3-methylsulfinylpropyl group, a 4-methylsulfinylbutyl group, a methylsulfonylmethyl group, an ethylsulfonylmethyl group, a n-propylsulfonylmethyl group, an i-propylsulfonylmethyl group, a n-butylsulfonylmethyl group, an i-butylsulfonylmethyl group, a s-butylsulfonylmethyl group, a t-butylsulfonylmethyl group, a 2-methylsulfonylethyl group, a 2-ethylsulfonylethyl group, a 2-n-propylsulfonylethyl group, a 2-i-propylsulfonylethyl group, a 2-n-butylsulfonylethyl group, a 2-t-butylsulfonylethyl group, a 3-methylsulfonylpropyl group, a 4-methylsulfonylbutyl group, a methylaminomethyl group, an ethylaminomethyl group, a n-propylaminomethyl group, an i-propylaminomethyl group, an-butylaminomethyl group, a t-butylaminomethyl group, a 2-methylaminoethyl group, a 2-ethylaminoethyl group, a 2-n-propylaminoethyl group, a 2-i-propylaminoethyl group, a 3-methylaminopropyl group, a 4-methylaminobutyl group, a cyclopropylmethyl group, a cyclopentylmethyl group, a cyclohexylmethyl group, a cycloheptylmethyl group, a 2-cyclopropylethyl group, a 2-cyclohexylethyl group, a dimethylaminomethyl group, a 2-dimethylaminoethyl group, a 3-dimethylaminopropyl group, a 4-dimethylaminobutyl group, a diethylaminomethyl group, a 2-diethylaminoethyl group, a 3-diethylaminopropyl group, a 4-diethylaminobutyl group, a methoxymethoxy group, a 2-methoxyethoxy group, an ethoxymethoxy group, a 2-ethoxyethoxy group, a fluorine atom, a chlorine atom, a bromine atom, an iodine atom, etc., preferably a trifluoromethyl group, a difluoromethyl group, a chlorodifluoromethyl group, a pentafluoroethyl group, an ethyl group, an-propyl group, an i-propyl group, a n-butyl group, an i-butyl group, a s-butyl group, a t-butyl group, a 2,2-dimethylpropyl group, a 1,1-dimethylpropyl group, a cyclopropyl group, an i-propenyl group, a 2-propenyl group, a methoxymethyl group, an ethoxymethyl group, an i-propoxymethyl group, a 2-methoxyethyl group, a 2-ethoxyethyl group, a fluorine atom, a chlroine atom, a bromine atom and an iodine atom. Preferred are a $C_1$ to $C_4$ haloalkyl group, a $C_2$ to $C_6$ alkyl group, a $C_3$ to $C_7$ cycloalkyl group, a $C_2$ to $C_6$ alkenyl group, a $C_1$ to $C_4$ alkoxy ($C_1$ to $C_4$) alkyl group and a halogen atom.

As $R^2$, there may be mentioned a hydrogen atom, a methyl group, an ethyl group, a n-propyl group, an iso-propyl group, a n-butyl group, an iso-butyl group, a sec-butyl group, a fluorine atom, a chlorine atom, a bromine atom, an iodine atom, a trifluoromethyl group, a difluoromethyl group, a chlorofluoromethyl group, a pentafluoroethyl group and a nitro group, preferably a hydrogen atom and a methyl group.

As $R^3$, there may be mentioned a methyl group, an ethyl group, a n-propyl group, an iso-propyl group, a n-butyl group, an iso-butyl group, a sec-butyl group, a tert-butyl group, a n-pentyl group, a neo-pentyl group, a n-hexyl group, an allyl group, a 3-methyl-2-propenyl group, a 2-methyl-2-propenyl group, a propargyl group, a 3-methyl-2-propynyl group, a cyclopropyl group, a cyclobutyl group, a cyclopentyl group, a cyclohexyl group, a cycloheptyl group, an amino group, etc., preferably a $C_1$ to $C_6$ alkyl group, particularly a methyl group, an ethyl group and an amino group.

As $R^4$, there may be mentioned a hydrogen atom, a methyl group, an ethyl group, a n-propyl group, an i-propyl group, a n-butyl group, an i-butyl group, a s-butyl group, a n-pentyl group, a n-hexyl group, an ethenyl group, a 2-propenyl group, a 2-methyl-2-propenyl group, a 2-butenyl group, a 2-propynyl group, a 2-butynyl group, a difluoromethyl group, a chloromethyl group, a 2-chloroethyl group, a methoxymethyl group, an ethoxymethyl group, a 2-methoxyethyl group, a 2-ethoxyethyl group, a hydroxycarbonylmethyl group, a 1-hydroxycarbonylethyl group, a methoxycarbonylmethyl group, an ethoxycarbonylmethyl group, a 1-methoxycarbonylethyl group, a 1-ethoxycarbonylethyl group, a formyl group, an acetyl group, an ethylcarbonyl group, a n-propylcarbonyl group, an i-propylcarbonyl group, a t-butylcarbonyl group, a methoxycarbonyl group, an ethoxycarbonyl group, a n-propylcarbonyl group, an i-propylcarbonyl group, an aminocarbonyl group, a methylaminocarbonyl group, an ethylaminocarbonyl group, a methylsulfonyl group, a dimethylaminocarbonyl group, a diethylaminocarbonyl group, a benzyl group, a o-chlorobenzyl group, a m-chlorobenzyl group, a p-chlorobenzyl group, a o-methylbenzyl group, a m-methylbenzyl group, a p-methylbenzyl group, a m-trifluoromethylbenzyl group, etc., preferably a hydrogen atom and a $C_1$ to $C_4$ alkyl group, particularly a methyl group and an ethyl group.

As X, there may be mentioned an oxygen atom and a sulfur atom, particularly an oxygen atom.

As Q, there may be mentioned

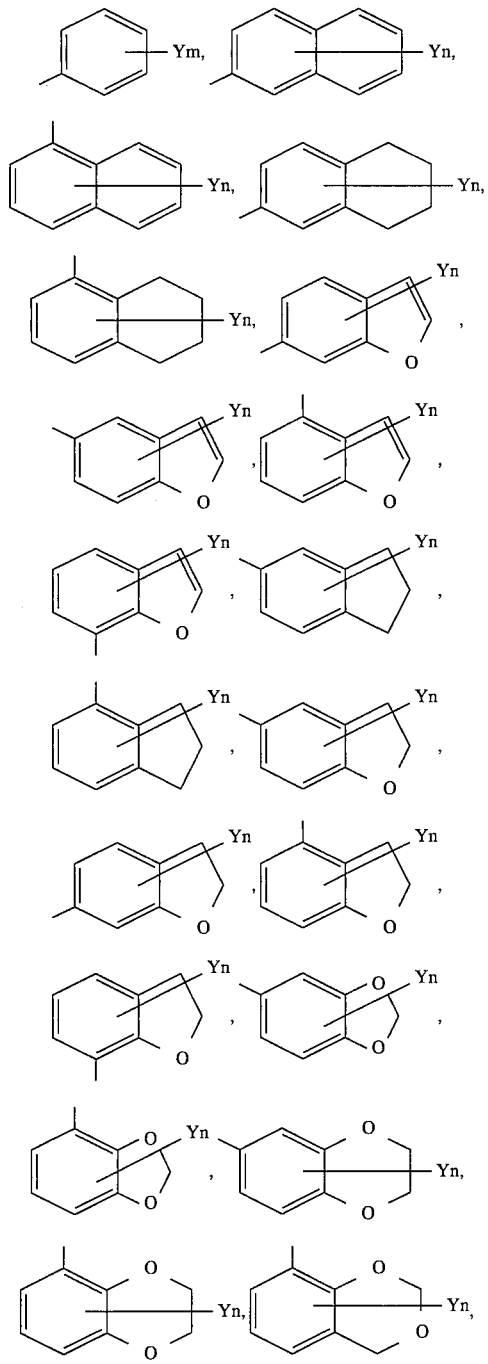

-continued

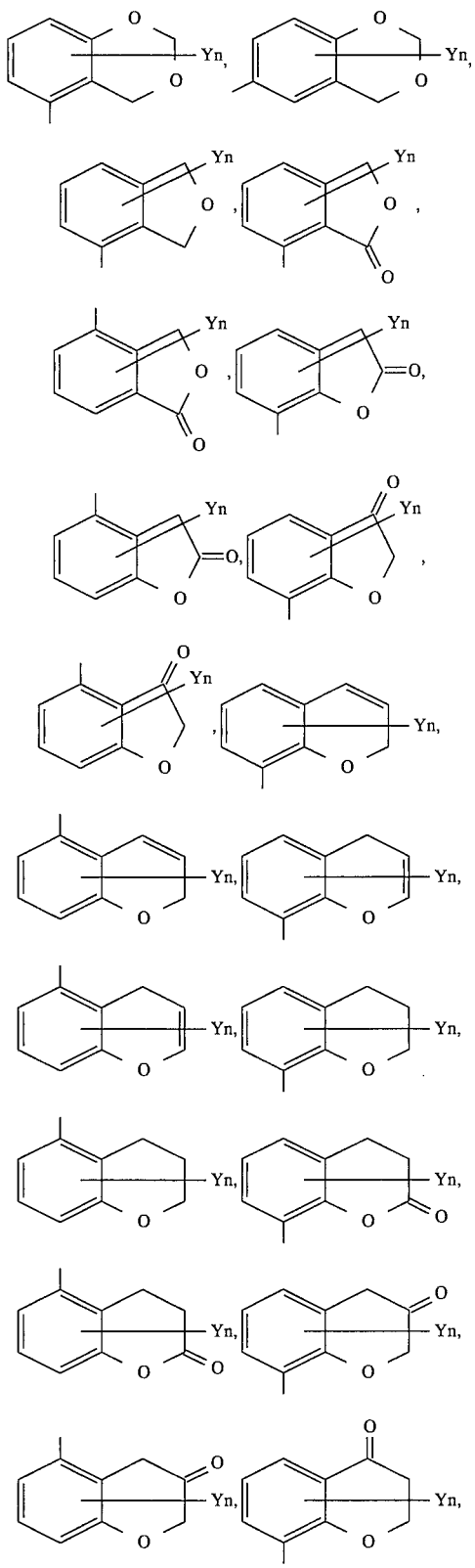

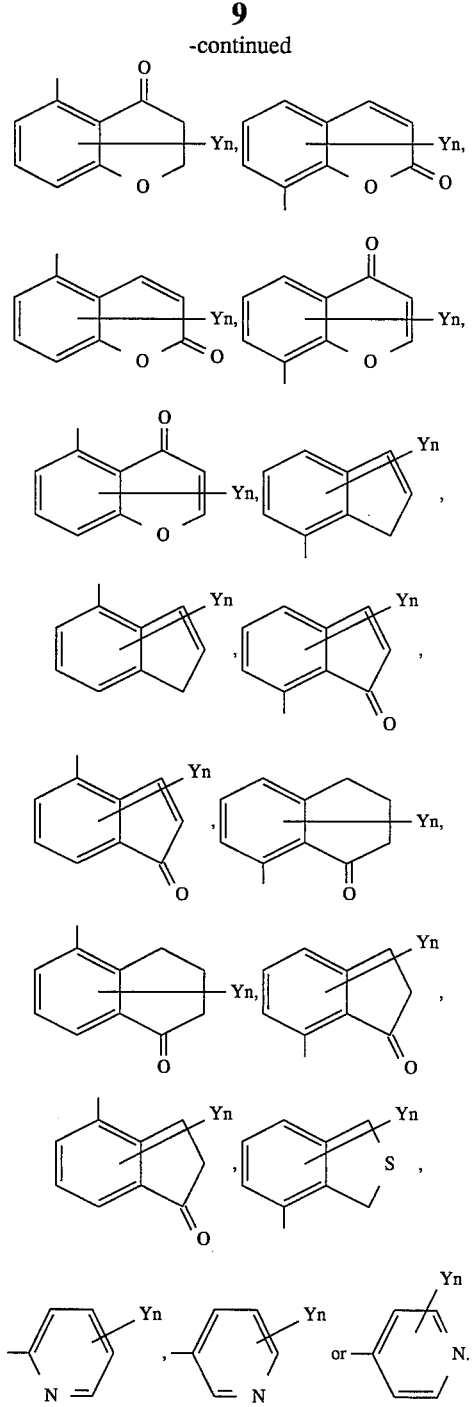

As Y which is a substituent thereof, there may be mentioned a fluorine atom, a chlorine atom, a bromine atom, an iodine atom, a methyl group, an ethyl group, a n-propyl group, an iso-propyl group, a n-butyl group, an iso-butyl group, a sec-butyl group, a tert-butyl group, a methoxy group, an ethoxy group, a n-propoxy group, an iso-propoxy group, a n-butoxy group, an iso-butoxy group, a sec-butoxy group, a tert-butoxy group, a methoxymethyl group, a 2-methoxyethyl group, an ethoxymethyl group, a 2-ethoxyethyl group, a fluoromethyl group, a chloromethyl group, a bromomethyl group, a trichloromethyl group, a trifluoromethyl group, a 1-chloroethyl group, a 2-chloroethyl group, a 3-chloropropyl group, a trifluoromethoxy group, a difluoromethoxy group, a 2-chloroethoxy group, a 3-chloropropoxy group, a 2-chloro-1-methylethoxy group, a 2,2,2-trifluoroethoxy group, a methylthio group, an ethylthio group, a n-propylthio group, an iso-propylthio group, a n-butylthio group, an iso-butylthio group, a sec-butylthio group, a tert-butylthio group, a methylsulfinyl group, an ethylsulfinyl group, a n-propylsulfinyl group, an iso-propylsulfinyl group, a n-butylsulfinyl group, an iso-butylsulfinyl group, a sec-butylsulfinyl group, a tert-butylsulfinyl group, a methylsulfonyl group, an ethylsulfonyl group, a n-propylsulfonyl group, an iso-propylsulfonyl group, a n-butylsulfonyl group, an iso-butylsulfonyl group, a sec-butylsulfonyl group, an acetyl group, an ethylcarbonyl group, a n-propylcarbonyl group, a methoxycarbonyl group, an ethoxycarbonyl group, a n-propoxycarbonyl group, an iso-propoxycarbonyl group, a n-butoxycarbonyl group, an iso-butoxycarbonyl group, a sec-butoxycarbonyl group, a tert-butoxycarbonyl group, a 2-propenyl group, a 2-propenyloxy group, a 2-methyl-2-propenyloxy group, a 2-butenyloxy group, a 2-propynyloxy group, a 1-methyl-2-propynyloxy group, an acetoxy group, an ethylcarbonyloxy group, a methoxymethoxy group, an ethoxymethoxy group, a i-propoxymethoxy group, a 2-methoxyethoxy group, a hydroxycarbonylmethyl group, a 1-(hydroxycarbonyl)ethyl group, a methoxycarbonylmethyl group, an ethoxycarbonylmethyl group, a 1-(methoxycarbonyl)ethyl group, a hydroxycarbonylmethoxy group, a 1-(hydroxycarbonyl)ethoxy group, a methoxycarbonylmethoxy group, an ethoxycarbonylmethoxy group, a 1-(methoxycarbonyl)ethoxy group, a methylamino group, an ethylamino group, a n-propylamino group, a i-propylamino group, a n-butylamino group, a dimethylamino group, a diethylamino group, an acetylamino group, a methylsulfonylamino group, an ethylsulfonylamino group, a thiol group, a cyano group, a carboxy group, an amino group, a hydroxy group, etc.

The compound of the present invention can be used as a herbicide for an upland field, a paddy field and a non-cultivated field in either treatment method of soil treatment and stem and foliar treatment.

As target weeds of the compound of the present invention as a herbicide, there may be mentioned grass weeds such as wild sorghum, fall panicum, Johnson grass, livid amaranthus, crabgrass, oats, wire grass, foxtail, water foxtail, etc., weeds of Cyperaceae family such as nut grass, etc., narrow-leaved arrowhead, *Sagittaria trifolia L., Sagittaria pygmaea Miq.*, small flower umbrella-plant, flatstage, bulrush, water chestnut, false pimpernel, monochoria, bog pondweed, spike-flowered rotala, barnyardgrass, etc.

The compound of the present invention has characteristics that it exhibits growth control of a plant as a plant growth regulator, causes no chemical damage to useful crops, does not lower qualities thereof, and has long residual effect.

The compound of the present invention includes a compound which can be used safely for wheat, corn, barley, soy bean, rice, cotton, beet, sorghum, etc. which are important crops.

The compound of the present invention is also useful as a defoliant.

The compound of the present invention represented by the formula (1) can be tautomers as shown below when $R^4$ is a hydrogen atom. The compound of the present invention includes all these tautomers when $R^4$ is a hydrogen atom.

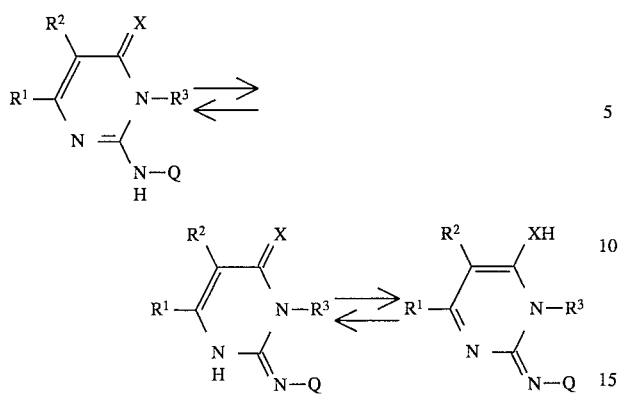

The compound of the present invention can be synthesized by, for example, the following methods shown in Schemes 1 to 5 ($R^1$, $R^2$, $R^3$, $R^4$, X and Q in Schemes 1 to 5 represent the same meanings as described above, $G^1$ represents a $C_1$ to $C_4$ alkyl group or a benzyl group and r represents 0, 1 or 2).

Scheme 1

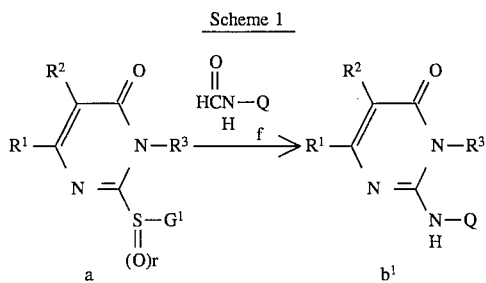

(1) Scheme 1 represents a method for preparing a 2-arylaminopyrimidinone derivative $b^1$ by reacting a 2-mercaptopyrimidine derivative a with a formamide f. In general, an amount of 0.5 to 2.0 equivalent, preferably 0.8 to 1.2 equivalent of f is used based on a.

In the reaction, a solvent is generally required. As the solvent, there may be mentioned aliphatic hydrocarbons such as hexane, heptane, ligroin, petroleum ether, etc., aromatic hydrocarbons such as benzene, toluene, xylene, chlorobenzene, etc., halogenated hydrocarbons such as chloroform, methylene chloride, etc., ethers such as diethyl ether, dioxane, tetrahydrofuran, etc., ketones such as acetone, methyl ethyl ketone, etc., nitriles such as acetonitrile, isobutyronitrile, etc., tertiary amines such as pyridine, N,N-diethylaniline, etc., acid-amides such as N,N-dimethylacetamide, N,N-dimethylformamide, N-methylpyrrolidone, etc. and sulfur-containing compounds such as dimethylsulfoxide, sulforane, etc., preferably the above aliphatic hydrocarbons, aromatic hydrocarbons, acid amides and sulfur-containing compounds, and mixtures of these.

In general, an amount of 0.5 to 3.0 equivalent, preferably 0.8 to 1.5 equivalent of a base is used based on a. As the base, there may be mentioned nitrogen-containing organic bases such as pyridine, triethylamine, N,N-dimethylaniline, N,N-diethylaniline, 4-(N,N-dimethylamino)pyridine, 1,4-diazabicyclo[2.2.2]octane, etc., inorganic bases such as sodium hydride, potassium hydride, sodium hydroxide, potassium hydroxide, sodium carbonate, potassium carbonate, etc. and organic metal bases such as n-butyllithium, phenyllithium, etc., preferably inorganic bases such as sodium hydride, sodium hydroxide, potassium hydroxide, etc.

The reaction temperature is generally −10° to 200° C., preferably room temperature to reflux temperature of a reaction mixture.

The reaction time is generally 10 minutes to 96 hours, preferably 30 minutes to 48 hours.

Scheme 2

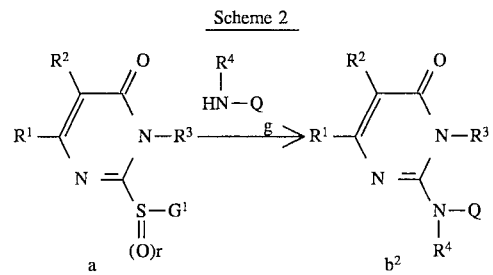

(wherein $R^4$ represents a hydrogen atom, a $C_1$ to $C_6$ alkyl group, a $C_2$ to $C_6$ alkenyl group, a $C_3$ to $C_6$ alkynyl group, a $C_1$ to $C_4$ alkoxy ($C_1$ to $C_4$) alkyl (2) Scheme 2 represents a method for preparing a 2-arylaminopyrimidinone derivative $b^2$ by reacting the 2-mercaptopyrimidine derivative a with aromatic amines g. In general, an amount of 0.8 equivalent to an extremely excessive amount, preferably an amount of 1.0 to 10 equivalent of is used based on a. The reaction generally proceeds in the absence of a solvent, but the solvent and base mentioned in Scheme 1 may be used.

The reaction temperature is −10° to 250° C., preferably room temperature to reflux temperature of a reaction mixture.

The reaction time is generally 5 minutes to 72 hours, preferably 10 minutes to 48 hours.

Scheme 3

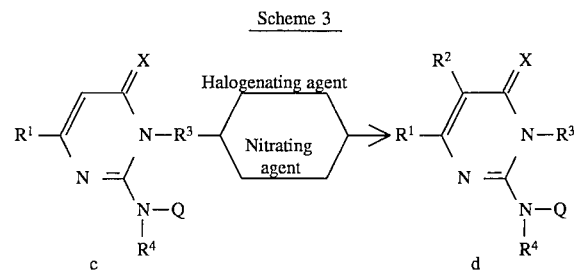

(wherein $R^2$ represents a halogen atom or a nitro group and $R^4$ represents a hydrogen atom or a $C_1$ to $C_6$ alkyl group.)

(3) Scheme 3 represents a method of halogenating or nitrating the 5-position of a 2-arylaminopyrimidinone derivative c. In general, an amount of 0.5 to 5.0 equivalent, preferably 0.8 to 1.5 equivalent of a halogenating agent or a nitrating agent is used based on c.

As the halogenating agent, there may be mentioned for example, fluorine, chlorine, bromine, iodine, sulfuryl chloride, etc. and as the nitrating agent, there may be mentioned, for example, nitric acid, copper nitrate, isoamyl nitrate, nitrogen oxides, etc.

In the halogenation, a solvent is generally required. As the solvent, there may be mentioned aliphatic hydrocarbons such as hexane, heptane, ligroin, petroleum ether, etc., aromatic hydrocarbons such as benzene, toluene, xylene, chlorobenzene, etc., halogenated hydrocarbons such as chloroform, methylene chloride, etc., ethers such as diethyl ether, dioxane, tetrahydrofuran, etc., nitriles such as acetonitrile, isobutyronitrile, etc., acid amides such as N,N-dimethylacetamide, N,N-dimethylformamide, N-methylpyrrolidone, etc., sulfur-containing compounds such as dimethylsulfoxide, sulforane, etc., alcohols such as methanol, ethanol, propanol, butanol, etc., organic acids such as formic acid, acetic acid, propionic acid, etc., water and mixtures of these, preferably the above organic acids, ethers and halogenated hydrocarbons, and mixtures of these.

The reaction temperature is generally −30° to 200° C., preferably −10° C. to reflux temperature of a reaction mixture.

The reaction time is 5 minutes to 72 hours, preferably 10 minutes to 48 hours.

The nitration proceeds even in the absence of a solvent, but it can be accelerated generally by using a solvent. As the solvent, there may be mentioned aliphatic hydrocarbons such as hexane, heptane, ligroin, petroleum ether, etc., aromatic hydrocarbons such as benzene, toluene, xylene, chlorobenzene, etc., halogenated hydrocarbons such as chloroform, methylene chloride, etc., organic acids such as formic acid, acetic acid, propionic acid, etc., mineral acids such as phosphoric acid, sulfuric acid, hydrochloric acid, etc. and mixtures of these, preferably the above halogenated hydrocarbons, aromatic hydrocarbons, organic acids and mineral acids, and mixtures of these.

The reaction temperature is generally −50° to 200° C., preferably −20° C. to reflux temperature of a reaction mixture.

The reaction time is 5 minutes to 72 hours, preferably 10 minutes to 48 hours.

Scheme 4

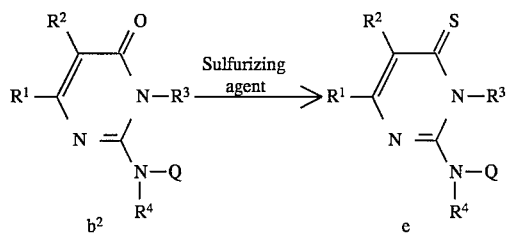

(4) Scheme 4 represents a method for preparing a 2-arylaminopyrimidine4-thion derivative e by reacting the 2-arylaminopyrimidinone derivative $b^2$ with a sulfurizing agent.

In general, an amount of 0.5 to 20 equivalent, preferably an amount of 0.8 to 10 equivalent of a sulfurizing agent is used based on b. As the sulfurizing agent, there may be mentioned phosphorus pentasulfide, [2,4-bis(4-methoxyphenyl)-1,3-dithia-2,4-diphosphetane-2,4-disulfide] (Lawesson's reagent), etc.

The reaction may proceed even in the absence of a solvent, but it can be accelerated generally by using a solvent. As the solvent, there may be mentioned aliphatic hydrocarbons such as hexane, heptane, ligroin, petroleum ether, etc., aromatic hydrocarbons such as benzene, toluene, xylene, chlorobenzene, etc., halogenated hydrocarbons such as chloroform, methylene chloride,. etc., ethers such as diethyl ether, dioxane, tetrahydrofuran, etc., tertiary amines such as pyridine, N,N-diethylaniline, etc., acid amides such as N,N-dimethylacetamide, N,N-dimethylformamide, N-methylpyrrolidone, etc. and sulfur-containing compounds such as dimethylsulfoxide, sulforane, etc., and mixtures of these, preferably the above aliphatic hydrocarbons, aromatic hydrocarbons, ethers, tertiary amines and sulfur-containing compounds, and mixtures of these.

The reaction temperature is generally 0° to 200° C., preferably room temperature to reflux temperature of a reaction mixture.

The reaction time is generally 5 minutes to 72 hours, preferably 10 minutes to 48 hours.

Scheme 5

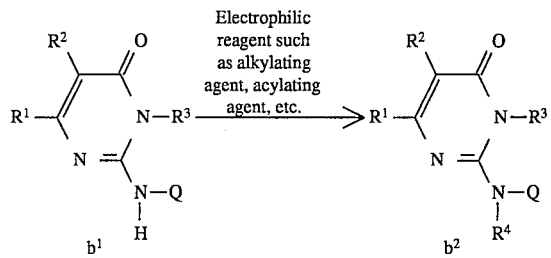

(5) Scheme 5 represents a method of substituting $R^4$ on the nitrogen atom of the 2-arylamino group by reacting the 2-arylaminopyrimidinone derivative $b^1$ with an electrophilic reagent such as an alkylating agent, an acylating agent, isocyanates, etc. In general, an amount of 0.5 to 10 equivalent, preferably 0.8 to 5 equivalent of an electrophilic reagent is used based on $b^1$.

As the electrophilic reagent, there may be mentioned, for example, alkyl sulfates such as dimethyl sulfate, diethyl sulfate, etc., halogenated alkyls such as methyl chloride, methyl bromide, methyl iodide, ethyl chloride, ethyl bromide, ethyl iodide, isopropyl iodide, normal butyl bromide, difluorobromomethane, methoxymethyl chloride, ethoxymethyl chloride, 2-methoxyethyl chloride, etc., halogenated alkenyls such as allyl chloride, allyl bromide, etc., halogenated alkynyls such as propargyl chloride, propargyl bromide, etc., halogenated organic acids and halogenated organic acid esters such as chloroacetic acid, bromoacetic acid, ethyl chloroacetate, methyl bromoacetate, α-chloropropionic acid, methyl α-bromopropionate, etc., organic acids such as formic acid, acetic acid, etc., acid anhydrides such as acetic anhydride, propionic anhydride, etc., acid chlorides such as acetyl chloride, methyl chloroformate, ethyl chloroformate, methanesulfonyl chloride, N,N-dimethylcarbamoyl chloride, N,N-diethylcarbamoyl chloride, etc., isocyanates such as methyl isocyanate, ethyl isocyanate, isopropyl isocyanate, etc., benzyl halides such as benzyl chloride, benzyl bromide, o-chlorobenzyl chloride, p-chlorobenzyl chloride, p-methylbenzyl bromide, etc. and others.

In the reaction, a solvent and a base are generally used, and the solvent and base mentioned in Scheme 1 can be used.

The reaction temperature is generally −10° to 200° C., preferably 0° C. to reflux temperature of a reaction mixture.

The reaction time is generally 5 minutes to 95 hours, preferably 10 minutes to 48 hours.

The 2-mercaptopyrimidine derivative a which is a starting material can be prepared according to, for example, the following reaction schemes a and b.

Reaction scheme a

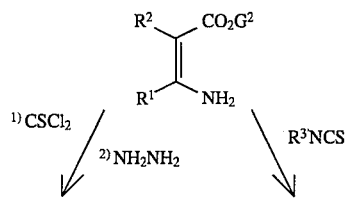

-continued
Reaction scheme a

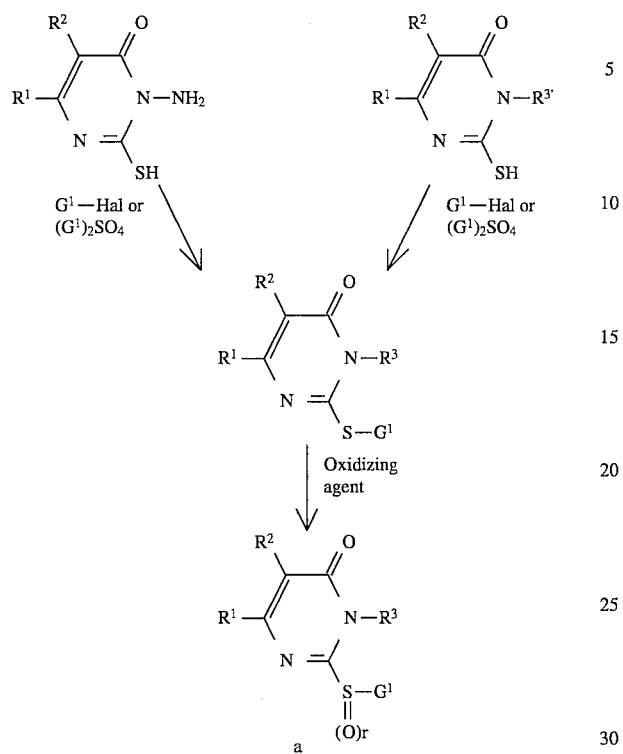

(wherein $R^1$, $R^2$, $R^3$, $G^1$ and r have the same meanings as described above, $G^2$ represents a $C_1$ to $C_4$ alkyl group or a phenyl group, $R^{3'}$ represents a $C_1$ to $C_6$ alkyl group, a $C_3$ to $C_6$ alkenyl group, a $C_3$ to $C_6$ alkynyl group or a $C_3$ to $C_7$ cycloalkyl group, and Hal represents a halogen atom provided that the case where $R^1$ is a $C_1$ to $C_6$ haloalkyloxy group, a $C_1$ to $C_6$ alkoxy group, a $C_3$ to $C_7$ cycloalkyloxy group, a $C_3$ to $C_6$ alkenyloxy group, a $C_1$ to $C_6$ haloalkylthio group, a $C_1$ to $C_6$ alkylthio group, a $C_3$ to $C_7$ cycloalkylthio group, a $C_3$ to $C_6$ alkenylthio group, a $C_1$ to $C_6$ haloalkylsulfinyl group, a $C_1$ to $C_6$ alkylsulfinyl group, a $C_3$ to $C_7$ cycloalkylsulfinyl group, a $C_3$ to $C_6$ alkenylsulfinyl group, a $C_1$ to $C_6$ haloalkylsulfonyl group, a $C_1$ to $C_6$ alkylsulfonyl group, a $C_3$ to $C_7$ cycloalkylsulfonyl group, a $C_3$ to $C_6$ alkenylsulfonyl group, a $C_1$ to $C_4$ alkoxy ($C_1$ to $C_4$) alkoxy group or a halogen atom is excluded.)

Reaction scheme b $R^3NHCNH_2 + R^2CH(CO_2G^2)_2$
 ‖
 S

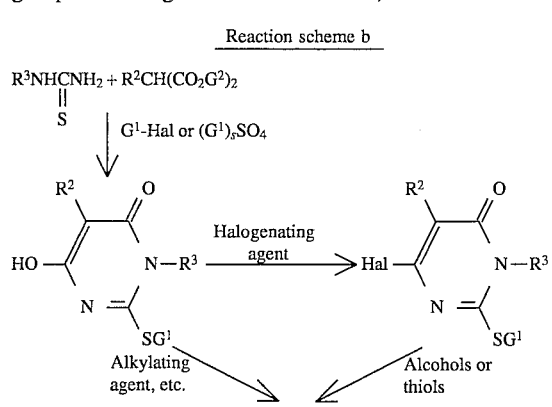

-continued
Reaction scheme b

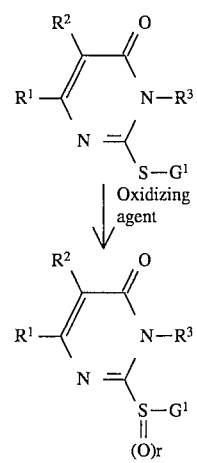

(wherein $R^1$, $R^2$, $R^3$, $G^1$, r, $G^2$ and Hal have the same meanings as described above provided that the case where $R^1$ is a $C_1$ to $C_4$ haloalkyl group, a $C_2$ to $C_6$ alkyl group, a $C_3$ to $C_7$ cycloalkyl group, a $C_2$ to $C_6$ alkenyl group, a $C_1$ to $C_4$ alkoxy ($C_1$ to $C_4$) alkyl group, a $C_1$ to $C_4$ alkylthio ($C_1$ to $C_4$) alkyl group, a $C_1$ to $C_4$ alkylsulfinyl ($C_1$ to $C_4$) alkyl group, a $C_1$ to $C_4$ alkylsulfonyl ($C_1$ to $C_4$) alkyl group, a $C_1$ to $C_4$ alkylamino ($C_1$ to $C_4$) alkyl group, a $C_3$ to $C_7$ cycloalkyl ($C_1$ to $C_4$) alkyl group, a dimethylamino ($C_1$ to $C_4$) alkyl group or a diethylamino ($C_1$ to $C_4$) alkyl group is excluded, the case where $R^2$ is a halogen atom or a nitro group is excluded, and further the case where $R^3$ is an amino group is excluded.)

When it becomes necessary to purify the compound of the present invention, it can be separated and purified according to any desired purification method such as recrystallization, column chromatography, etc.

Further, among the compounds included in the present invention, a compound having asymmetric carbons includes optically active compounds (+) isomer and (−) isomer. When a geometrical isomer is present, a trans isomer and a cis isomer are included.

BEST MODE FOR CARRYING OUT THE INVENTION

In the following, synthetic examples of the compound of the present invention are described in detail by referring to Reference examples and Examples, but the present invention is not limited by these.

Reference Example 1

Synthesis of 3-methyl-2-methylthio-6-trifluoromethyl-4(3H)-pyrimidinone

① Synthesis of 2-mercapto-3methyl-6-trifluoromethyl-4(3H)-pyrimidinone

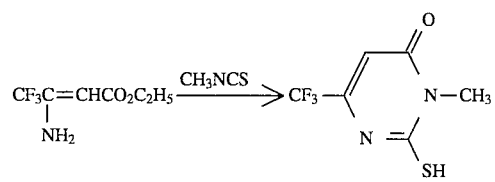

In 50 ml of N,N-dimethylformamide was dissolved 14 g (0.076 mol) of ethyl 4,4,4-trifluoro-3-aminocrotonate, and 3.3 g of 55% sodium hydride was added thereto.

To the solution was added dropwise 5 g (0.068 mol) of methylthioisocyanate at 5° C. or lower, and the mixture was reacted at room temperature overnight.

After completion of the reaction, N,N-dimethylformamide was removed under reduced pressure, and then the residue was dissolved in water. The resulting aqueous solution was made acidic with hydrochloric acid, and crystals precipitated were filtered, washed with water and dried to obtain 12.9 g (yield: 81%) of 2-mercapto-3-methyl-6-trifluoromethyl-4(3H)-pyrimidinone.

② Synthesis of 3-methyl-2-methylthio-6-trifluoromethyl-4(3H)-pyrimidinone

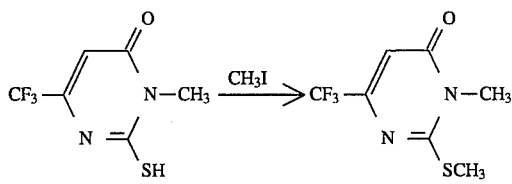

In 50 ml of N,N-dimethylformamide was dissolved 10 g (0.048 mol) of 2-mercapto-3-methyl-6-trifluoromethyl-4(3H)-pyrimidinone, and 7.24 g of potassium carbonate was added thereto.

To the solution was added dropwise 7.43 g (0.052 mol) of methyl iodide at 5° C. or lower, and the mixture was reacted at room temperature overnight.

After completion of the reaction, N,N-dimethylformamide was removed under reduced pressure, and then the residue was dissolved in ethyl acetate. The resulting ethyl acetate solution was washed with water and then with a saturated saline solution and dried over anhydrous sodium sulfate. Thereafter, ethyl acetate was removed under reduced pressure to obtain white crystals. The crystals were washed with hexane to obtain 7.8 g (yield: 73%) of the title compound, 3-methyl-2-methylthio-6-trifluoromethyl-4(3H)-pyrimidinone.

Reference Example 2

Synthesis of 6-methoxy-3-methyl-2-methylthio- 4(3H)-pyrimidinone

① Synthesis of 6-hydroxy-3-methyl-2-methylthio-4(3H)-pyrimidinone

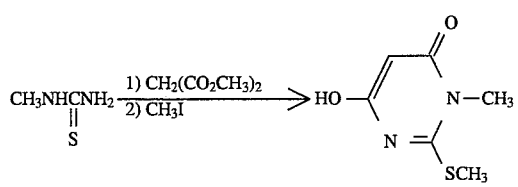

In 250 ml of methanol was dissolved 13.1 g of metal sodium. To the resulting methanol solution were added 25 g (0.28 mol) of N-methylthiourea and 38.5 g (0.29 mol) of dimethyl malonate, and the mixture was reacted under reflux for 3 hours. Thereafter, to the solution was added dropwise 41.3 g (0.29 mol) of methyl iodide at 10° C. or lower, and the mixture was reacted at room temperature overnight. After completion of the reaction, methanol was removed under reduced pressure, and then the residue was dissolved in water. The resulting aqueous solution was made acidic with hydrochloric acid, and crystals precipitated were filtered, washed with water and dried to obtain 42.4 g (yield: 89%) of 6-hydroxy-3-methyl-2-methylthio-4(3H)-pyrimidinone.

② Synthesis of 6-methoxy-3-methyl-2-methylthio-4(3H)-pyrimidinone

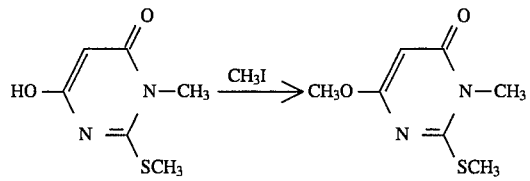

In 100 ml of N,N-dimethylformamide was dissolved 10 g (0.058 mol) of 6-hydroxy-3-methyl-2-methylthio-4(3H)-pyrimidinone, and 4.4 g of potassium carbonate was added thereto. To the solution was added dropwise 8.7 g (0.061 mol) of methyl iodide at room temperature, and the mixture was reacted at 50° C. for 2 hours.

After completion of the reaction, N,N-dimethylformamide was removed under reduced pressure, and then the residue was dissolved in ethyl acetate. The resulting ethyl acetate solution was washed with water and then with a saturated saline solution and dried over anhydrous sodium sulfate. Thereafter, ethyl acetate was removed under reduced pressure to obtain white crystals. The crystals were washed with diisopropyl ether to obtain 5.5 g (yield: 51%) of the title compound, 6-methoxy-3-methyl-2-methylthio-4(3H)-pyrimidinone.

EXAMPLE 1

Synthesis of 2-(4-chloro-2-fluorophenyl)amino-3-methyl-6-trifluoromethyl-4(3H)-pyrimidinone (Compound A-1)

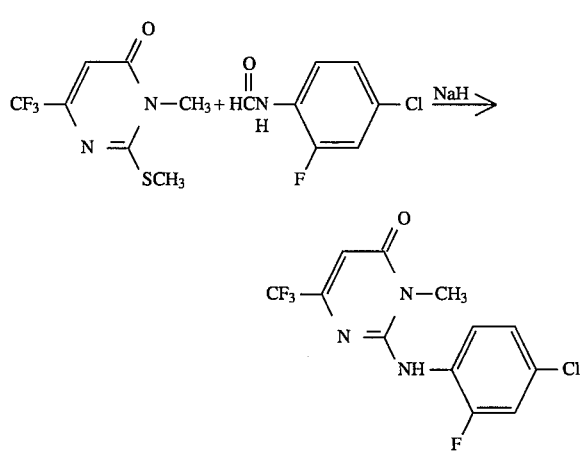

To a mixed solution of 1 g (4.46 mmol) of 3-methyl-2-methylthio-6-trifluoromethyl-4(3H)-pyrimidinone, 0.73 g (4.21 mmol) of 4-chloro-2-fluoroformanilide and 20 ml of N,N-dimethylformamide was added 0.20 g of 60% sodium hydride, and the mixture was heated to 100° C. for 5 minutes and then reacted at room temperature overnight. After completion of the reaction, ice water was added to the reaction mixture, and the mixture was extracted with ethyl acetate. The extract was washed with water and then with a saturated saline solution and dried over anhydrous sodium sulfate. Thereafter, ethyl acetate was removed under reduced pressure to obtain a crude product. This crude product was crystallized from diisopropyl ether, followed by washing, to obtain 0.7 g (yield: 49%) of the title compound as white crystals.

EXAMPLE 2

Synthesis of 2-(4-chloro-2-fluorophenyl)amino-3-ethyl-6-trifluoromethyl-4(3H)-pyrimidinone (Compound A-3)

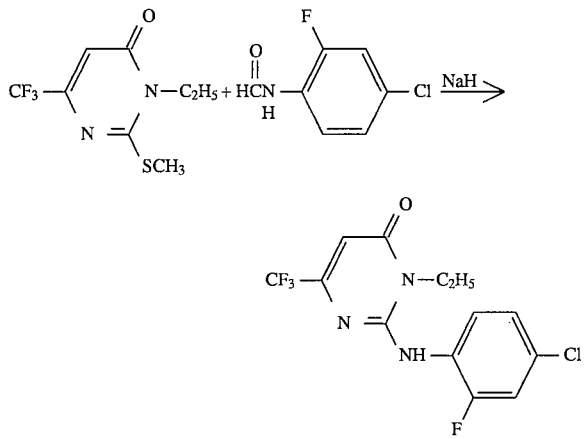

To a mixed solution of 1 g (4.20 mmol) of 3-ethyl-2-methylthio- 6-trifluoromethyl-4(3H)-pyrimidinone, 0.77 g (4.44 mmol) of 4-chloro-2-fluoroformanilide and 20 ml of N,N-dimethylformamide was added 0.21 g of 60% sodium hydride, and the mixture was heated at 80° C. for 3 hours. After completion of the reaction, ice water was added to the reaction mixture, and the mixture was extracted with ethyl acetate. The extract was washed with water and then with a saturated saline solution and dried over anhydrous sodium sulfate. Thereafter, ethyl acetate was removed under reduced pressure to obtain a crude product.

This crude product was purified by preparative thin layer chromatography (a developing solvent: n-hexane:ethyl acetate=3:1) to obtain 0.14 g (yield: 10%) of the title compound as white crystals.

EXAMPLE 3

Synthesis of 2-(3-bromo-2-methylphenyl)amino-3-methyl-6-trifluoromethyl-4(3H)-pyrimidinone (Compound A-73)

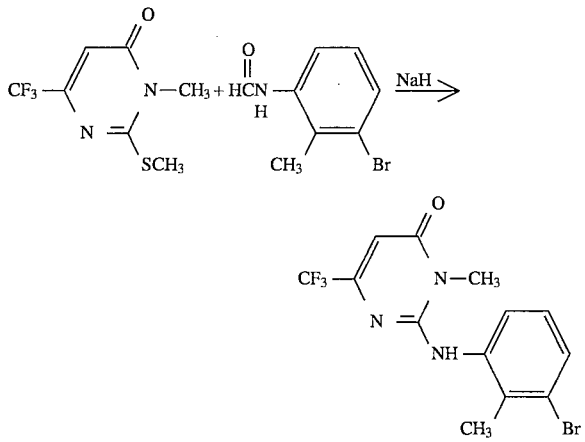

In the same manner as in Example 1, 0.5 g (2.23 mmol) of 3-methyl-2-methylthio-6-trifluoromethyl-4(3H)-pyrimidinone and 0.5 g (2.34 mmol) of 3-bromo-2-methylformanilide were heated at 100° C. for 5 minutes in 5 ml of N,N-dimethylformamide in the presence of 0.1 g of 60% sodium hydride and then reacted at room temperature overnight to obtain 0.40 g (yield: 50%) of the title compound as white crystals.

EXAMPLE 4

Synthesis of 3-methyl-2-[1-(5,6,7,8-tetrahydro)naphthyl]amino-6-trifluoromethyl-4(3H)-pyrimidinone (Compound A-78)

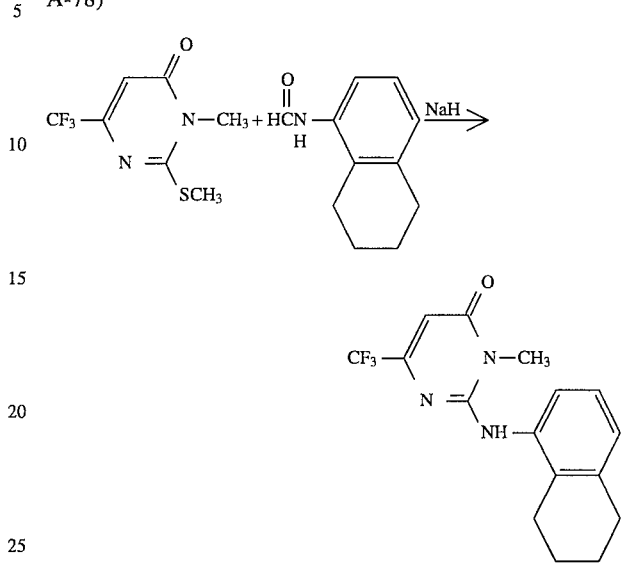

In the same manner as in Example 1, 1 g of 3-methyl-2-methylthio-6-trifluoromethyl-4(3H)-pyrimidinone and 0.74 g of 1-formylamino-5,6,7,8-tetrahydronaphthalene were heated at 100° C. for 5 minutes in 20 ml of N,N-dimethylformamide in the presence of 0.2 g of 60% sodium hydride and then reacted at room temperature overnight to obtain 0.46 g (yield: 34%) of the title compound as white crystals.

EXAMPLE 5

Synthesis of 3-methyl-2-(1-naphthyl)amino-6-trifluoromethyl- 4(3H)-pyrimidinone (Compound A-24)

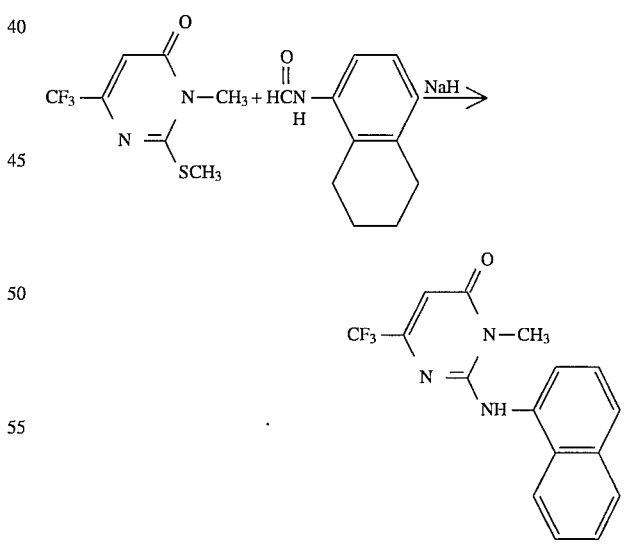

In the same manner as in Example 1, 1 g of 3methyl-2-methylthio- 6-trifluoromethyl-4(3H)-pyrimidinone and 0.72 g of 1-formylaminonaphthalene were heated at 100° C. for 5 minutes in 20 ml of N,N-dimethylformamide in the presence of 0.2 g of 60% sodium hydride and then reacted at room temperature overnight to obtain 1.05 g (yield: 78%) of the title compound as white crystals.

EXAMPLE 6

Synthesis of 3-methyl-2-[2-(3,5-dichloro)pyridyl]amino-6-trifluoromethyl-4(3H)-pyrimidinone (Compound A-83)

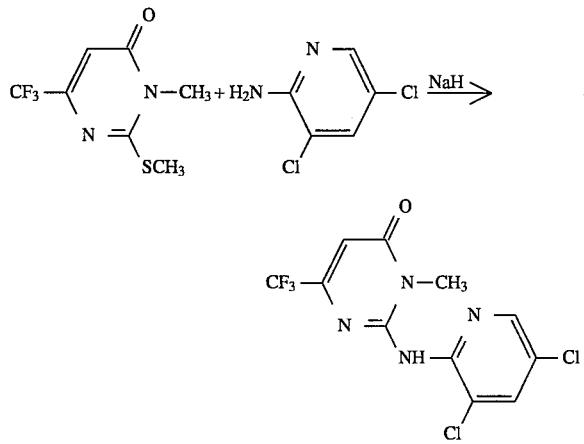

To a mixture of 0.5 g (2.23 mmol) of 3-methyl-2-methylthio-6-trifluoromethyl-4(3H)-pyrimidinone, 0.38 g (2.23 mmol) of 2-amino-3,5-dichloropyridine and 5 ml of N,N-dimethylformamide was added 0.18 g (4.46 mmol) of 60% sodium hydride. The mixture was heated to 70° C. for 5 minutes and then reacted at room temperature for 5 hours. After completion of the reaction, ice water was added to the reaction mixture, and the mixture was extracted with ethyl acetate. The extract was washed with water and then with a saturated saline solution and dried over anhydrous sodium sulfate. Ethyl acetate was removed by evaporation under reduced pressure to obtain a crude product. This product was washed with diisopropyl ether to obtain 0.33 g (yield: 43% of the title compound as pale yellow crystals.

EXAMPLE 7

Synthesis of 5-chloro-2-(4-chloro-2-fluorophenyl)amino-3-methyl-6-trifluoromethyl-4(3H)-pyrimidinone (Compound A-21)

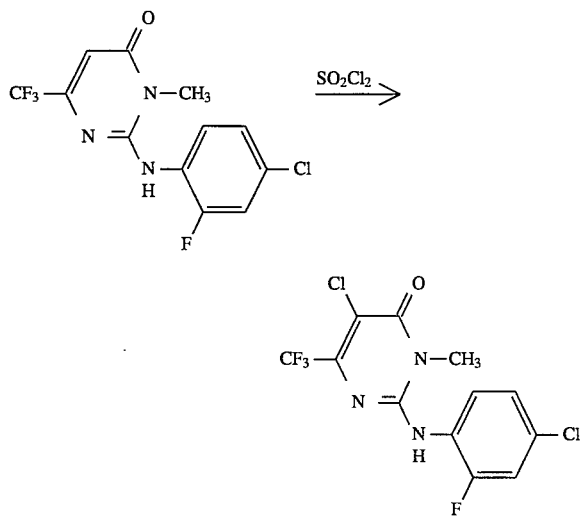

In 3 ml of acetic acid was dissolved 0.30 g (0.93 mmol) of 2-(4-chloro-2-fluorophenyl)amino-3-methyl-6-trifluoromethyl-4(3H)-pyrimidinone synthesized in Example 1, and 0.07 ml (0.93 mmol) of sulfuryl chloride was added dropwise thereto. The mixture was reacted for 2 hours. The reaction mixture was poured into ice water, and crystals precipitated were filtered to obtain a crude product. This product was purified by preparative thin layer chromatography (hexane-ethyl acetate, 3:1) to obtain 0.21 g (yield: 70%) of the title compound as white crystals.

EXAMPLE 8

Synthesis of 3-methyl-2-(1-naphthyl)amino-6-trifluoromethyl- 3H-pyrimidine-4-thione (Compound A-88)

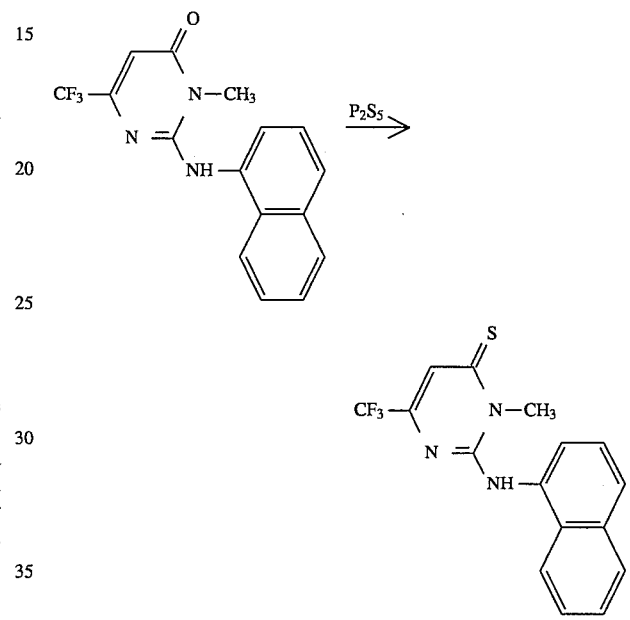

A mixture of 3.0 g (9.4 mmol) of 3-methyl-2-(1-naphthyl)amino-6-trifluoromethyl-4(3H)-pyrimidinone synthesized in Example 5, 41 ml of pyridine and 4.2 g (18.8 mmol) of phosphorus pentasulfide was refluxed by heating for 16 hours. After the reaction, pyridine was removed by evaporation under reduced pressure, and the residue was dissolved in ethyl acetate. The solution was washed with diluted hydrochloric acid, with water and then with a saturated saline solution and dried over anhydrous sodium sulfate. Thereafter, ethyl acetate was removed by evaporation under reduced pressure to obtain a crude product. This product was washed with diisopropyl ether to obtain 2.4 g (yield: 77%) of the title compound as yellow crystals.

EXAMPLE 9

Synthesis of 2-(3-iodo-2-methylphenyl)amino-3-methyl-6-pentafluoroethyl-4(3H)-pyrimidinone (Compound A-105)

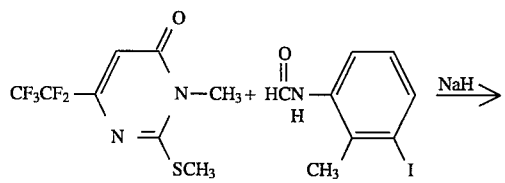

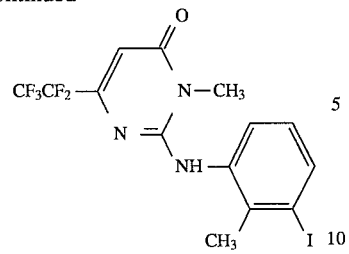

In the same manner as in Example 1, 0.5 g (1.82 mmol) of 3-methyl-2-methylthio-6-pentafluoroethyl-4(3H)-pyrimidinone and 0.39 g (1.82 mmol) of 3-iodo-2-methyl-formanilide were heated at 100° C. for 5 minutes in 5 ml of N,N-dimethylformamide in the presence of 0.08 g of 60% sodium hydride and then reacted at room temperature overnight to obtain 0.14 g (yield: 19%) of the title compound as white crystals.

EXAMPLE 10

Synthesis of 2-(3-allyloxy-2-methylphenyl)amino-3-methyl-6-trifluoromethyl-4(3H)-pyrimidinone (Compound A-119)

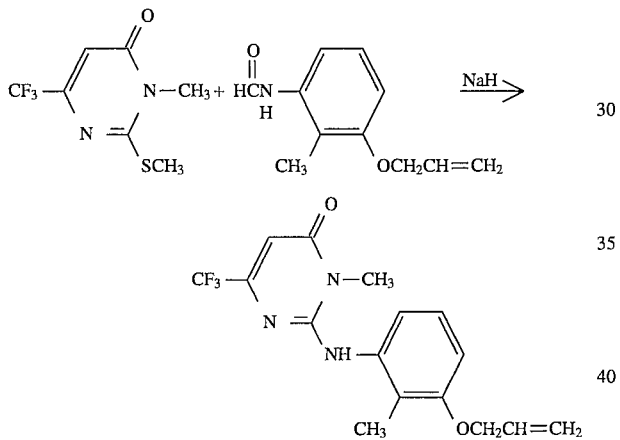

In the same manner as in Example 1, 0.5 g (2.23 mmol) of 3-methyl-2-methylthio-6-trifluoromethyl-4(3H)-pyrimidinone and 0.45 g (2.36 mmol) of 3-allyloxy-2-methylformanilide were heated at 100° C. for 5 minutes in 5 ml of N,N-dimethylformamide in the presence of 0.1 g of 60% sodium hydride and then reacted at room temperature overnight to obtain 0.48 g (yield: 63%) of the title compound as white crystals.

EXAMPLE 11

Synthesis of 3-methyl-2-(2-methyl-3-trifluoromethylphenyl)amino- 6-trifluoromethyl-4(3H)-pyrimidinone (Compound A-121)

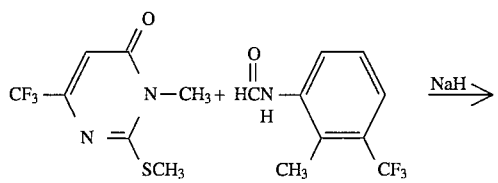

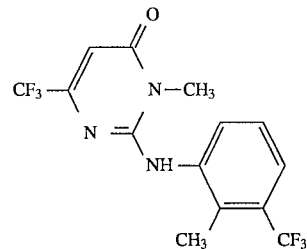

In the same manner as in Example 1, 0.5 g (2.23 mmol) of 3-methyl-2-methylthio-6-trifluoromethyl-4(3H)-pyrimidinone and 0.48 g (2.36 mmol) of 2-methyl-3-trifluoromethylformanilide were heated at 100° C. for 5 minutes in 5 ml of N,N-dimethylformamide in the presence of 0.1 g of 60% sodium hydride and then reacted at room temperature overnight to obtain 0.32 g (yield: 41%) of the title compound as white crystals.

EXAMPLE 12

Synthesis of 2-(3-iodo-2-methylphenyl)amino-3-methyl-6-propyl-4(3H)-pyrimidinone (Compound A-124)

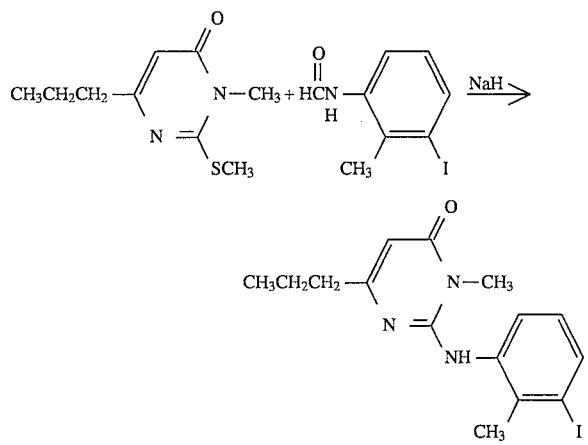

To a solution of 0.69 g (2.64 mmol) of 3-iodo-2-methylformanilide dissolved in 5 ml of N,N-dimethylformamide were added 0.12 g of 60% sodium hydride and further 0.5 g (2.53 mmol) of 3-methyl-2-methylthio-6-propyl-4(3H)-pyrimidinone. The mixture was reacted at 80° C. for 6 hours.

After completion of the reaction, ice water was added to the reaction mixture, and the mixture was extracted with ethyl acetate. The extract was washed with water and then with a saturated saline solution and dried over anhydrous sodium sulfate. Thereafter, ethyl acetate was removed under reduced pressure to obtain a crude product. This crude product was purified by preparative thin layer chromatography (a developing solvent: n-hexane:ethyl acetate=1:1) to obtain 0.2 g (yield: 21%) of the title compound as pale yellow crystals.

EXAMPLE 13

Synthesis of 2-(3-bromo-2-methylphenyl)amino-3-methyl-6-i-propyl-4(3H)-pyrimidinone (Compound A-125)

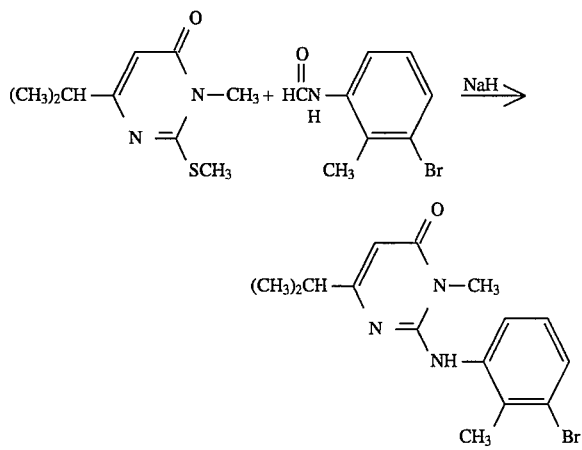

In the same manner as in Example 12, 0.5 g (2.53 mmol) of 3-methyl-2-methylthio-6-i-propyl-4(3H)-pyrimidinone and 0.69 g (2.64 mmol) of 3-bromo-2-methylformanilide were reacted at 120° C. for 4 hours in 5 ml of N,N-dimethylformamide in the presence of 0.12 g of 60% sodium hydride to obtain 0.30 g (yield: 31%) of the title compound as white crystals.

EXAMPLE 14

Synthesis of 6-t-butyl-2-(3-iodo-2-methylphenyl)amino-3-methyl-4(3H)-pyrimidinone (Compound A-131)

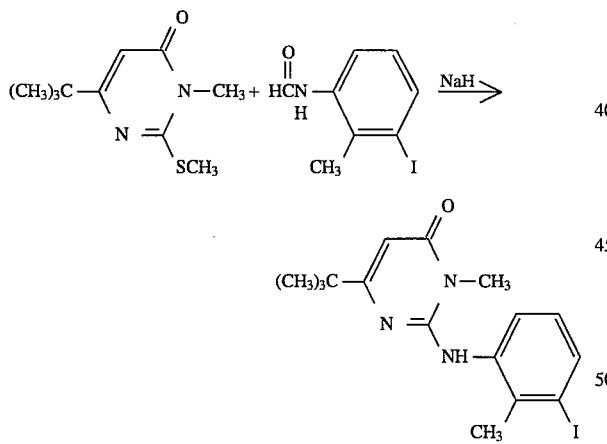

In the same manner as in Example 12, 0.82 g (3.87 mmol) of 6-t-butyl-3-methyl-2-methylthio-4(3H)-pyrimidinone and 1 g (3.83 mmol) of 3-iodo-2-methylformanilide were reacted at 100° C. for 9 hours in 10 ml of N,N-dimethylformamide in the presence of 0.17 g of 60% sodium hydride to obtain 0.50 g (yield: 33%) of the title compound as white crystals.

EXAMPLE 15

Synthesis of 2-(3-bromo-2-methylphenyl)amino-6-methoxymethyl-3-methyl-4(3H)-pyrimidinone (Compound A-132)

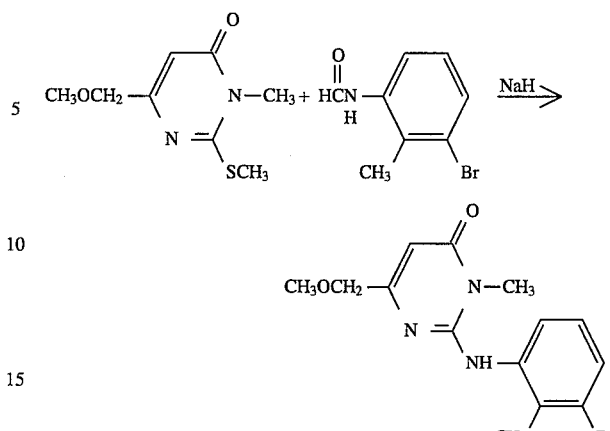

In the same manner as in Example 12, 0.98 g (4.90 mmol) of 6-methoxymethyl-3-methyl-2-methylthio-4(3H)-pyrimidinone and 1 g (4.67 mmol) of 3-bromo-2-methylformanilide were reacted at 100° C. for 7 hours in 10 ml of N,N-dimethylformamide in the presence of 0.21 g of 60% sodium hydride to obtain 0.86 g (yield: 52%) of the title compound as white crystals.

EXAMPLE 16

Syntheses of 2-(5-indanyl)amino-3-methyl-6-trifluoromethyl-4(3H)-pyrimidinone (Compound A-136) and 2-(4-indanyl)amino-3-methyl-6-trifluoromethyl-4(3H)-pyrimidinone (Compound A-137)

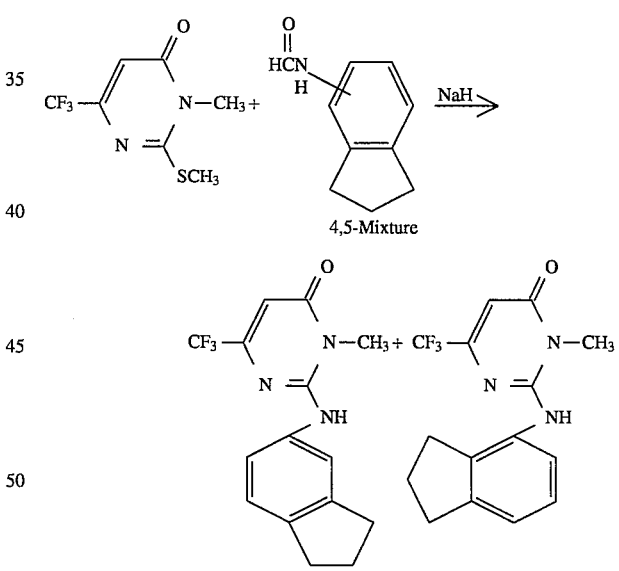

In the same manner as in Example 1, 2.24 g (10 mmol) of 3-methyl-2-methylthio-6-trifluoromethyl-4(3H)-pyrimidinone and 1.6 g of a mixture (about 1:1) of 4-formylaminoindane and 5-formylaminoindane were reacted at room temperature overnight in 20 ml of N,N-dimethylformamide in the presence of 0.42 g of 60% sodium hydride to obtain 1.9 g of a mixture of the two title compounds as white crystals. This mixture was separated by preparative liquid chromatography (reverse phase system; 50% acetonitrile aqueous solution) to obtain both of 0.85 g of 2-(5-indanyl)amino-3-methyl-6-trifluoromethyl- 4(3H)-pyrimidinone and 0.82 g of 2-(4-indanyl)amino- 3-methyl-6-trifluoromethyl-4(3H)-pyrimidinone as white crystals.

EXAMPLE 17

Synthesis of 2-(2-fluoro-3-trifluoromethylphenyl)amino-3-methyl-6-trifluoromethyl-4(3H)-pyrimidinone (Compound A-102)

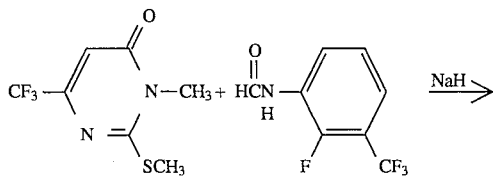

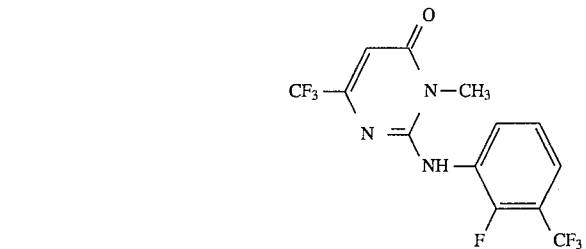

In the same manner as in Example 1, 4.6 g (20.5 mmol) of 3-methyl-2-methylthio-6-trifluoromethyl-4(3H)-pyrimidinone and 3.55 g (17.1 mmol) of 2-fluoro-3-trifluoromethylformanilide were heated at 100° C. for 30 minutes in 35 ml of N,N-dimethylformamide in the presence of 0.83 g of 55% sodium hydride and then reacted at room temperature overnight to obtain 1.76 g (yield: 29%) of the title compound as white crystals.

EXAMPLE 18

Synthesis of 2-[N-(2-fluoro-3-trifluoromethylphenyl)-N-methyl]amino-3-methyl-6-trifluoromethyl-4(3H)-pyrimidinone (Compound B-7)

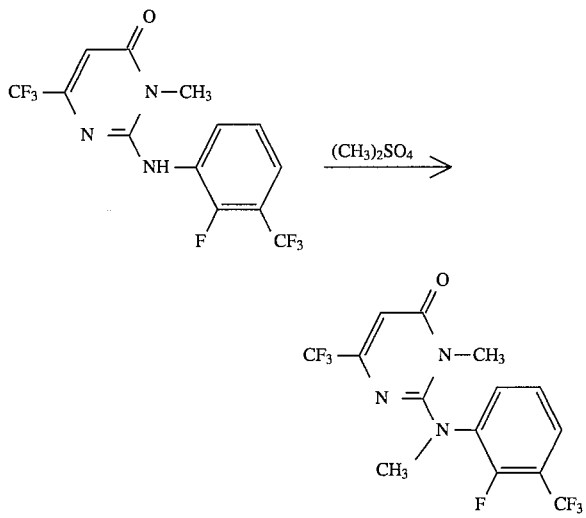

In 3 ml of N,N-dimethylformamide was dissolved 0.67 g (1.89 mmol) of 2-(2-fluoro-3-trifluoromethylphenyl)amino-3-methyl-6-trifluoromethyl-4(3H)-pyrimidinone, and 0.79 g (5.72 mmol) of potassium carbonate was added thereto. To the solution was added dropwise 0.54 ml (5.71 mmole) of dimethyl sulfate, and the mixture was reacted at room temperature for 7 days. After completion of the reaction, ice water was added to the reaction mixture, and the mixture was extracted with ethyl acetate. The extract was washed with water, with a saturated sodium hydrogen carbonate solution and then with a saturated saline solution and dried over anhydrous sodium sulfate. Thereafter, ethyl acetate was removed under reduced pressure to obtain a crude product. This crude product was purified by preparative thin layer chromatography (a developing solvent: n-hexane:ethyl acetate=3:1) to obtain 0.20 g (yield: 29%) of the title compound as white crystals.

EXAMPLE 19

Synthesis of 2-[N-ethyl-N-(4-chloro-2-fluorophenyl)]amino-3-methyl-6-trifluoromethyl-4(3H)-pyrimidinone (Compound B-2)

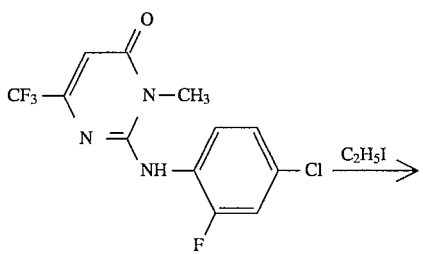

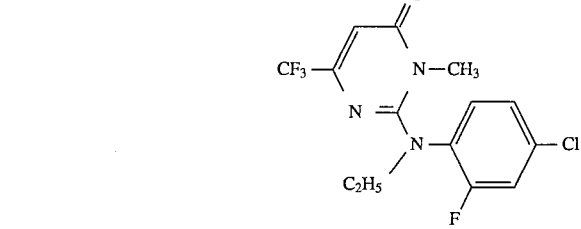

In 5 ml of N,N-dimethylformamide was dissolved 0.5 g (1.56 mmol) of 2-(4-chloro-2-fluorophenyl)amino-3-methyl-6-trifluoromethyl-4(3H)-pyrimidinone, and 0.08 g of 55% sodium hydride was added thereto. To the solution was added dropwise 0.27 g (1.73 mmol) of ethyl iodide at 5° C. or lower, and the mixture was reacted at 70° C. for 6 hours. After completion of the reaction, ice water was added to the reaction mixture, and the mixture was extracted with ethyl acetate. The extract was washed with water and then with a saturated saline solution and dried over anhydrous sodium sulfate. Thereafter, ethyl acetate was removed under reduced pressure to obtain a crude product. This crude product was purified by preparative thin layer chromatography (a developing solvent: n-hexane:ethyl acetate=5:1) to obtain 0.3 g (yield: 55%) of the title compound as viscous oil.

EXAMPLE 20

Synthesis of 2-[N-(3-bromo-2-methylphenyl)-N-methyl]amino-3-methyl-6-trifluoromethyl-4(3H)-pyrimidinone (Compound B-6)

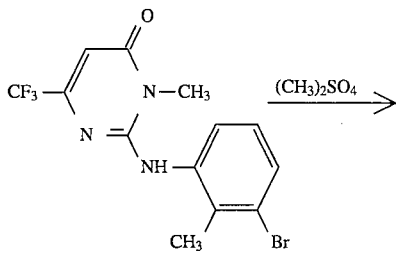

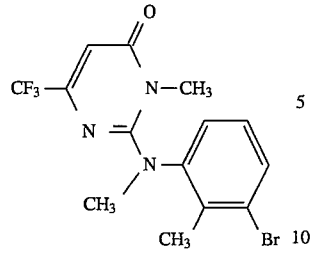

In the same manner as in Example 18, 0.60 g (1.66 mmol) of 2-(3-bromo-2-methylphenyl)amino-3-methyl-6-trifluoromethyl- 4(3H)-pyrimidinone and 0.47 ml (4.97 mmol) of dimethyl sulfate were reacted at room temperature for 4 days in 3 ml of N,N-dimethylformamide in the presence of 0.69 g (4.97 mmol) of potassium carbonate to obtain 0.43 g (yield: 69%) of the title compound as yellow oil.

EXAMPLE 21

Synthesis of 2-(3-chloro-2,4-difluorophenyl)amino-3-methyl-6-trifluoromethyl-4(3H)-pyrimidinone (Compound A-164)

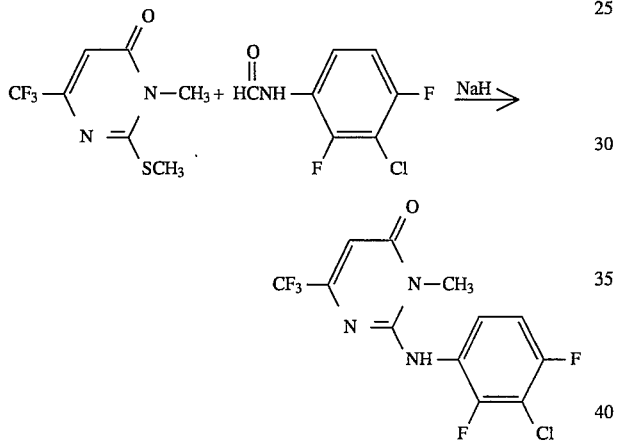

In the same manner as in Example 1, 1.29 g (5.76 mmol) of 3-methyl-2-methylthio-6-trifluoromethyl-4(3H)-pyrimidinone and 1 g (5.22 mmol) of 3-chloro-2,4-difluoroformanilide were heated at 80° C. for 20 minutes in 10 ml of N,N-dimethylformamide in the presence of 0.23 g of 60% sodium hydride and then reacted at room temperature overnight to obtain 0.56 g (yield: 32%) of the title compound as white crystals.

EXAMPLE 22

Synthesis of 2-[N-(3-chloro-2,4-difluorophenyl)-N-methyl]amino-3-methyl-6-trifluoromethyl-4(3H)pyrimidinone (Compound B-26)

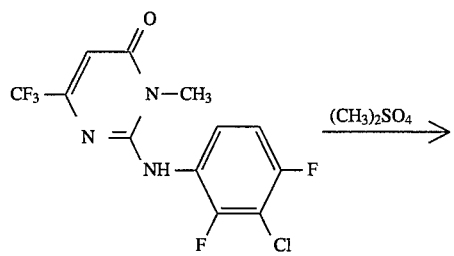

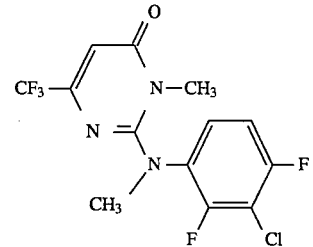

In the same manner as in Example 18, 0.45 g (1.33 mmol) of 2-(3-chloro-2,4-difluorophenyl)amino-3-methyl-6-trifluoromethyl-4(3H)-pyrimidinone and 1.26 ml (13.3 mmol) of dimethyl sulfate were reacted at room temperature for 6 days in 4 ml of N,N-dimethylformamide in the presence of 1.84 g (13.3 mmol) of potassium carbonate to obtain 0.26 g (yield: 55%) of the title compound as transparent oil. Thereafter, the oil was solidified at room temperature to obtain white crystals.

EXAMPLE 23

Synthesis of 2-(3-bromo-2,4-difluorophenyl)amino-3-methyl-6-trifluoromethyl-4(3H)-pyrimidinone (Compound A-177)

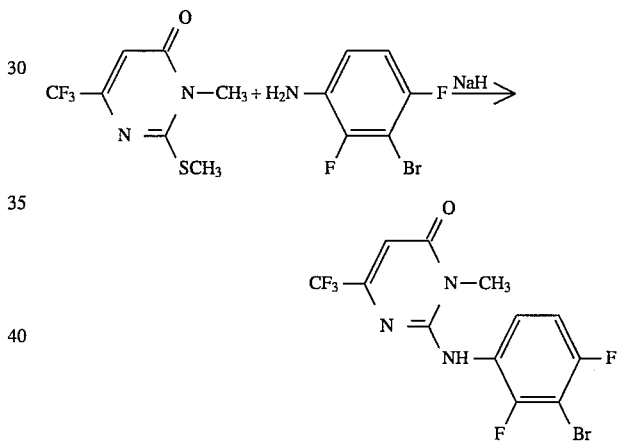

To a solution of 0.53 g (2.25 mmol) of 3-bromo-2,4-difluoroaniline dissolved in 10 ml of N,N-dimethylformamide was added 0.15 g of 60% sodium hydride, and the mixture was stirred at room temperature for 20 minutes. Then, to the mixture was added 0.8 g (3.57 mmol) of 3-methyl-2-methylthio-6-trifluoromethyl-4(3H)-pyrimidinone, and the mixture was reacted at 80° C. for 4 hours. After completion of the reaction, ice water was added to the reaction mixture, and the mixture was extracted with ethyl acetate. The extract was washed with a saturated sodium hydrogen carbonate solution and then with a saturated saline solution and dried over anhydrous sodium sulfate. Thereafter, ethyl acetate was removed under reduced pressure to obtain a crude product. This crude product was crystallized from and washed with hexane to obtain 0.77 g (yield: 89%) of the title compound as white crystals.

EXAMPLE 24

Synthesis of 2-[N-(3-bromo-2,4-difluorophenyl)-N-methyl]amino-3-methyl-6-trifluoromethyl-4(3H)-pyrimidinone (Compound B-37)

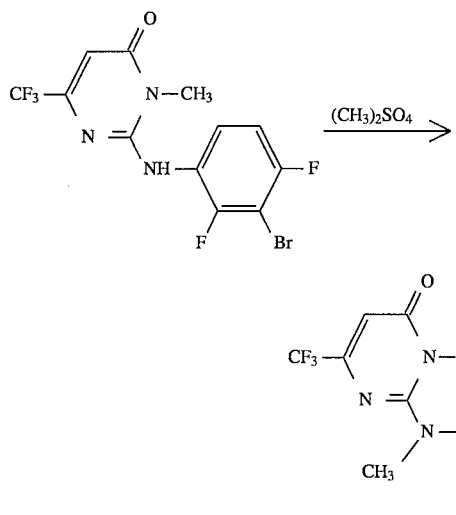

In the same manner as in Example 18, 0.44 g (1.15 mmol) of 2-(3-bromo-2,4-difluorophenyl)amino-3-methyl-6-trifluoromethyl-4(3H)-pyrimidinone and 1.62 ml (17.1 mmol) of dimethyl sulfate were reacted at room temperature for 4 days in 5 ml of N,N-dimethylformamide in the presence of 2.37 g (17.1 mmol) of potassium carbonate to obtain 0.26 g (yield: 57%) of the title compound as white crystals.

As to the compounds of the present invention synthesized according to the above schemes or Examples including the compounds synthesized in the above Examples, structures are shown in Table 1-A and Table 1-B, and physical properties are shown in Table 2.

TABLE 1-A

| Compound No. | $R^1$ | $R^2$ | $R^3$ | X | Q |
|---|---|---|---|---|---|
| A-1 | $CF_3$ | H | Me | O | 2-F-4-Cl-Ph |
| A-2 | $CF_3$ | H | Me | O | 4-Cl-Ph |
| A-3 | $CF_3$ | H | Et | O | 2-F-4-Cl-Ph |
| A-4 | $CF_3$ | H | Me | O | 3-Cl-Ph |
| A-5 | $CF_3$ | H | Me | O | 2-Me-Ph |
| A-6 | $CF_3$ | H | Me | O | 3-Me-Ph |
| A-7 | $CF_3$ | H | Me | O | 4-Me-Ph |
| A-8 | $CF_3$ | H | Me | O | 2-OMe-Ph |
| A-9 | $CF_3$ | H | Me | O | 3-OMe-Ph |
| A-10 | $CF_3$ | H | Me | O | 4-OMe-Ph |
| A-11 | $CF_3$ | H | Me | O | 2-Cl-Ph |
| A-12 | $CF_3$ | H | Me | O | 2-$CF_3$-Ph |
| A-13 | $CF_3$ | H | Me | O | 3-$CF_3$-Ph |
| A-14 | $CF_3$ | H | Me | O | 2-F-Ph |
| A-15 | $CF_3$ | H | Me | O | 4-$CF_3$-Ph |
| A-16 | $CF_3$ | H | Me | O | 2,6-$Cl_2$-Ph |
| A-17 | $CF_3$ | H | Me | O | 2,6-$Me_2$-Ph |
| A-18 | $CF_3$ | H | Me | O | 2-Et-Ph |
| A-19 | $CF_3$ | H | Me | O | 2-Br-Ph |
| A-20 | $CF_3$ | H | Me | O | 2-I-Ph |
| A-21 | $CF_3$ | Cl | Me | O | 2-F-4-Cl-Ph |
| A-22 | $CF_3$ | Br | Me | O | 2-F-4-Cl-Ph |
| A-23 | $CF_3$ | I | Me | O | 2-F-4-Cl-Ph |
| A-24 | $CF_3$ | H | Me | O | Q3 |
| A-25 | $CF_3$ | H | Me | O | 2,6-$F_2$-Ph |
| A-26 | $CF_3$ | H | Me | O | 2-COMe-Ph |
| A-27 | $CF_3$ | H | Me | O | 2,4-$Me_2$-Ph |
| A-28 | $CF_3$ | H | Me | O | 2-Me-4-OMe-Ph |
| A-29 | $CF_3$ | H | Me | O | 2-Cl-4-Me-Ph |
| A-30 | $CF_3$ | H | Me | O | 2-Cl-4-F-Ph |
| A-31 | $CF_3$ | H | Me | O | 2-Me-4-F-Ph |
| A-32 | $CF_3$ | H | Me | O | 2-F-4-Me-Ph |
| A-33 | $CF_3$ | H | Me | O | 2,4-$Cl_2$-Ph |
| A-34 | $CF_3$ | H | Me | O | 3,4-$(OMe)_2$-Ph |
| A-35 | $CF_3$ | H | Me | O | 2,3-$Me_2$-Ph |
| A-36 | $CF_3$ | H | Me | O | 2,5-$Me_2$-Ph |
| A-37 | $CF_3$ | H | Me | O | 2,3-$Cl_2$-Ph |
| A-38 | $CF_3$ | H | Me | O | 2,5-$Cl_2$-Ph |
| A-39 | $CF_3$ | H | Me | O | 3,4-$Me_2$-Ph |
| A-40 | $CF_3$ | H | Me | O | 2-Me-3-Cl-Ph |
| A-41 | $CF_3$ | H | Me | O | 2-Me-5-Cl-Ph |

TABLE 1-A-continued $$\underset{\underset{NH-Q}{\overset{R^2}{\underset{N}{\overset{R^1}{\bigg|}}}}}{\overset{X}{\underset{N-R^3}{\bigg|}}}$$

| Compound No. | R¹ | R² | R³ | X | Q |
|---|---|---|---|---|---|
| A-42 | CF₃ | H | Me | O | 2-Cl-5-Me—Ph |
| A-43 | CF₃ | H | Me | O | 2-Br-4-Me—Ph |
| A-44 | CF₃ | H | Me | O | 2-F—4-Cl-5-Br—Ph |
| A-45 | CF₃ | H | Me | O | 4-OEt—Ph |
| A-46 | CF₃ | H | Me | O | 4-OPro-i-Ph |
| A-47 | CF₃ | H | Me | O | 4-OCF₃—Ph |
| A-48 | CF₃ | H | Me | O | 3,5-(OMe)₂—Ph |
| A-49 | CF₃ | H | Me | O | 3,4,5-(OMe)₃—Ph |
| A-50 | CF₃ | H | Me | O | 2,5-F₂—Ph |
| A-51 | CF₃ | H | Me | O | 2,4-F₂—Ph |
| A-52 | CF₃ | H | Me | O | 2,4-(OMe)₂—Ph |
| A-53 | CF₃ | H | Me | O | 4-SMe—Ph |
| A-54 | CF₃ | H | Me | O | 3-Cl-4-OMe—Ph |
| A-55 | CF₃ | H | Me | O | 2-OMe-5-Cl—Ph |
| A-56 | CF₃ | H | Me | O | 2-F—4-Br—Ph |
| A-57 | CF₃ | H | Me | O | 4-CO₂Et—Ph |
| A-58 | CF₃ | H | Me | O | 2-CN—Ph |
| A-59 | CF₃ | H | Me | O | 3-CN—Ph |
| A-60 | CF₃ | H | Me | O | 4-CN—Ph |
| A-61 | CF₃ | H | Me | O | 3,4-F₂—Ph |
| A-63 | CF₃ | H | Me | O | 2,4,5-Cl₃—Ph |
| A-64 | CF₃ | H | Me | O | 2-SMe—Ph |
| A-65 | CF₃ | H | Me | O | 3-SMe—Ph |
| A-66 | CF₃ | H | Me | O | 2,4-Br₂—Ph |
| A-67 | CF₃ | H | Me | O | 2-Br—4-F—Ph |
| A-68 | CF₃ | H | Me | O | 2-Br-4-Cl—Ph |
| A-69 | CF₃ | H | Me | O | 2-F—4-I—Ph |
| A-70 | CF₃ | H | Me | O | 2-Cl-4-I—Ph |
| A-71 | CF₃ | H | Me | O | 2,3,4-Cl₃—Ph |
| A-72 | CF₃ | H | Me | O | 2,3-F₂—Ph |
| A-73 | CF₃ | H | Me | O | 2-Me-3-Br—Ph |
| A-74 | CF₃ | H | Me | O | 2-Cl-4-Br—Ph |
| A-75 | CF₃ | H | Me | O | 2-Me-3-F—Ph |
| A-76 | CF₃ | H | Me | O | 2-OMe-3-F—Ph |
| A-77 | CF₃ | H | Me | O | 4-Cl-Q3 |
| A-78 | CF₃ | H | Me | O | Q5 |
| A-79 | CF₃ | H | Me | O | 2-Cl-Q24 |
| A-80 | CF₃ | H | Me | O | 5-Cl-Q23 |
| A-81 | CF₃ | H | Me | O | 3-Me-Q23 |
| A-82 | CF₃ | H | Me | O | 5-Me-Q23 |
| A-83 | CF₃ | H | Me | O | 3,5-Cl₂-Q23 |
| A-84 | CF₃ | H | Me | O | 2-Me-4-I—Ph |
| A-85 | CF₃ | H | Me | O | 2-Br-4-CF₃—Ph |
| A-86 | CF₃ | H | Me | O | 2-Br—4-Bu-t-Ph |
| A-87 | CF₃ | H | Me | O | 6-OMe-Q24 |
| A-88 | CF₃ | H | Me | S | Q3 |
| A-89 | CF₃ | H | Me | O | 2-Pro-i-Ph |
| A-90 | CF₃ | H | Me | O | 2-Pro-Ph |
| A-91 | CF₃ | H | Me | O | 2-Br—3-Me—Ph |
| A-92 | CF₃ | H | Me | O | 2-I—3-Me—Ph |
| A-93 | CF₃ | H | Me | O | 2-Me—3-OMe—Ph |
| A-94 | CF₃ | H | Me | O | 2-Me—3-I—Ph |
| A-95 | CF₃ | H | Me | O | 2-Cl—3-Me—Ph |
| A-96 | CF₃ | H | Me | O | 2,3-Br₂—Ph |
| A-97 | CF₃ | H | Me | O | 3-Br—Ph |
| A-98 | CF₃ | H | Me | O | 2-OMe—3-Cl—Ph |
| A-99 | CF₃ | H | Me | O | 2-OEt—3-Cl—Ph |
| A-100 | CF₃ | H | Me | O | 2-OMe—3-Me—Ph |
| A-101 | CF₃ | H | Me | O | 2-Me—3-OEt—Ph |
| A-102 | CF₃ | H | Me | O | 2-F—-3-CF₃—Ph |
| A-103 | CF₃ | H | Me | O | 2-Me—3-OPro-i-Ph |
| A-104 | CF₃ | H | Me | O | 2-Me—3-OPro-Ph |
| A-105 | C₂F₅ | H | Me | O | 2-Me—3-I—Ph |
| A-106 | C₂F₅ | H | Me | O | 2-Me—3-Br—Ph |
| A-107 | CF₃ | H | all | O | 2-Me-3-Cl—Ph |
| A-108 | CF₃ | H | all | O | 3-CF₃-Ph |
| A-109 | CF₃ | H | all | O | 2-Me—Ph |
| A-110 | CF₃ | H | all | O | 4-OMe—Ph |

TABLE 1-A-continued

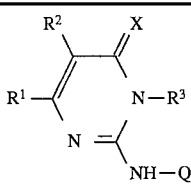

| Compound No. | R¹ | R² | R³ | X | Q |
|---|---|---|---|---|---|
| A-111 | Et | H | Me | O | 2-Me—3-I—Ph |
| A-112 | $CF_3$ | H | Me | O | 2-Me—3-$CO_2$Me—Ph |
| A-113 | $CF_3$ | H | Me | O | 2-Me—3-$NMe_2$-Ph |
| A-114 | $CF_3$ | H | c-Hex | O | 2-Me—3-Cl—Ph |
| A-115 | $CF_3$ | H | c-Hex | O | 4-Cl—Ph |
| A-116 | $CF_3$ | H | c-Hex | O | 3-$CF_3$—Ph |
| A-117 | $CF_3$ | H | c-Hex | O | 2-Me—Ph |
| A-118 | $CF_3$ | H | c-Hex | O | 4-OMe—Ph |
| A-119 | $CF_3$ | H | Me | O | 2-Me—3-Oall—Ph |
| A-120 | $CF_3$ | H | Me | O | 2-Me—3-$CH_2$OMe—Ph |
| A-121 | $CF_3$ | H | Me | O | 2-Me—3-$CF_3$—Ph |
| A-122 | $CF_3$ | H | Pro | O | 2-Me—3-Cl—Ph |
| A-123 | Et | H | Me | O | 2-Me—3-Br—Ph |
| A-124 | Pro | H | Me | O | 2-Me—3-I—Ph |
| A-125 | i-Pro | H | Me | O | 2-Me—3-Br—Ph |
| A-126 | i-Pro | H | Me | O | 2-Me—3-I—Ph |
| A-127 | $CF_3$ | H | Me | O | 2-Me—3-$NH_2$—Ph |
| A-128 | $CF_3$ | H | Me | O | 2-Me—3-$NHSO_2$Me—Ph |
| A-129 | $CF_3$ | H | Me | O | 2-Me—3-NHCOMe—Ph |
| A-130 | t-Bu | H | Me | O | 2-Me—3-Br—Ph |
| A-131 | t-Bu | H | Me | O | 2-Me—3-I—Ph |
| A-132 | $MeOCH_2$ | H | Me | O | 2-Me—3-Br—Ph |
| A-133 | $MeOCH_2$ | H | Me | O | 2-Me—3-I—Ph |
| A-134 | $CF_3$ | H | Pro | O | 3-$CF_3$—Ph |
| A-135 | $CF_3$ | H | Me | O | 2-Me—3-$OCH_2$OMe—Ph |
| A-136 | $CF_3$ | H | Me | O | Q10 |
| A-137 | $CF_3$ | H | Me | O | Q11 |
| A-138 | Et | H | Me | O | 2,3-$Cl_2$—Ph |
| A-139 | OMe | H | Me | O | 2-Me—3-Br—Ph |
| A-140 | OMe | H | Me | O | 2-Me—3-I—Ph |
| A-141 | c-Pro | H | Me | O | 2-Me—3-Br—Ph |
| A-142 | c-Pro | H | Me | O | 2-Me—3-I—Ph |
| A-143 | Oi-Pro | H | Me | O | 2-Me—3-Br—Ph |
| A-144 | Oi-Pro | H | Me | O | 2-Me—3-I—Ph |
| A-145 | $EtOCH_2$ | H | Me | O | 2-Me—3-I—Ph |
| A-146 | $EtOCH_2$ | H | Me | O | 2-Me—3-Br—Ph |
| A-147 | $CF_3$ | H | Et | O | 2-Me—3-Br—Ph |
| A-148 | $CF_3$ | H | Et | O | 3-Br—Ph |
| A-149 | i-Pro | H | Me | O | 2-F-3-$CF_3$—Ph |
| A-150 | $CF_3$ | H | Me | O | 2-Me—3-$OCH_2CO_2$Me—Ph |
| A-151 | $CF_3$ | H | Me | O | 2,2-$Me_2$-Q15 |
| A-152 | $CF_3$ | H | Me | O | Q28 |
| A-153 | $CF_3$ | H | Me | O | 6-Me-Q23 |
| A-154 | $CF_3$ | H | Me | O | 2-Me—4-OEt—Ph |
| A-155 | $CF_3$ | H | Me | O | 2-Me—4-Oi-Pro-Ph |
| A-156 | $CF_3$ | H | Me | O | 2-F—4-OMe—Ph |
| A-157 | $CF_3$ | H | Me | O | Q26 |
| A-158 | $CF_3$ | H | Me | O | 2-Me—4-$OCH_2$OMe—Ph |
| A-159 | $CF_3$ | H | Me | O | 2-Me—4-Oall-Ph |
| A-160 | $CF_3$ | H | Me | O | 2-Me-Q15 |
| A-161 | $CF_3$ | H | Me | O | 2-Me-Q12 |
| A-162 | $CF_3$ | H | Me | O | 2-Me—3-$OCH_2$C═CH-Ph |
| A-163 | $CF_3$ | H | Me | O | 2-F—4-OEt—Ph |
| A-164 | $CF_3$ | H | Me | O | 2,4-$F_2$-3-Cl—Ph |
| A-165 | $CF_3$ | H | Me | O | 2-Br-3-OMe—Ph |
| A-166 | $CF_3$ | H | Me | O | Q16 |
| A-167 | $CF_3$ | H | Me | O | Q17 |
| A-168 | $CF_3$ | H | Me | O | 2-F—3-Cl—Ph |
| A-169 | $CF_3$ | H | Me | O | 2-Me—3-$OCH_2$OEt—Ph |
| A-170 | $CF_3$ | H | Me | O | 2-Me—3-$OCH_2CH_2$OMe—Ph |
| A-171 | $CF_3$ | H | Me | O | 2-Me—3-SMe—Ph |
| A-172 | $CF_3$ | H | Me | O | 2-Me—3-$SO_2$Me—Ph |
| A-173 | $CF_3$ | H | Me | O | 2-Me—3-SOMe—Ph |
| A-174 | $CF_3$ | H | Me | O | Q15 |
| A-175 | $CF_3$ | H | Me | O | Q12 |
| A-176 | $CF_3$ | H | Me | O | I-OMe-Q11 |
| A-177 | $CF_3$ | H | Me | O | 3-Br—2,4-$F_2$-Ph |
| A-178 | $CF_3$ | H | Me | O | 3-Br—2,4-$Cl_2$—Ph |

TABLE 1-A-continued

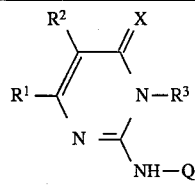

| Compound No. | R¹ | R² | R³ | X | Q |
|---|---|---|---|---|---|
| A-179 | $CF_3$ | H | Me | O | 2,4-$F_2$-3-$CO_2$Me—Ph |
| A-180 | $CF_3$ | H | Me | O | 2,4-$Cl_2$-3-Me—Ph |
| A-181 | $CF_3$ | H | Me | O | Q49 |
| A-182 | $CF_3$ | H | Me | O | l-OH-Q11 |
| A-183 | $CF_3$ | H | Me | O | l-$MeCO_2$-Q11 |
| A-184 | $CF_3$ | H | Me | O | 2,3,4-F3-Ph |
| A-185 | $CF_3$ | H | Me | O | 2,4-$F_2$-3-Me—Ph |
| A-186 | $CF_3$ | H | Me | O | Q56 |
| A-187 | $CF_3$ | H | Me | O | Q23 |
| A-188 | $CF_3$ | H | Me | O | 2,4,6-$Cl_3$—Ph |
| A-189 | $CF_3$ | H | Me | O | 2,4,6-F3-Ph |
| A-190 | $CF_3$ | H | Me | O | 3-Cl-5-$CF_3$-Q23 |
| A-191 | $CF_3$ | H | Me | O | 2,6-$Cl_2$-4-$CF_3$—Ph |
| A-192 | $CF_3$ | H | Me | O | 2,4-$F_2$-3-OMe—Ph |
| A-193 | $CF_3$ | H | Me | O | 2-OMe—3-Cl-4-F—Ph |
| A-194 | $CF_3$ | H | Me | O | 2-OMe—3,4-$Cl_2$—Ph |
| A-195 | $CF_3$ | H | Me | O | 2,4-$(OMe)_2$-3-Cl—Ph |
| A-196 | $CF_3$ | H | Me | O | 2-SMe—3-Cl-4-F—Ph |
| A-197 | $CF_3$ | H | Me | O | 2,3,4,5-$F_4$—Ph |
| A-198 | $CF_3$ | H | Me | O | 2,4,5-$F_3$—Ph |
| A-199 | $CF_3$ | H | Me | O | 2,3,5,6-$F_4$—Ph |
| A-200 | $CF_3$ | H | Me | O | 2,3,6-$F_3$—Ph |
| A-201 | $CF_3$ | H | Me | O | 2,3,5,6-$F_4$-4-Br—Ph |
| A-202 | $CF_3$ | H | Me | O | 2-Br-3,4,6-$F_3$—Ph |
| A-203 | $CF_3$ | H | Me | O | 2,3,4,5,6-$F_5$—Ph |

[TABLE 1-B]

[Structure 46]

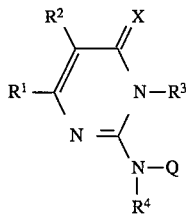

| Compound No. | R¹ | R² | R³ | R⁴ | X | Q |
|---|---|---|---|---|---|---|
| B-1 | $CF_3$ | H | Me | Me | O | 2-F-4-Cl-Ph |
| B-2 | $CF_3$ | H | Me | Et | O | 2-F-4-Cl-Ph |
| B-3 | $CF_3$ | H | Me | Me | O | Q3 |
| B-4 | $CF_3$ | H | Me | Et | O | Q3 |
| B-5 | $CF_3$ | H | Me | Me | O | 2-Me-3-Cl-Ph |
| B-6 | $CF_3$ | H | Me | Me | O | 2-Me-3-Br-Ph |
| B-7 | $CF_3$ | H | Me | Me | O | 2-F-3-$CF_3$-Ph |
| B-8 | $CF_3$ | H | Me | Me | O | 3-$CF_3$-Ph |
| B-9 | $CF_3$ | H | Me | Et | O | 2-F-3-$CF_3$-Ph |
| B-10 | $CF_3$ | H | Me | Me | O | 2-F-Ph |
| B-11 | $CF_3$ | H | Me | Me | O | 2,3-$F_2$-Ph |
| B-12 | $CF_3$ | H | Et | Me | O | 3-Br-Ph |
| B-13 | $CF_3$ | H | Me | Et | O | 3-$CF_3$-Ph |
| B-14 | $CF_3$ | H | Me | $CH_2$Ph | O | 3-$CF_3$-Ph |
| B-15 | $CF_3$ | H | Me | i-Pro | O | 3-$CF_3$-Ph |
| B-16 | $CF_3$ | H | Me | all | O | 3-$CF_3$-Ph |
| B-17 | $CF_3$ | H | Me | $CH_2C\equiv CH$ | O | 3-$CF_3$-Ph |
| B-18 | $CF_3$ | H | Me | Et | O | 2-F-Ph |
| B-19 | $CF_3$ | H | Me | Me | O | 2,4-$F_2$-3-SMe-Ph |
| B-20 | $CF_3$ | H | Me | Me | O | 2-Me-4-OMe-Ph |
| B-21 | $CF_3$ | H | Me | Me | O | 2-F-4-OMe-Ph |

[TABLE 1-B]-continued

[Structure 46]

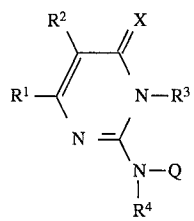

| Compound No. | R¹ | R² | R³ | R⁴ | X | Q |
|---|---|---|---|---|---|---|
| B-22 | $CF_3$ | H | Me | Me | O | Q26 |
| B-23 | $CF_3$ | H | Me | Me | O | 2,3-$Cl_2$-Ph |
| B-24 | $CF_3$ | H | Me | Me | O | 2-F-4-OEt-Ph |
| B-25 | $CF_3$ | H | Me | $CH_2Ph$-3$CF_3$ | O | 6-Me-Q23 |
| B-26 | $CF_3$ | H | Me | Me | O | 2,4-$F_2$-3-Cl-Ph |
| B-27 | $CF_3$ | H | Me | Me | O | 2-Cl-Ph |
| B-28 | i-Pro | H | Me | Me | O | 2-F-3-$CF_3$-Ph |
| B-29 | $CF_3$ | H | Me | Me | O | 2,4-$Cl_2$-Ph |
| B-30 | $CF_3$ | H | Me | Me | O | Q16 |
| B-31 | $CF_3$ | H | Me | Me | O | Q17 |
| B-32 | $CF_3$ | H | Me | Me | O | 2-F-3-Cl-Ph |
| B-33 | $CF_3$ | H | Me | Me | O | 2-Me-Q12 |
| B-34 | $CF_3$ | H | Me | Me | O | 2-Me-Q15 |
| B-35 | $CF_3$ | H | Me | Me | O | Q15 |
| B-36 | $CF_3$ | H | Me | Me | O | Q12 |
| B-37 | $CF_3$ | H | Me | Me | O | 3-Br-2,4-$F_2$-Ph |
| B-38 | $CF_3$ | H | Me | Me | O | 2,4-$F_2$-3-$CO_2$Me-Ph |
| B-39 | $CF_3$ | H | Me | Me | O | 1-$MeCO_2$-Q11 |
| B-40 | $CF_3$ | H | Me | Me | O | 2,3,4-$F_3$-Ph |
| B-41 | $CF_3$ | H | Me | Me | O | 2,4-$F_2$-3-Me-Ph |
| B-42 | $CF_3$ | H | Me | Me | O | 2,4-$F_2$-3-OMe-Ph |
| B-43 | $CF_3$ | H | Me | Me | O | 2-SMe-3-Cl-4-F-Ph |
| B-44 | $CF_3$ | H | Me | Me | O | 2,4,5-$F_3$-Ph |
| B-45 | $CF_3$ | H | Me | Me | O | 2,3,5,6-$F_4$-Ph |
| B-46 | $CF_3$ | H | Me | Me | O | 2-Me-4-$OCH_2$OMe-Ph |
| B-47 | $CF_3$ | H | Me | Me | O | 2-Me-4-OEt-Ph |
| B-48 | $CF_3$ | H | Me | Me | O | 2,3,5,6-$F_4$-4-Br-Ph |
| B-49 | $CF_3$ | H | Me | Me | O | 2-Br-3,4,6-$F_3$-Ph |
| B-50 | $CF_3$ | H | Me | Me | O | Q16 |

Q3, Q5, Q10, Q11, Q12, Q15, Q16, Q17, Q23, Q24, Q26, Q28, Q49 and Q56 represent the following formulae.

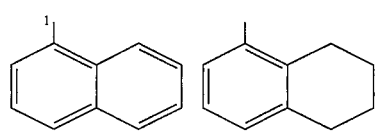

Q3      Q5

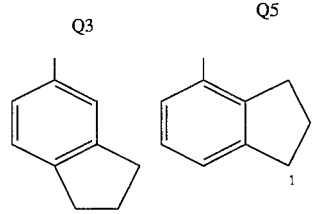

Q10      Q11

-continued

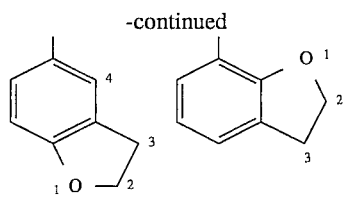

Q12      Q15

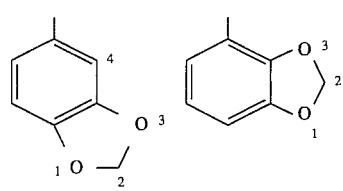

Q16      Q17

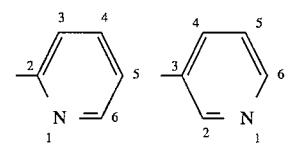

Q23      Q24

-continued

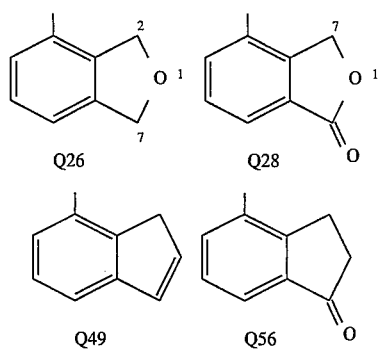

Me represents a methyl group, Et an ethyl group, Pro a propyl group, Bu a butyl group, Hex a hexyl group, all an allyl group, and Ph a phenyl group, and c represents cyclo, i iso, and t tertiary.

TABLE 2

| Compound No. | $^1$H-NMR δ (ppm) [Solvent] Physical properties |
|---|---|
| A-1 | 3.65(3H,s), 6.28(1H,s), 7.08~7.72(3H,m), 8.99(1H,br s) |
| | [d$_6$-DMSO] Melting point 168~170° C. |
| A-2 | 3.58(3H,s), 6.26(1H,s), 7.33(2H,d,J=10Hz), 7.64(2H,d,J=10Hz), 9.05(1H,br s) |
| | [d$_6$-DMSO] Melting point 238~239° C. |
| A-3 | 1.44(3H,s), 6.26(1H,s), 7.33(2H,d,J=10Hz), 6.88~7.38(3H,m), 8.08~8.45(1H,m) |
| | [CDCl$_3$] Melting point 148~149° C. |
| A-4 | 3.58(3H,s), 6.29(1H,s), 7.10~7.80(4H,m), 8.91(1H,br s) |
| | [d$_6$-DMSO] Melting point 177~179° C. |
| A-5 | 2.22(3H,s), 3.58(3H,s), 6.14(1H,s), 7.24(4H,br s), 8.74(1H,s) |
| | [d$_6$-DMSO] Melting point 138~139° C. |
| A-6 | 2.33(3H,s), 3.55(3H,s), 6.21(1H,s), 6.80~7.50(4H,m), 8.94(1H,s) |
| | [d$_6$-DMSO] Melting point 146~147° C. |
| A-7 | 2.29(3H,s), 3.54(3H,s), 6.17(1H,s), 7.10(2H,d,J=7Hz), 7.42(2H,d,J=7Hz), 8.97(1H,s) |
| | [d$_6$-DMSO] Melting point 211~213° C. |
| A-8 | 3.52(3H,s), 3.85(3H,s), 6.13(1H,s), 6.50~7.90(4H,m), 8.12(1H,s) |
| | [d$_6$-DMSO] Melting point 165~167° C. |
| A-9 | 3.56(3H,s), 3.78(3H,s), 6.24(1H,s), 6.50~6.92(1H,m), 7.03~7.53(3H,m), 8.95(1H,s) |
| | [d$_6$-DMSO] Melting point 202~204° C. |
| A-10 | 3.51(3H,s), 3.73(3H,s), 6.12(1H,s), 6.83(2H,d,J=9Hz), 7.43(2H,d,J=9Hz), 8.75(1H,s) |
| | [d$_6$-DMSO] Melting point 146~148° C. |
| A-11 | 3.60(3H,s), 6.36(1H,s), 7.09~7.53(4H,m), 8.25~8.50(1H,m) |
| | [CDCl$_3$] Melting point 117~118° C. |
| A-12 | 3.64(3H,s), 6.40(1H,s), 7.05~7.80(4H,m), 8.03~8.30(1H,m) |
| | [CDCl$_3$] Melting point 138~140° C. |
| A-13 | 3.62(3H,s), 6.34(1H,s), 7.35~7.53(2H,m), 7.85~8.10(2H,m), 8.98(1H,br s) |
| | [d$_6$-DMSO] Melting point 137~138° C. |
| A-14 | 3.60(3H,s), 6.30(1H,s), 7.05~7.91(4H,m), 8.40(1H,br s) |
| | [d$_6$-DMSO] Melting point 135~137° C. |
| A-15 | 3.64(3H,s), 6.35(1H,s), 7.54~8.00(4H,m), 9.13(1H,br s) |
| | [d$_6$-DMSO] Melting point 221~223° C. |
| A-16 | 3.64(3H,s), 6.22(1H,s), 7.19~7.63(3H,m), 9.47(1H,br s) |
| | [d$_6$-DMSO] Melting point 231~232° C. |
| A-17 | 3.20(6H,s), 3.59(3H,s), 6.10(1H,s), 7.12(3H,s), 8.60(1H, br s) |
| | [CDCl$_3$] Melting point 173~176° C. |
| A-18 | 1.19(3H,t,J=7Hz), 2.60(2H,q,J=7Hz), 3.50(3H,s), 6.10(1H,s), 7.26(4H,br s), 7.68(1H,s) |
| | [CDCl$_3$] Viscous liquid |
| A-19 | 3.62(3H,s), 6.35(1H,s), 6.72~7.73(4H,m), 8.36(1H br s) |

TABLE 2-continued

| Compound No. | $^1$H-NMR δ (ppm) [Solvent] Physical properties |
|---|---|
| A-20 | [CDCl$_3$] Melting point 120~122° C. |
| | 3.67(3H,s), 6.38(1H,s), 6.93(1H,br t, J=7Hz), 7.30(1H,br s), 7.44(1H,br t,J=7Hz), 7.85(1H,br d,J=7Hz), 8.22(1H,br d,J=7Hz) |
| A-21 | [CDCl$_3$] Melting point 106~108° C. |
| | 3.63(3H,s), 7.03~7.77(3H,m), 9.33(1H,br s) |
| A-22 | [d$_6$-DMSO] Melting point 205~206° C. |
| | 3.64(3H,s), 7.11~7.78(3H,m), 9.42(1H,br s) |
| A-23 | [d$_6$-DMSO] Melting point 204~206° C. |
| | 3.70(3H,s), 7.00~8.00(3H,m), 9.45(1H,br s) |
| A-24 | [d$_6$-DMSO] Melting point 193~194° C. |
| | 3.65(3H,s), 6.21(1H,s), 7.70~8.75(7H,m), 9.53(1H,br s) |
| A-25 | [d$_6$-DMSO] Melting point 153~155° C. |
| | 3.60(3H,s), 6.21(1H,s), 6.79~7.39(3H,m), 8.80(1H br s) |
| A-26 | [d$_6$-DMSO] Melting point 178~180° C. |
| | 2.71(3H,s), 3.60(3H,s), 6.26(1H,s), 7.00~8.20(4H,m), 8.70(1H,br s), |
| A-27 | [d$_6$-DMSO] Melting point 208~209° C. |
| | 2.16(3H,s), 2.27(3H,s), 3.42(3H,s), 6.04(1H,s), 6.79(1H,br s), 6.85~7.29(3H,m) |
| A-28 | [CDCl$_3$] Melting point 153~155° C. |
| | 2.18(3H,s), 3.45(3H,s), 3.70(3H,s), 6.08(1H,s), 6.45~6.80(3H,m), 7.05~7.35(1H,m) |
| A-29 | [CDCl$_3$] Melting point 139~141° C. |
| | 2.21(3H,s), 3.46(3H,s), 6.16(1H,s), 6.84~7.26(3H,m), 8.00(1H,d,J=8Hz) |
| A-30 | [CDCl$_3$] Melting point 141~143° C. |
| | 3.60(3H,s), 6.29(1H,s), 6.85~7.30(3H,m), 8.05~8.35(1H,m) |
| A-31 | [CDCl$_3$] Melting point 117~119° C. |
| | 2.22(3H,s), 3.58(3H,s), 6.17(1H,s), 6.81~7.41(3H,m), 8.57(1H,br s) |
| A-32 | [d$_6$-DMSO] Melting point 142~144° C. |
| | 2.36(3H,s), 3.56(3H,s), 6.17(1H,s), 6.85~7.55(3H,m), 8.77(1H,br s) |
| A-33 | [d$_6$-DMSO] Melting point 166~167° C. |
| | 3.61(3H,s), 6.27(1H,s), 7.20~7.89(3H,m), 8.47(1H,br s) |
| A-34 | [d$_6$-DMSO] Melting point 150~152° C. |
| | 3.56(3H,s), 3.85(6H,s), 6.21(1H,s), 6.89(1H,s), 6.97(1H,d,J=2Hz), 7.44(1H,d,J=2Hz), 8.70(1H,br s) |
| A-35 | [d$_6$-DMSO] Melting point 177~179° C. |
| | 2.06(3H,s), 2.26(3H,s), 3.51(3H,s), 6.06(1H,s), 7.05(3H,br s), 8.99(1H,br s) |
| A-36 | [d$_6$-DMSO] Melting point 168~170° C. |
| | 2.14(3H,s), 2.30(3H,s), 3.55(3H,s), 6.15(1H,s), 7.10(3H,br s), 9.04(1H,br s) |
| A-37 | [d$_6$-DMSO] Melting point 155~156° C. |
| | 3.69(3H,s), 6.25(1H,s), 7.27~7.78(3H,m), 9.19(1H,br s) |
| A-38 | [d$_6$-DMSO] Melting point 141~144° C. |
| | 3.60(3H,s), 6.26(1H,s), 7.17~7.80(3H,m), 9.10(1H,br s) |
| A-39 | [d$_6$-DMSO] Melting point 176~177° C. |
| | 2.21(6H,s), 3.51(3H,s), 6.21(1H,s), 6.95~7.80(3H,m), 9.00(1H,br s) |
| A-40 | [d$_6$-DMSO] Melting point 171~173° C. |
| | 2.24(3H,s), 3.56(3H,s), 6.21(1H,s), 7.34(3H,br s), 9.30(1H,br s) |
| A-41 | [d$_6$-DMSO] Melting point 187~190° C. |
| | 2.20(3H,s), 3.58(3H,s), 6.19(1H,s), 7.26~7.39(3H,m), 9.13(1H,br s) |
| A-42 | [d$_6$-DMSO] Melting point 178~180° C. |
| | 2.36(3H,s), 3.60(3H,s), 6.16(1H,s), 7.01~7.59(3H,m), 9.12(1H,br s) |
| A-43 | [d$_6$-DMSO] Melting point 136~137° C. |
| | 2.39(3H,s), 3.61(3H,s), 6.18(1H,s), 7.06~7.60(3H,m), 8.69(1H,br s) |
| A-44 | [d$_6$-DMSO] Melting point 133~135° C. |
| | 3.59(3H,s), 6.26(1H,s), 7.43(1H,d,J=9Hz), 7.90(1H,d,J=7Hz), 9.19(1H,br s) |
| A-45 | [d$_6$-DMSO] Melting point 166~167° C. |
| | 1.37(3H,t,J=7Hz), 3.53(3H,s), 4.03(2H,q,J=7Hz), 6.22(1H,s), 6.90(2H,d,J=9Hz), 7.48(2H,d,J=9Hz), 8.64(1H,br s) |

TABLE 2-continued

| Compound No. | $^1$H-NMR δ (ppm) [Solvent] Physical properties |
|---|---|
| A-46 | [d$_6$-DMSO]  Melting point 170~171° C.<br>1.29(6H,d,J=6Hz), 3.49(3H,s), 4.48(1H,qq,J=6Hz), 6.07(1H,s), 6.75(2H,d,J=9Hz), 7.34(2H,d,J=9Hz), 8.68(1H,br s) |
| A-47 | [d$_6$-DMSO]  Melting point 155~156° C.<br>3.59(3H,s), 6.27(1H,s), 7.24(2H,d,J=9Hz), 7.77(2H,d,J=9Hz), 9.06(1H,s) |
| A-48 | [d$_6$-DMSO]  Melting point 181~184° C.<br>3.55(3H,s), 3.77(6H,s), 6.28(1H,s), 6.30(1H,d,J=2Hz), 6.99(2H,d,J=2Hz), 9.01(1H,br s) |
| A-49 | [d$_6$-DMSO]  Melting point 170~172° C.<br>3.59(3H,s), 3.80(9H,s), 6.23(1H,s), 7.11(2H,s), 8.81(1H,br s) |
| A-50 | [d$_6$-DMSO]  Melting point 168~169° C.<br>3.64(3H,s), 6.27(1H,s), 6.81~7.71(3H,m), 8.79(1H,br s) |
| A-51 | [d$_6$-DMSO]  Melting point 147~149° C.<br>3.62(3H,s), 6.20(1H,s), 6.80~7.70(3H,m), 8.99(1H,br s) |
| A-52 | [d$_6$-DMSO]  Melting point 148~150° C.<br>3.51(3H,s), 3.81(6H,s), 6.11(1H,s), 6.34~6.64(3H,m), 8.40(1H,br s) |
| A-53 | [d$_6$-DMSO]  Melting point 126~128° C.<br>2.48(3H,s), 3.50(3H,s), 6.30(1H,s), 7.00~7.55(5H,m) |
| A-54 | [CDCl$_3$]  Melting point 130~132° C.<br>3.48(3H,s), 3.81(3H,s), 6.19(1H,s), 6.70~7.80(3H,m), 8.98(1H br s) |
| A-55 | [d$_6$-DMSO]  Melting point 168~169° C.<br>3.01(3H,s), 3.50(3H,s), 6.10(1H,s), 6.70~8.55(3H,m), 9.30(1H br s) |
| A-56 | [d$_6$-DMSO]  Melting point 216~219° C.<br>3.54(3H,s), 6.18(1H,s), 7.25~7.68(3H,m), 9.16(1H br s) |
| A-57 | [d$_6$-DMSO]  Melting point 187~189° C.<br>1.34(3H,t,J=7Hz), 3.52(3H,s), 4.26(2H,q,J=7Hz), 6.16(1H,s), 7.61(2H,d,J=8Hz), 7.88(2H,d,J=8Hz), 9.18(1H,br s) |
| A-58 | [d$_6$-DMSO]  Melting point 224~225° C.<br>3.61(3H,s), 6.27(1H,s), 7.23~7.96(4H,m), 9.61(1H,br s) |
| A-59 | [d$_6$-DMSO]  Melting point 174~176° C.<br>3.78(3H,s), 6.41(1H,s), 7.28~8.57(4H,m), 9.49(1H,br s) |
| A-60 | [d$_6$-DMSO]  Melting point 219~221° C.<br>3.59(3H,s), 6.35(1H,s), 7.68(2H,d,J=9Hz), 7.92(2H,d,J=9Hz), 9.48(1H, br s) |
| A-61 | [d$_6$-DMSO]  Melting point 280~281° C.<br>3.49(3H,s), 6.07(1H,s), 6.69~7.75(3H,m), 8.73(1H, br s) |
| A-63 | [d$_6$-DMSO]  Melting point 182~185° C.<br>3.61(3H,s), 6.27(1H,s), 7.69(1H,s), 7.83(1H,s), 9.12(1H, br s) |
| A-64 | [d$_6$-DMSO]  Melting point 197~199° C.<br>2.42(3H,s), 3.60(3H,s), 6.29(1H,s), 7.12~7.59(3H,m), 7.90~8.10(1H,m), 8.52(1H,br s) |
| A-65 | [d$_6$-DMSO]  Melting point 118~119° C.<br>2.41(3H,s), 3.51(3H,s), 6.12(1H,s), 6.73~7.01(1H,m), 7.07~7.25(1H,m), 7.43~7.61(2H,m), 8.65(1H,br s) |
| A-66 | [d$_6$-DMSO]  Melting point 195~197° C.<br>3.63(3H,s), 6.26(1H,s), 7.41~7.65(1H,m), 7.70~7.90(2H,m), 8.64(1H,br s) |
| A-67 | [d$_6$-DMSO]  Melting point 161~163° C.<br>3.57(3H,s), 6.12(1H,s), 6.86~7.65(3H,m), 8.65(1H,br s) |
| A-68 | [d$_6$-DMSO]  Melting point 117~119° C.<br>3.60(3H,s), 6.20(1H,s), 7.16~7.80(3H,m), 8.40(1H,br s) |
| A-69 | [d$_6$-DMSO]  Melting point 153~155° C.<br>3.65(3H,s), 6.30(1H,s), 7.20~7.80(3H,m), 8.98(1H,br s) |
| A-70 | [d$_6$-DMSO]  Melting point 206~208° C.<br>3.68(3H,s), 6.29(1H,s), 7.43~7.94(3H,m), 8.64(1H,br s) |
| A-71 | [d$_6$-DMSO]  Melting point 162~164° C.<br>3.65(3H,s), 6.21(1H,s), 7.42(1H,d,J=9Hz), 7.79(1H,d,J=9Hz), 8.50(1H,br s) |
| A-72 | [d$_6$-DMSO]  Melting point 170~172° C.<br>3.63(3H,s), 6.30(1H,s), 6.98~7.46(3H,m), 8.99(1H,br s) |
| A-73 | [d$_6$-DMSO]  Melting point 159~161° C.<br>2.31(3H,s), 3.60(3H,s), 6.20(1H,s), 6.95~7.65(3H,m), 8.93(1H,br s) |
| A-74 | [d$_6$-DMSO]  Melting point 182~184° C.<br>3.62(3H,s), 6.24(1H,s), 7.50(2H,s), 7.67(1H,s), 8.99(1H,br s) |
| A-75 | [d$_6$-DMSO]  Melting point 166~168° C.<br>2.11(3H,d,J=2Hz), 3.59(3H,s), 6.17(1H,s), 6.90~7.27(3H,m), 8.99(1H,br s) |
| A-76 | [d$_6$-DMSO]  Melting point 156~158° C.<br>3.61(3H,s), 3.99(3H,s), 6.25(1H,s), 6.85~7.19(2H,m), 7.42~7.69(1H,m), 8.49(1H,br s) |
| A-77 | [d$_6$-DMSO]  Melting point 167~169° C.<br>3.70(3H,s), 6.18(1H,s), 7.39-7.79(4H,m), 7.89~8.40(2H,m), 9.29(1H,br s) |
| A-78 | [d$_6$-DMSO]  Melting point 214~216° C.<br>1.50~2.01(4H,m), 2.41~3.03(4H,m), 3.53(3H,s), 6.11(1H,s), 7.02(3H,s), 8.62(1H,br s) |
| A-79 | [d$_6$-DMSO]  Melting point 168~170° C.<br>3.59(3H,s), 6.15(1H,s), 7.17~7.45(1H,m), 7.82~8.25(2H,m), 8.85(1H,br s) |
| A-80 | [d$_6$-DMSO]  Melting point 147~149° C.<br>3.65(3H,s), 6.40(1H,s), 7.55~8.70(3H,m), 9.25(1H,br s) |
| A-81 | [d$_6$-DMSO]  Melting point 171~174° C.<br>2.36(3H,s), 3.64(3H,s), 6.31(1H,s), 6.52~6.90(1H,m), 7.40~7.80(2H,m), 15.82(1H,br s) |
| A-82 | [d$_6$-DMSO]  Melting point 168~170° C.<br>2.27(3H,s), 3.57(3H,s), 6.24(1H,s), 7.58(2H,br s), 7.91(1H,br s), 12.00(1H,br s) |
| A-83 | [d$_6$-DMSO]  Melting point 156~158° C.<br>3.57(3H,s), 6.33(1H,s), 8.03(1H,d,J=2Hz), 8.39(1H,d,J=2Hz), 10.04(1H,br s) |
| A-84 | [d$_6$-DMSO]  Melting point 188~189° C.<br>2.18(3H,s), 3.57(3H,s), 6.17(1H,s), 6.91~7.15(1H,m), 7.40~7.70(2H,m), 8.76(1H,br s) |
| A-85 | [d$_6$-DMSO]  Melting point 192~194° C.<br>3.66(3H,s), 6.38(1H,s), 7.43(1H,br s), 7.45~7.83(2H,m), 8.62(1H,d,J=8Hz) |
| A-86 | [CDCl$_3$]  Melting point 134~135° C.<br>1.36(9H,s), 3.61(3H,s), 6.35(1H,s), 7.21~7.65(3H,m), 8.38(1H,d,J=8Hz) |
| A-87 | [CDCl$_3$]  Melting point 135~138° C.<br>3.57(3H,s), 3.92(3H,s), 6.24(1H,s), 6.85(1H,d,J=9Hz), 7.91(1H,dd,J=3Hz,9Hz), 8.39(1H,d,J=3Hz), 9.22(1H,br s) |
| A-88 | [d$_6$-DMSO]  Melting point 153~154° C.<br>4.22(3H,s), 7.16(1H,s), 7.42~8.13(7H,m), 9.85(1H,br s) |
| A-89 | [d$_6$-DMSO]  Melting point 214~217° C.<br>1.25(6H,d,J=8Hz), 3.03(1H,qq,J=8Hz,8Hz), 3.50(3H,s), 6.18(1H,s), 6.92(1H,br s), 7.18~7.51(4H,m) |
| A-90 | [CDCl$_3$]  Melting point 180~181° C.<br>0.93(3H,t,J=8Hz), 1.61(2H,tq,J=8Hz,8Hz), 2.56(2H,t,J=8Hz), 3.49(3H,s), 6.14(1H,s), 6.89~7.62(5H,m) |
| A-91 | [CDCl$_3$]  Melting point 132~134° C.<br>2.43(3H,s), 3.55(3H,s), 6.09(1H,s), 7.06~7.40(3H,m), 8.75(1H,br s) |
| A-92 | [d$_6$-DMSO]  Melting point 138~139° C.<br>2.51(3H,s), 3.58(3H,s), 6.13(1H,s), 7.25(3H,s), 9.17(1H,br s) |
| A-93 | [d$_6$-DMSO]  Melting point 156~158° C.<br>2.06(3H,s), 3.54(3H,s), 3.82(3H,s), 6.11(1H,s), 6.72~7.37(3H,m), 8.92(1H,br s) |
| A-94 | [d$_6$-DMSO]  Melting point 181~182° C.<br>2.34(3H,s), 3.58(3H,s), 6.17(1H,s), 6.95(1H,br t,J=7Hz), 7.33(1H,br d,J=7Hz) 7.81(1H,br d,J=7Hz), 9.10(1H,br s) |
| A-95 | [CDCl$_3$]  Melting point 194~196° C.<br>2.44(3H,s), 3.63(3H,s), 6.40(1H,s), 6.96~7.50(3H,m), 8.22~8.45(1H,m) |

TABLE 2-continued

| Compound No. | $^1$H-NMR δ (ppm) [Solvent] Physical properties |
|---|---|
| A-96 | [CDCl$_3$]    Melting point 137~139° C.<br>3.60(3H,s), 6.26(1H,s), 7.16~7.92(3H,m),<br>9.40(1H,br s) |
| A-97 | [d$_6$-DMSO]    Melting point 152~153° C.<br>3.59(3H,s), 6.29(1H,s), 7.21~7.87(4H,m),<br>9.00(1H,br s) |
| A-98 | [CDCl$_3$-d$_6$-DMSO]    Melting point 184~187° C.<br>3.60(3H,s), 3.99(3H,s), 6.40(1H,s), 7.14(2H,d,J=5Hz),<br>7.64(1H,br s), 8.41(1H,t,J=5Hz) |
| A-99 | [CDCl$_3$]    Melting point 123~125° C.<br>1.47(3H,t,J=7Hz), 3.58(3H,s), 4.20(2H,q,J=7Hz),<br>6.38(1H,s), 7.11(2H,d,J=5Hz), 7.71(1H,br s),<br>8.42(1H,t,J=5Hz) |
| A-100 | [CDCl$_3$]    Melting point 154~155° C.<br>2.34(3H,s), 3.59(3H,s), 3.81(3H,s), 6.37(1H,s),<br>6.82~7.26(2H,m), 7.45~7.78(1H,m),<br>8.15~8.39(1H,m) |
| A-101 | [CDCl$_3$]    Melting point 108° C.<br>1.41(3H,t,J=7Hz), 2.05(3H,s), 3.52(3H,s),<br>4.07(2H,q,J=7Hz), 6.11(1H,s), 6.69~7.31(3H,m),<br>8.76(1H,br s) |
| A-102 | [d$_6$-DMSO]    Melting point 163~165° C.<br>1.38(6H,d,J=6Hz), 2.02(3H,s), 3.54(3H,s),<br>4.54(1H,qq,J=6Hz), 6.10(1H,s), 6.70~7.33(3H,m),<br>8.80(1H,br s) |
| A-103 | [d$_6$-DMSO]    Melting point 166~167° C.<br>3.61(3H,s), 6.25(1H,s), 7.11~8.01(3H,m),<br>9.18(1H,br s) |
| A-104 | [d$_6$-DMSO]    Melting point 162~163° C.<br>1.07(3H,t,J=7Hz), 1.99(2H,m), 2.01(3H,s),<br>3.59(3H,s), 3.97(2H,t,J=7Hz), 6.20(1H,s),<br>6.70~7.46(3H,m), 8.22(1H,br s) |
| A-105 | [d$_6$-DMSO]    Melting point 132~134° C.<br>2.36(3H,s), 3.59(3H,s), 6.25(1H,s),<br>6.94(1H,t,J=8Hz), 7.30(1H,d,J=8Hz),<br>7.81(1H,d,J=8Hz), 8.89(1H,br s). |
| A-106 | [d$_6$-DMSO]    Melting point 160~162° C.<br>2.36(3H,s), 3.60(3H,s), 6.29(1H,s),<br>7.00~7.62(3H,m), 8.59(1H,br s) |
| A-107 | [d$_6$-DMSO]    Melting point 160~161° C.<br>2.19(3H,s), 4.67~4.98(2H,m), 4.99~5.40(2H,m),<br>5.62~6.05(1H,m), 6.10(1H,s), 7.05~7.38(3H,m),<br>8.93(1H,br s) |
| A-108 | [CDCl$_3$-d$_6$-DMSO]    Melting point 163~166° C.<br>4.71~4.97(2H,m), 5.20~5.61(2H,m),<br>5.67~5.92(1H,m), 6.37(1H,s), 7.10~7.85(5H,m) |
| A-109 | [CDCl$_3$]    Melting point 114~116° C.<br>2.20(3H,s), 4.70~4.92(2H,m), 5.14~5.58(2H,m),<br>5.69~5.94(1H,m), 6.30(1H,s), 6.74(1H,br s),<br>7.08~7.75(4H,m) |
| A-110 | [CDCl$_3$]    Melting point 114~116° C.<br>3.77(3H,s), 4.68~4.92(2H,m), 4.98~5.40(2H,m),<br>5.60~5.93(1H,m), 6.10(1H,s), 6.79(2H,d,J=9Hz),<br>7.33(2H,d,J=9Hz), 8.55(1H,br s) |
| A-111 | [CDCl$_3$-d$_6$-DMSO]    Melting point 166~168° C.<br>1.08(3H,t,J=7Hz), 2.29(2H,q,J=7Hz), 2.38(3H,s),<br>3.57(3H,s), 5.75(1H,s), 6.90(1H,t,J=8Hz),<br>7.32(1H,d,J=8Hz), 7.75(1H,d,J=8Hz), 8.25(1H,br s) |
| A-112 | [d$_6$-DMSO]    Melting point 171~172° C.<br>2.40(3H,s), 3.64(3H,s), 3.93(3H,s),<br>6.18(1H,s), 7.29~7.91(3H,m), 9.02(1H,br s) |
| A-113 | [d$_6$-DMSO]    Melting point 190~191° C.<br>2.22(3H,s), 2.70(6H,s), 3.55(3H,s),<br>6.32(1H,s), 6.50~7.30(4H,m) |
| A-114 | [CDCl$_3$]    Melting point 213~216° C.<br>1.10~2.40(10H,m), 2.23(3H,s), 4.32~4.90(1H,m),<br>6.11(1H,s), 7.11~7.36(3H,m), 8.71(1H,br s) |
| A-115 | [CDCl$_3$-d$_6$-DMSO]    Melting point 208~210° C.<br>1.15~2.40(10H,m), 4.65~5.38(1H,m), 6.29(1H,s),<br>6.90(1H,br s), 7.18~7.60(4H,m) |
| A-116 | [CDCl$_3$]    Melting point 175~177° C.<br>1.15~2.40(10H,m), 4.65~5.38(1H,m), 6.29(1H,s),<br>6.96(1H,br s), 7.20~7.84(4H,m) |
| A-117 | [CDCl$_3$]    Melting point 135~137° C.<br>1.15~2.40(10H,m), 2.29(3H,s), 4.68~5.40(1H,m),<br>6.25(1H,s), 6.68(1H,br s), 7.11~7.72(4H,m) |
| A-118 | [CDCl$_3$]    Melting point 183~184° C.<br>1.19~2.42(10H,m), 3.84(3H,s), 4.71~5.45(1H,m),<br>6.29(1H,s), 6.69~7.62(5H,m) |
| A-119 | [CDCl$_3$]    Melting point 167~169° C.<br>2.10(3H,s), 3.60(3H,s), 4.60(2H,d,J=4Hz),<br>5.15~5.65(2H,m), 5.80~6.38(1H,m), 6.15(1H,s),<br>6.72(7.32(3H,m), 8.80(1H,br s) |
| A-120 | [d$_6$-DMSO]    Melting point 150~151° C.<br>2.15(3H,s), 3.37(3H,s), 3.56(3H,s),<br>4.46(2H,s), 6.11(1H,s), 7.22(3H,br s),<br>8.91(1H,br s) |
| A-121 | [d$_6$-DMSO]    Melting point 185~186° C.<br>2.33(3H,d,J=1Hz), 3.61(3H,s), 6.17(1H,s),<br>7.26~7.70(3H,m), 8.91(1H,br s) |
| A-122 | [d$_6$-DMSO]    Melting point 157~158° C.<br>1.03(3H,t,J=7Hz), 1.50~2.20(2H,m), 2.25(3H,s),<br>4.15(2H,t,J=7Hz), 6.17(1H,s), 7.00~7.51(3H,m),<br>8.81(1H,br s) |
| A-123 | [CDCl$_3$]    Melting point 154~156° C.<br>1.07(3H,t,J=7Hz), 2.20(2H,q,J=7Hz), 2.32(3H,s),<br>3.54(3H,s), 5.70(1H,s), 7.00~7.59(3H,m),<br>8.45(1H,br s) |
| A-124 | [d$_6$-DMSO]    Melting point 169~171° C.<br>0.82(3H,t,J=8Hz), 1.28~1.70(2H,m),<br>2.20(2H,t,J=8Hz), 2.39(3H,s), 3.50(3H,s), 5.70(1H,s),<br>7.00(1H,t,J=8Hz),<br>7.31(1H,d,J=8Hz), 7.75(1H,d,J=8Hz), 8.68(1H,br s) |
| A-125 | [d$_6$-DMSO]    Melting point 164~166° C.<br>1.00(6H,d,J=7Hz), 2.30(3H,s), 2.41~2.62(1H,m),<br>3.52(3H,s), 5.65(1H,s), 7.08~7.60(3H,m),<br>8.65(1H,br s) |
| A-126 | [d$_6$-DMSO]    Melting point 187~188° C.<br>1.00(6H,d,J=7Hz), 2.30(3H,s), 2.40~2.70(1H,m),<br>3.55(3H,s), 5.69(1H,s), 6.91(1H,t,J=8Hz),<br>7.30(1H,d,J=8Hz), 7.76(1H,d,J=8Hz),<br>8.55(1H,br s) |
| A-127 | [d$_6$-DMSO]    Melting point 169~170° C.<br>1.97(3H,s), 3.54(3H,s), 5.10~5.70(2H,br s),<br>6.20(1H,s), 6.40~7.40(3H,m), 8.30(1H,br s) |
| A-128 | [d$_6$-DMSO]    Melting point 172~175° C.<br>2.23(3H,s), 2.93(3H,s), 3.57(3H,s),<br>6.14(1H,s), 7.10~7.80(3H,m), 8.97(2H,br s), |
| A-129 | [d$_6$-DMSO]    Melting point 230~232° C.<br>2.10(3H,s), 2.13(3H,s), 3.57(3H,s),<br>6.13(1H,s), 7.00~7.80(3H,m), 8.95(1H,br s),<br>9.20(1H,br s) |
| A-130 | [d$_6$-DMSO]    Melting point 211~213° C.<br>decomposed<br>1.06(9H,s), 2.33(3H,s), 3.53(3H,s),<br>5.87(1H,s), 6.86~7.60(4H,m) |
| A-131 | [CDCl$_3$]    Melting point 183~184° C.<br>0.99(9H,s), 2.31(3H,s), 3.49(3H,s),<br>5.73(1H,s), 6.90(1H,t,J=8Hz), 7.31(1H,d,J=8Hz),<br>7.78(1H,d,J=8Hz), 8.54(1H,br s) |
| A-132 | [d$_6$-DMSO]    Melting point 197~198° C.<br>2.24(3H,s), 3.31(3H,s), 3.50(3H,s),<br>3.94(2H,s), 5.83(1H,s), 7.05~7.61(3H,m),<br>8.77(1H,br s) |
| A-133 | [d$_6$-DMSO]    Melting point 198~200° C.<br>2.28(3H,s), 3.29(3H,s), 3.48(3H,s),<br>3.92(2H,s), 5.80(1H,s), 6.94(1H,t,J=8Hz),<br>7.30(1H,d,J=8Hz), 7.75(1H,d,J=8Hz), 8.74(1H,br s) |
| A-134 | [d$_6$-DMSO]    Melting point 197~198° C.<br>1.03(3H,t,J=7Hz), 1.50~2.20(2H,m),<br>4.14(2H,t,J=7Hz), 6.28(1H,s), 7.28~7.92(5H,m) |
| A-135 | [CDCl$_3$]    Melting point 129~131° C.<br>2.13(3H,s), 3.48(3H,s), 3.50(3H,s),<br>5.19(2H,s), 6.19(1H,s), 6.69~7.23(4H,m) |
| A-136 | [CDCl$_3$]    Melting point 117~120° C.<br>1.88~2.38(2H,m), 2.87(4H,t,J=7Hz),<br>3.42(3H,s), 6.18(1H,s), 6.68(1H,br s),<br>7.02~7.28(3H,m) |
| A-137 | [CDCl$_3$]    Melting point 181~182° C.<br>1.88~2.35(2H,m), 2.57~3.08(4H,m), |

TABLE 2-continued

| Compound No. | $^1$H-NMR δ (ppm) [Solvent] | Physical properties |
|---|---|---|
| | 3.41(3H,s), 6.10(1H,s), 6.77(1H,br s), 6.92~7.43(3H,m) [CDCl$_3$] | Melting point 161~162° C. |
| A-138 | 1.08(3H,t,J=7Hz), 2.30(2H,q,J=7Hz), 3.53(3H,s), 5.7*(1H,s), 6.90~7.90(3H,m), 8.70(1H,br s) [d$_6$-DMSO] | Melting point 149~150° C. |
| A-139 | 2.20(3H,s), 3.50(6H,br s), 5.11(1H,s), 6.99~7.62(3H,m), 8.70(1H,br s) [d$_6$-DMSO] | Melting point 188~189° C. |
| A-140 | 2.35(3H,s), 3.48(6H,br s), 5.12(1H,s), 6.90(1H,t,J=8Hz), 7.28(1H,d,J=8Hz), 7.78(1H,d,J=8Hz), 8.54(1H,br s) [d$_6$-DMSO] | Melting point 183.5~184.5° C. |
| A-141 | 0.45~0.80(4H,m), 1.30~1.80(1H,m), 2.20(3H,s), 3.42(3H,s), 5.63(1H,s), 6.80~7.50(3H,m), 8.45(1H,br s) [d$_6$-DMSO] | Melting point 178~179° C. |
| A-142 | 0.40~0.80(4H,m), 1.21~1.81(1H,m), 2.29(3H,s), 3.48(3H,s), 5.72(1H,s), 6.90(1H,t,J=8Hz), 7.23(1H,d,J=8Hz), 7.72(1H,d,J=8Hz), 8.59(1H,br s) [d$_6$-DMSO] | Melting point 180.5~181.5° C. |
| A-143 | 1.10(6H,d,J=6Hz), 2.31(3H,s), 3.50(3H,s), 4.36~4.81(1H,m), 5.10(1H,s), 7.01~7.61(3H,m), 8.56(1H,br s) [d$_6$-DMSO] | Melting point 176.5~177.5° C. |
| A-144 | 1.09(6H,d,J=6Hz), 2.33(3H,s), 3.48(3H,s), 4.35~4.81(1H,m), 5.06(1H,s), 6.99(1H,t,J=8Hz), 7.24(1H,d,J=8Hz), 7.74(1H,d,J=8Hz), 8.51(1H,br s) [d$_6$-DMSO] | Melting point 155.5~156.5° C. |
| A-145 | 1.14(3H,t,J=7Hz), 2.28(3H,s), 3.31(2H,q,J=7Hz), 3.52(3H,s), 3.98(2H,s), 5.85(1H,s), 6.91(1H,t,J=8Hz), 7.28(1H,d,J=8Hz), 7.75(1H,d,J=8Hz), 8.70(1H,br s) [d$_6$-DMSO] | Melting point 168.5~169.5° C. |
| A-146 | 1.17(3H,t,J=7Hz), 2.26(3H,s), 3.49(2H,q,J=7Hz), 3.53(3H,s), 4.00(2H,s), 5.91(1H,s), 7.00~7.60(3H,m), 8.62(1H,br s) [d$_6$-DMSO] | Melting point 174~175.5° C. |
| A-147 | 1.38(3H,t,J=7Hz), 2.35(3H,s), 4.28(2H,q,J=7Hz), 6.16(1H,s), 6.93~7.69(3H,m), 9.06(1H,br s) [d$_6$-DMSO] | Melting point 221~22° C. |
| A-148 | 1.31(3H,t,J=7Hz), 4.27(2H,q,J=7Hz), 6.24(1H,s), 7.15~7.39(2H,m), 7.50~7.92(2H,m), 9.05(1H,br s) [d$_6$-DMSO] | Melting point 188~189° C. |
| A-149 | 1.10(6H,d,J=7Hz), 2.30~2.86(1H,m), 3.59(3H,s), 5.81(1H,s), 7.12~7.52(2H,m), 7.81~8.33(2H,m) [d$_6$-DMSO] | Melting point 116~118° C. |
| A-150 | 2.18(3H,s), 3.52(3H,s), 3.82(3H,s), 4.68(2H,s), 6.25(1H,s), 6.50~7.30(4H,m) [CDCl$_3$] | Viscous oil |
| A-151 | 1.51(6H,s), 3.09(2H,s), 3.59(3H,s), 6.37(1H,s), 6.60~7.20(3H,m), 7.80~8.30(1H,br s) [CDCl$_3$] | Melting point 164~165° C. |
| A-152 | 3.60(3H,s), 5.32(2H,s), 6.28(1H,s), 7.50~8.00(3H,m), 9.25~9.55(1H,br,s) [CDCl$_3$-d$_6$-DMSO] | Melting point 268~270° C. |
| A-153 | 2.47(3H,s), 3.60(3H,s), 6.28(1H,s), 6.50~7.85(4H,m) [CDCl$_3$] | Melting point 183~184° C. |
| A-154 | 1.40(3H,t,J=7Hz), 2.18(3H,s), 3.50(3H,s), 4.03(2H,q,J=7Hz), 6.10(1H,s), 6.59~7.30(3H,m), 8.71(1H,br s) [CDCl$_3$-d$_6$-DMSO] | Melting point 153.5~154.5° C. |
| A-155 | 1.35(6H,d,J=8Hz), 2.20(3H,s), 3.59(3H,s), 4.30~4.80(1H,m), 6.19(1H,s), 6.56~7.30(3H,m), 8.50(1H,br s) [CDCl$_3$-d$_6$-DMSO] | Melting point 125~126° C. |
| A-156 | 3.54(3H,s), 3.77(3H,s), 6.16(1H,s), 6.50~6.87(2H,m), 7.20~7.60(1H,m), 8.43(1H,br s) [CDCl$_3$-d$_6$-DMSO] | Melting point 155.5~156.5° C. |
| A-157 | 3.53(3H,s), 4.90~5.20(4H,m), 6.25(1H,s), 6.90~7.40(5H,m) [CDCl$_3$] | Melting point 167~170° C. |
| A-158 | 2.19(3H,s), 3.48(3H,s), 3.55(3H,s), 5.16(2H,s), 6.13(1H,s), 6.75~7.31(3H,m), 8.52(1H,br s) [CDCl$_3$-d$_6$-DMSO] | Melting point 141.5~142.5° C. |
| A-159 | 2.19(3H,s), 3.56(3H,s), 4.42~4.66(2H,m), 5.12~5.60(2H,m), 5.78~6.35(1H,m), 6.14(1H,s), 6.64~6.90(2H,m), 7.05~7.30(1H,m), 8.48(1H,br s) [CDCl$_3$-d$_6$-DMSO] | Melting point 141~142° C. |
| A-160 | 1.49(3H,d,J=10Hz), 2.80~3.40(1H,m), 3.56(3H,s), 4.50~5.20(2H,m), 6.35(1H,s), 6.50~7.35(3H,m), 7.80~8.20(1H,br s), [CDCl$_3$] | Melting point 148~151° C. |
| A-161 | 1.47(3H,d,J=10Hz), 2.65~3.30(1H,m), 3.51(3H,s), 4.50~5.25(2H,m), 6.28(1H,s), 6.50~7.50(4H,m) [CDCl$_3$] | Melting point 147~150° C. |
| A-162 | 2.18(3H,s), 2.25~2.40(1H,m), 3.51(3H,s), 4.53~4.79(2H,m), 6.21(1H,s), 6.66~7.34(4H,m) [CDCl$_3$] | Melting point 107~108° C. |
| A-163 | 1.40(3H,t,J=7Hz), 3.56(3H,s), 4.05(2H,q,J=7Hz), 6.30(1H,s), 6.55~6.93(3H,m), 7.70~7.95(1H,m) [CDCl$_3$] | Melting point 133~134° C. |
| A-164 | 3.60(3H,s), 6.25(1H,s), 6.87~7.71(2H,m), 8.88(1H,br s), [CDCl$_3$-d$_6$-DMSO] | Melting point 133~134° C. |
| A-165 | 3.61(3H,s), 3.91(3H,s), 6.23(1H,s), 6.75~7.0(1H,m), 7.19~7.51(2H,m), 8.46(1H,br s) [CDCl$_3$-d$_6$-DMSO] | Melting point 169~170° C. |
| A-166 | 3.55(3H,s), 5.99(2H,s), 6.21(1H,s), 6.60~7.30(3H,m), 8.60~8.90(1H,br s) [CDCl$_3$-d$_6$-DMSO] | Melting point 184° C. |
| A-167 | 3.56(3H,s), 5.98(2H,s), 6.36(1H,s), 6.60~7.70(4H,m) [CDCl$_3$] | Melting point 151~154° C. |
| A-168 | 3.59(3H,s), 6.24(1H,s), 7.05~7.21(3H,m), 8.95(1H, br s) [CDCl$_3$-d$_6$-DMSO] | Melting point 161~162° C. |
| A-169 | 1.22(3H,t,J=7Hz), 2.13(3H,s), 3.52(3H,s), 3.74(2H,q,J=7Hz), 5.25(2H,s), 6.26(1H,s), 6.74(1H,br s), 6.96~7.32(3H,m) [CDCl$_3$] | Melting point 95~96° C. |
| A-170 | 2.08(3H,s), 3.41(3H,s), 3.57(3H,s), 3.63~3.89(2H,m), 4.02~4.27(2H,m), 6.13(1H,s), 6.70~7.35(3H,m), 8.90(1H,br s) [CDCl$_3$-d$_6$-DMSO] | Melting point 168~169° C. |
| A-171 | 2.16(3H,s), 2.46(3H,s), 3.55(3H,s), 6.11(1H,s), 7.00~7.33(3H,m), 9.03(1H,br s) [CDCl$_3$-d$_6$-DMSO] | Melting point 205~206° C. |
| A-172 | 2.57(3H,s), 3.14(3H,s), 3.61(3H,s), 6.19(1H,s), 7.40~7.78(2H,m), 7.91~8.18(1H,m), 9.20(1H,br s) [CDCl$_3$-d$_6$-DMSO] | Melting point 240~241° C. |
| A-173 | 2.18(3H,s), 2.65(3H,s), 3.56(3H,s), 6.15(1H,s), 7.32~7.98(3H,m), 9.24(1H,br s) [CDCl$_3$-d$_6$-DMSO] | Melting point 265~266° C. |
| A-174 | 3.29(2H,t,J=14Hz), 3.56(3H,s), 4.66(2H,t,J=14Hz), 6.37(1H,s), 6.72~7.15(3H,m), 8.00~8.25(1H,m) [CDCl$_3$] | Melting point 207~210° C. |
| A-175 | 3.21(2H,t,J=14.5Hz), 3.53(3H,s), 4.62(2H,t,J=14.5Hz), 6.31(1H,s), 6.68~7.38(4H,m) [CDCl$_3$] | Melting point 181~183° C. |
| A-176 | 2.00~3.20(4H,m), 3.56(3H,s), 3.79(3H,s), 6.10-6.30(1H,m), 6.31(1H,s), 7.00~7.80(4H,m) | |

TABLE 2-continued

| Compound No. | ¹H-NMR δ (ppm) [Solvent] | Physical properties |
|---|---|---|
| A-177 | [CDCl₃]<br>3.59(3H,s), 6.23(1H,s), 6.89~7.75(2H,m), 9.05(1H,br s) | Viscous liquid |
| A-178 | [CDCl₃-d₆-DMSO]<br>3.59(3H,s), 6.22(1H,s), 7.56(2H,s), 9.21(1H,br s) | Melting point 166~167° C. |
| A-179 | [CDCl₃-d₆-DMSO]<br>3.62(3H,s), 3.97(3H,s), 6.26(1H,s), 6.90~7.30(1H,m), 7.51~8.00(1H,m), 9.12(1H,br s) | Melting point 177~178° C. |
| A-180 | [CDCl₃-d₆-DMSO]<br>2.51(3H,s), 3.63(3H,s), 6.39(1H,s), 7.32(1H,d,J=9Hz) 7.33(1H,br s), 8.26(1H,d,J=9Hz) | Melting point 194~195° C. |
| A-181 | [CDCl₃]<br>3.32(2H,m), 3.55(3H,s), 6.32(1H,s), 6.40~7.00(3H,m), 7.10~7.50(3H,m) | Melting point 153~154° C. |
| A-182 | [CDCl₃]<br>2.00~2.90(4H,m), 3.24(1H,s), 3.55(3H,s), 5.00~5.25(1H,m), 6.14(1H,s), 7.00~7.40(3H,m), 8.95(1H,br s) | Melting point 152~155° C. |
| A-183 | [CDCl₃-d₆-DMSO]<br>2.00~3.00(4H,m), 2.04(3H,s), 3.56(3H,s), 6.00~6.30(1H,m), 6.25(1H,s), 6.90~7.70(4H,m) | Melting point 245~248° C. |
| A-184 | [CDCl₃]<br>3.60(3H,s), 6.25(1H,s), 6.80~7.60(2H,m), 9.00(1H,br s) | Viscous liquid |
| A-185 | [CDCl₃-d₆-DMSO]<br>2.20(3H,br s), 3.58(3H,s), 6.23(1H,s), 6.65~7.07(1H,m), 7.22~7.70(1h,m), 8.35(1H,br s) | Melting point 131~132° C. |
| A-186 | [CDCl₃-d₆-DMSO]<br>2.50~3.30(4H,m), 3.62(3H,s), 6.25(1H,s), 7.10~7.70(3H,m), 8.90(1H,br s) | Melting point 148~149° C. |
| A-187 | [CDCl₃]<br>3.62(3H,s), 6.34(1H,s), 6.50~7.90(5H,m) | Melting point 264~267° C. |
| A-188 |  | Melting point 186~189° C. |
| A-189 |  | Melting point 203~205° C. |
| A-190 |  | Melting point 168~170° C. |
| A-191 |  | Melting point 171~172° C. |
| A-192 | [CDCl₃]<br>3.59(3H,s), 4.08(3H,d,J=5Hz), 6.33(1H,s), 6.58~8.09(3H,m) | Melting point 211~213° C. |
| A-193 | [CDCl₃-d₆-DMSO]<br>3.57(3H,s), 4.00(3H,s), 6.36(1H,s), 7.00(1H,dd,J=15Hz), 7.45(1H,br s), 8.30(1H,dd,J=15Hz) | Melting point 150~151° C. |
| A-194 | [CDCl₃]<br>3.60(3H,s), 3.98(3H,s), 6.38(1H,s), 7.28(1H,d,J=15Hz), 7.55(1H,br s), 8.34(1H,d,J=15Hz) | Melting point 124~125° C. |
| A-195 | [CDCl₃]<br>3.58(3H,s), 3.83(3H,s), 3.91(3H,s), 6.18(1H,s), 6.81(1H,d,J=15Hz), 7.53(1H,d,J=15Hz), 8.55(1H,br s) | Melting point 147~148° C. |
| A-196 | [CDCl₃-d₆-DMSO]<br>2.42(3H,s), 3.67(3H,s), 6.42(1H,s), 7.00~7.40(1H,m), 8.45~8.71(1H,m), 8.83(1H,br s) | Melting point 160~161° C. |
| A-197 | [CDCl₃]<br>3.63(3H,s), 6.43(1H,s), 6.80~7.00(1H,br s), 7.60~8.25(1H,m) | Melting point 164~167° C. |
| A-198 | [CDCl₃]<br>3.61(3H,s), 6.42(1H,s), 6.70~7.30(2H,m), 8.00~8.45(1H,m) | Melting point 142~144° C. |
| A-199 | [CDCl₃]<br>3.64(3H,s), 6.32(1H,s), 6.95~7.50(1H,m), 8.70~9.30(1H,br s) | Melting point 131~134° C. |
| A-200 | [CDCl₃-d₆-DMSO] | Melting point 215~218° C. |
| A-201 |  | Melting point 185~188° C. |
| A-202 |  | Melting point 202~205° C. |
| A-203 |  | Melting point 175~178° C. |
| B-1 | 3.00(3H,s), 3.37(3H,s), 6.50(1H,s), | Melting point 153~154° C. |
| | 6.82~7.43(3H,m) | |
| B-2 | 1.23(3H,t,J=7Hz), 3.00(3H,s), 3.87(2H,q,J=7Hz), 6.49(1H,s), 6.79~7.39(3H,m) | Viscous oil |
| B-3 | [CDCl₃]<br>2.76(3H,s), 3.45(3H,s), 6.54(1H,s), 6.97~8.27(7H,m) | Viscous oil |
| B-4 | [CDCl₃]<br>1.32(3H,t,J=6Hz), 2.74(3H,s), 3.95(2H,q,J=6Hz), 6.52(1H,s), 6.90~8.26(7H,m) | Viscous oil |
| B-5 | [CDCl₃]<br>2.45(3H,s), 2.87(3H,s), 3.28(3H,s), 6.49(1H,s), 6.81(1H,dd,J=7Hz), 7.19(1H,t,J=7Hz), 7.40(1H,dd,J=7Hz) | Viscous oil |
| B-6 | [CDCl₃]<br>2.47(3H,s), 2.85(3H,s), 3.26(3H,s), 6.45(1H,s), 6.82(1H,dd,J=7Hz), 7.08(1H,t,J=7Hz), 7.56(1H,dd,J=7Hz) | Viscous oil |
| B-7 | [CDCl₃]<br>3.01(3H,s), 3.42(3H,s), 6.55(1H,s), 7.14~7.78(3H,m) | Viscous oil |
| B-8 | [CDCl₃]<br>3.02(3H,s), 3.49(3H,s), 6.56(1H,s), 6.90~7.75(4H,m) | Melting point 103.5~104.5° C. |
| B-9 | [CDCl₃]<br>1.30(3H,t,J=7Hz), 3.00(3H,s), 3.90(2H,q,J=7Hz), 6.53(1H,s), 7.10~7.69(3H,m) | Viscous oil |
| B-10 | [CDCl₃]<br>2.96(3H,s), 3.39(3H,s), 6.49(1H,s), 6.98~7.41(4H,m) | Viscous oil |
| B-11 | [CDCl₃]<br>3.00(3H,s), 3.37(3H,s), 6.45(1H,s), 6.60~7.25(3H,m) | Melting point 90~91° C. |
| B-12 | [CDCl₃]<br>0.92(3H,t,J=7Hz), 3.30(3H,s), 3.71(2H,q,J=7Hz), 6.43(1H,s), 6.70~7.30(4H,m) | Melting point 123~124° C. |
| B-13 | [CDCl₃]<br>1.28(3H,t,J=12Hz), 2.98(3H,s), 4.02(2H,q,J=12Hz), 6.55(1H,s), 6.90~7.70(4H,m) | Viscous oil |
| B-14 | [CDCl₃]<br>3.01(3H,s), 5.09(2H,s), 6.54(1H,s), 6.95~7.95(9H,m) | Viscous oil |
| B-15 | [CDCl₃]<br>1.32(6H,d,J=12Hz), 2.93(3H,s), 6.54(1H,s), 6.95~7.85(4H,m) | Melting point 85~88° C. |
| B-16 | [CDCl₃]<br>3.02(3H,s), 4.55(2H,d,J=10Hz), 4.90~5.35(2H,m), 5.60~6.30(1H,m), 6.55(1H,s), 6.90~7.60(4H,m) | Viscous oil |
| B-17 | [CDCl₃]<br>2.32(1H,t,J=4Hz), 3.03(3H,s), 4.84(2H,d,J=4Hz), 6.59(1H,s), 7.10~7.70(4H,m) | Viscous oil |
| B-18 | [CDCl₃]<br>1.25(3H,t,J=7Hz), 2.90(3H,s), 3.85(2H,q,J=7Hz), 5.86(1H,s), 6.70~7.30(4H,m) | Melting point 186~187° C. |
| B-19 | [CDCl₃]<br>2.54(3H,d,J=2Hz), 2.91(3H,s), 3.24(3H,s), 6.36(1H,s), 6.48~7.25(2H,m) | Melting point 116~118° C. |
| B-20 | [CDCl₃]<br>2.30(3H,s), 2.84(3H,s), 3.26(3H,s), 3.79(3H,s), 6.40(1H,s), 6.70~6.99(3H,m) | Melting point 99~100° C. |
| B-21 | [CDCl₃]<br>2.93(3H,s), 3.28(3H,s), 3.77(3H,s), 6.39(1H,s), 6.47~7.05(3H,m) | Melting point 76~77° C. |
| B-22 | [CDCl₃]<br>2.91(3H,s), 3.33(3H,s), 4.85~5.30(4H,m), 6.49(1H,s), 6.70~7.45(3H,m) | Viscous liquid |
| B-23 | [CDCl₃]<br>2.88(3H,s), 3.28(3H,s), 6.42(1H,s), 6.72~7.54(3H,m) | Melting point 101~102° C. |
| B-24 | [CDCl₃]<br>1.43(3H,t,J=7Hz), 2.98(3H,s), 3.32(3H,s), 4.05(2H,q,J=7Hz), 6.46(1H,s), 6.53~7.10(3H,m) | Viscous liquid |
| B-25 | [CDCl₃]<br>2.47(3H,s), 3.07(3H,s), 5.33(2H,s), | |

TABLE 2-continued

| Compound No. | $^1$H-NMR δ (ppm) [Solvent] | Physical properties |
|---|---|---|
| B-26 | 6.5(1H,s), 6.65~7.90(7H,m) [CDCl$_3$] | Viscous liquid |
| | 3.01(3H,s), 3.37(3H,s), 6.54(1H,s), 6.82~7.20(2H,m) [CDCl$_3$] | Melting point 81~82° C. |
| B-27 | 2.89(3H,s), 3.33(3H,s), 6.48(1H,s), 6.90~7.72(4H,m) [CDCl$_3$] | Melting point 74~76° C. |
| B-28 | 1.22(6H,d,J=7Hz), 2.47~2.94(1H,m), 3.03(3H,s), 3.33(3H,s), 6.08(1H,s), 7.01~7.66(3H,m) [CDCl$_3$] | Melting point 89~93° C. |
| B-29 | 2.90(3H,s), 3.27(3H,s), 6.40(1H,s), 6.75~7.50(3H,m) [CDCl$_3$] | Melting point 78~80° C. |
| B-30 | 3.03(3H,s), 3.37(3H,s), 6.03(2H,s), 6.30~6.85(4H,m) [CDCl$_3$] | Viscous liquid |
| B-31 | 3.02(3H,s), 3.40(3H,s), 5.99(2H,s), 6.25~7.00(4H,m) [CDCl$_3$] | Viscous liquid |
| B-32 | 3.00(3H,s), 3.39(3H,s), 6.53(1H,s), 6.75~7.60(3H,m) [CDCl$_3$] | Melting point 69.5~70.5° C. |
| B-33 | 1.48(3H,d,J=10Hz), 2.70~3.70(2H,m), 3.00(3H,s), 3.37(3H,s), 4.80~5.20(1H,m), 6.47(1H,s), 6.70~7.00(3H,s) [CDCl$_3$] | Melting point 128~131° C. |
| B-34 | 1.41(3H,d,J=10Hz), 2.80~3.70(2H,m), 2.94(3H,s), 3.36(3H,s), 4.70~5.20(1H,m), 6.44(1H,s), 6.70~7.20(3H,m) [CDCl$_3$] | Viscous liquid |
| B-35 | 2.94(3H,s), 3.28(2H,t,J=15Hz), 4.64(2H,t,J=15Hz), 6.46(1H,s), 6.70~7.30(3H,m) [CDCl$_3$] | Viscous liquid |
| B-36 | 2.99(3H,s), 3.20(2H,t,J=15Hz), 3.36(3H,s), 4.62(2H,t,J=15Hz), 6.45(1H,s), 6.70~6.90(3H,m) [CDCl$_3$] | Melting point 119~122° C. |
| B-37 | 2.97(3H,s), 3.32(3H,s), 6.43(1H,s), 6.38~6.62(2H,m) [CDCl$_3$] | Melting point 90~91° C. |
| B-38 | 3.02(3H,s), 3.37(3H,s), 4.00(3H,s), 6.51(1H,s), 6.95~7.45(2H,m) [CDCl$_3$] | Melting point 109~110° C. |
| B-39 | 1.60~2.90(4H,m), 2.09(3H,s), 2.87(3H,s), 3.37(3H,s), 5.90~6.20(1H,m), 6.47(1H,s), 6.70~7.40(3H,m) [CDCl$_3$] | Melting point 137~140° C. |
| B-40 | 3.02(3H,s), 3.36(3H,s), 6.52(1H,s), 6.61~7.30(2H,m) [CDCl$_3$] | Melting point 121~122° C. |
| B-41 | 2.25(3H,br s), 2.96(3H,s), 3.34(3H,s), 6.48(1H,s), 6.70~7.02(2H,m) [CDCl$_3$] | Melting point 90~91° C. |
| B-42 | 2.97(3H,s), 3.36(3H,s), 3.94(3H,d,J=5Hz), 6.44(1H,d), 6.78~7.11(2H,m) [CDCl$_3$] | Viscous liquid |
| B-43 | 2.47(3H,s), 2.95(3H,s), 3.37(3H,s), 6.48(1H,s), 6.80~7.50(2H,m) [CDCl$_3$] | Viscous liquid |
| B-44 | | |
| B-45 | | Melting point 88~90° C. |
| B-46 | | Melting point 138~141° C. |
| B-47 | | Melting point 74~77° C. |
| B-48 | | Melting point 108~111° C. |
| B-49 | 2.97(3H,s), 3.35(3H,s), 6.47(1H,s), 6.80~7.35(1H,m) [CDCl$_3$] | Melting point 149~152° C. |
| B-50 | | Viscous liquid |
| | | Melting point 114~117° C. |

Examples of the compounds of the present invention synthesized according to the above schemes or Examples 1 to 24 including Compounds A-1 to A-203 and B-1 to B-50 are shown in Table 3-1 and Table 3-2, but the present invention is not limited to these. Abbreviated words in Table 3-1 and Table 3-2 have the following meanings, respectively.

Me: a methyl group, Et: an ethyl group, Pro: a normal propyl group, i-Pro: an isopropyl group, Bu: normal butyl, i-Bu: an isobutyl group, s-Bu: a secondary butyl group, t-Bu: a tertiary butyl group, Pen: a normal pentyl group, Hex: a normal hexyl group, c-Pro: a cyclopropyl group, c-Pen: a cyclopentyl group, c-Hex: a cyclohexyl group, allyl: an allyl group and Ph: a phenyl group.

TABLE 3-1

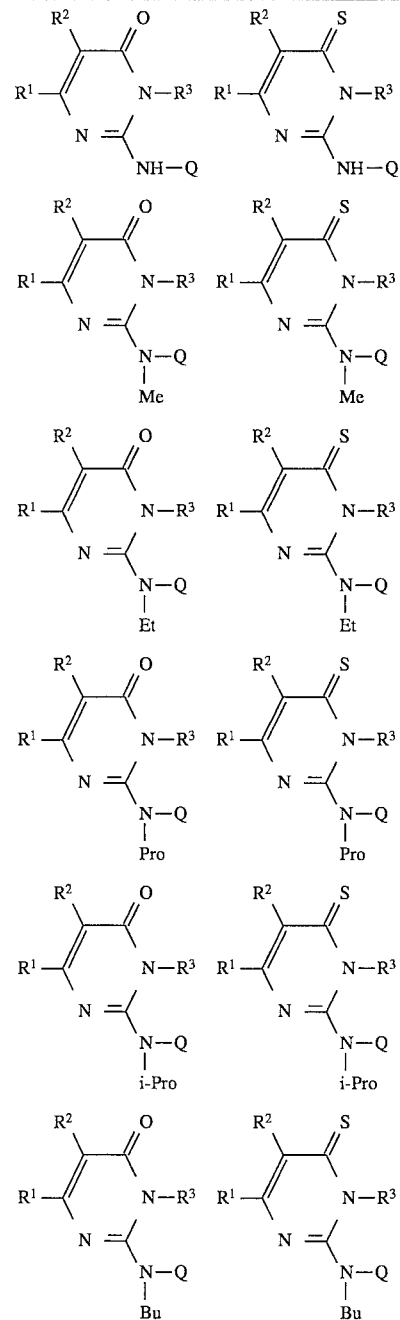

TABLE 3-1-continued

| Q | (C=O) | (C=S) |
|---|---|---|
| i-Bu | ✓ | ✓ |
| s-Bu | ✓ | ✓ |
| Pen | ✓ | ✓ |
| Hex | ✓ | ✓ |
| CH=CH$_2$ | ✓ | ✓ |
| CH$_2$CH=CH$_2$ | ✓ | ✓ |
| CH$_2$C≡CH | ✓ | ✓ |
| CH$_2$CH$_2$Cl | ✓ | ✓ |
| CH$_2$OMe | ✓ | ✓ |
| CHO | ✓ | ✓ |
| COMe | ✓ | ✓ |
| CO$_2$Me | ✓ | ✓ |
| CO$_2$Et | ✓ | ✓ |
| CONH$_2$ | ✓ | ✓ |

TABLE 3-1-continued

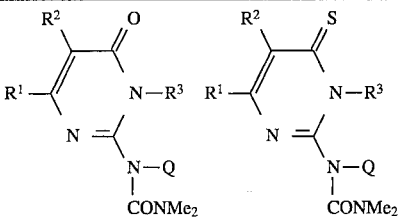
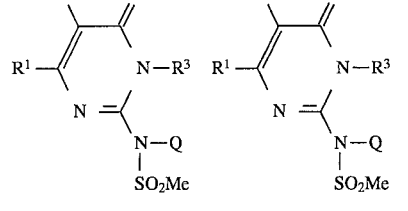
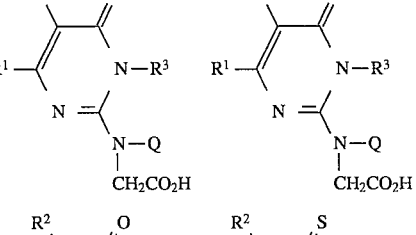
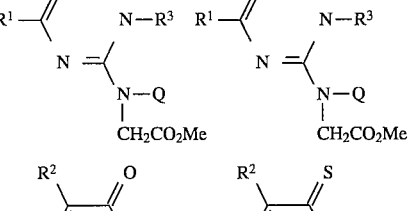
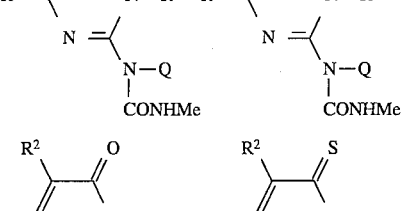
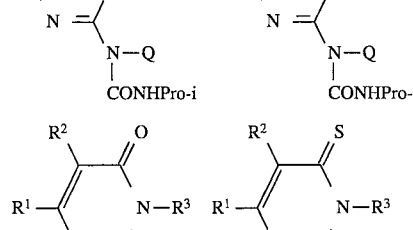
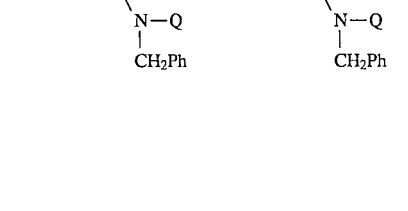
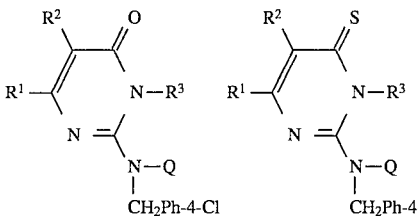
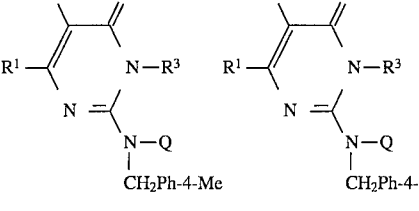
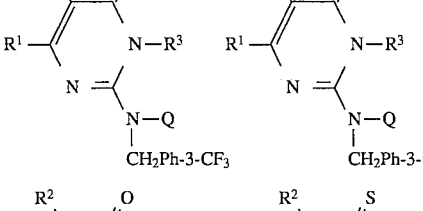
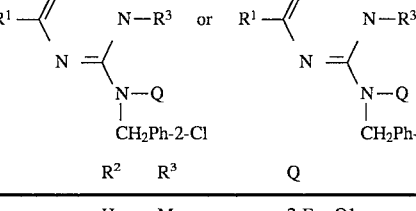
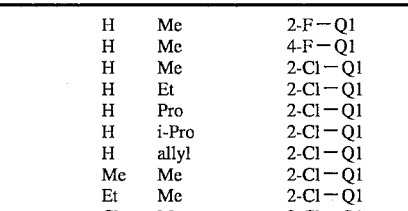
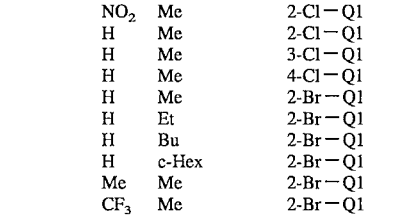
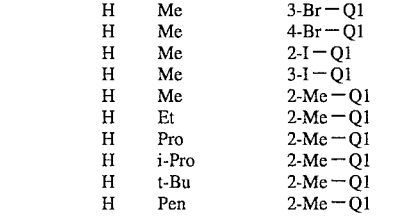
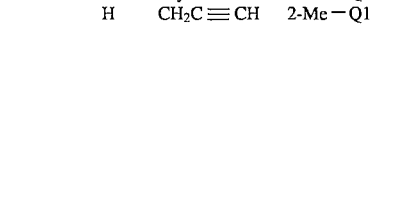
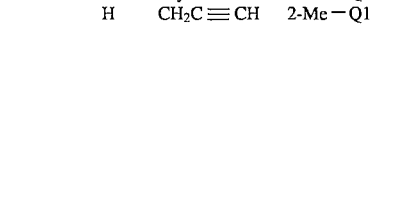

| $R^1$ | $R^2$ | $R^3$ | Q |
|---|---|---|---|
| $CF_3$ | H | Me | 2-F—Q1 |
| $CF_3$ | H | Me | 4-F—Q1 |
| $CF_3$ | H | Me | 2-Cl—Q1 |
| $CF_3$ | H | Et | 2-Cl—Q1 |
| $CF_3$ | H | Pro | 2-Cl—Q1 |
| $CF_3$ | H | i-Pro | 2-Cl—Q1 |
| $CF_3$ | H | allyl | 2-Cl—Q1 |
| $CF_3$ | Me | Me | 2-Cl—Q1 |
| $CF_3$ | Et | Me | 2-Cl—Q1 |
| $CF_3$ | Cl | Me | 2-Cl—Q1 |
| $CF_3$ | $NO_2$ | Me | 2-Cl—Q1 |
| $CF_3CF_2$ | H | Me | 2-Cl—Q1 |
| $CF_3$ | H | Me | 3-Cl—Q1 |
| $CF_3$ | H | Me | 4-Cl—Q1 |
| $CF_3$ | H | Me | 2-Br—Q1 |
| $CF_3$ | H | Et | 2-Br—Q1 |
| $CF_3$ | H | Bu | 2-Br—Q1 |
| $CF_3$ | H | c-Hex | 2-Br—Q1 |
| $CF_3$ | Me | Me | 2-Br—Q1 |
| $CF_3$ | $CF_3$ | Me | 2-Br—Q1 |
| $CF_3CF_2$ | H | Me | 2-Br—Q1 |
| $CF_3$ | H | Me | 3-Br—Q1 |
| $CF_3$ | H | Me | 4-Br—Q1 |
| $CF_3$ | H | Me | 2-I—Q1 |
| $CF_3$ | H | Me | 3-I—Q1 |
| $CF_3$ | H | Me | 2-Me—Q1 |
| $CF_3$ | H | Et | 2-Me—Q1 |
| $CF_3$ | H | Pro | 2-Me—Q1 |
| $CF_3$ | H | i-Pro | 2-Me—Q1 |
| $CF_3$ | H | t-Bu | 2-Me—Q1 |
| $CF_3$ | H | Pen | 2-Me—Q1 |
| $CF_3$ | H | allyl | 2-Me—Q1 |
| $CF_3$ | H | $CH_2C\equiv CH$ | 2-Me—Q1 |

TABLE 3-1-continued

| | | | |
|---|---|---|---|
| CF$_3$ | H | c-Pro | 2-Me—Q1 |
| CF$_3$ | H | NH$_2$ | 2-Me—Q1 |
| CF$_3$ | Me | Me | 2-Me—Q1 |
| CF$_3$ | F | Me | 2-Me—Q1 |
| CF$_3$ | Cl | Me | 2-Me—Q1 |
| CF$_3$ | Br | Me | 2-Me—Q1 |
| CF$_3$ | I | Me | 2-Me—Q1 |
| CF$_3$ | NO$_2$ | Me | 2-Me—Q1 |
| CF$_2$Cl | H | Me | 2-Me—Q1 |
| CF$_3$CF$_2$ | H | Me | 2-Me—Q1 |
| CF$_3$CF$_2$ | Me | Me | 2-Me—Q1 |
| CF$_3$CF$_2$CF$_2$ | H | Me | 2-Me—Q1 |
| CF$_3$ | H | Me | 3-Me—Q1 |
| CF$_3$ | H | Me | 4-Me—Q1 |
| CF$_3$ | H | Me | 2-Et—Q1 |
| CF$_3$ | H | Et | 2-Et—Q1 |
| CF$_3$ | H | Pro | 2-Et—Q1 |
| CF$_3$ | H | i-Bu | 2-Et—Q1 |
| CF$_3$ | H | s-Bu | 2-Et—Q1 |
| CF$_3$ | H | Hex | 2-Et—Q1 |
| CF$_3$ | Me | Me | 2-Et—Q1 |
| CF$_3$ | Pro | Me | 2-Et—Q1 |
| CF$_3$CF$_2$ | Me | Me | 2-Et—Q1 |
| CF$_3$ | H | Me | 3-Et—Q1 |
| CF$_3$ | H | Me | 4-Et—Q1 |
| CF$_3$ | H | Me | 2-Pro—Q1 |
| CF$_3$ | H | Me | 3-Pro—Q1 |
| CF$_3$ | H | Me | 4-Pro—Q1 |
| CF$_3$ | H | Me | 2-i-Pro—Q1 |
| CF$_3$ | H | Me | 3-i-Pro—Q1 |
| CF$_3$ | H | Me | 4-i-Pro—Q1 |
| CF$_3$ | H | Me | 3-Bu—Q1 |
| CF$_3$ | H | Me | 2-t-Bu—Q1 |
| CF$_3$ | H | Me | 2-OMe—Q1 |
| CF$_3$ | H | Et | 2-OMe—Q1 |
| CF$_3$ | H | Pro | 2-OMe—Q1 |
| CF$_3$ | H | i-Pro | 2-OMe—Q1 |
| CF$_3$ | H | Bu | 2-OMe—Q1 |
| CF$_3$ | H | i-Bu | 2-OMe—Q1 |
| CF$_3$ | H | t-Bu | 2-OMe—Q1 |
| CF$_3$ | H | allyl | 2-OMe—Q1 |
| CF$_3$ | H | c-Hex | 2-OMe—Q1 |
| CF$_3$ | H | NH$_2$ | 2-OMe—Q1 |
| CF$_3$ | Me | Me | 2-OMe—Q1 |
| CF$_3$ | Me | Pro | 2-OMe—Q1 |
| CF$_3$ | Et | Me | 2-OMe—Q1 |
| CF$_3$ | NO$_2$ | Me | 2-OMe—Q1 |
| CF$_3$ | Cl | Me | 2-OMe—Q1 |
| CF$_3$CF$_2$ | H | Me | 2-OMe—Q1 |
| CF$_3$CF$_2$ | Me | Me | 2-OMe—Q1 |
| CF$_3$CF$_2$CF$_2$ | H | Me | 2-OMe—Q1 |
| CF$_3$ | H | Me | 3-OMe—Q1 |
| CF$_3$ | H | Me | 4-OMe—Q1 |
| CF$_3$ | Cl | Me | 4-OMe—Q1 |
| CF$_3$ | H | Me | 2-OEt—Q1 |
| CF$_3$ | H | Me | 3-OEt—Q1 |
| CF$_3$ | H | Me | 4-OEt—Q1 |
| CF$_3$ | H | Me | 2-OPro—Q1 |
| CF$_3$ | H | Me | 3-OPro—Q1 |
| CF$_3$ | H | Me | 4-OPro—Q1 |
| CF$_3$ | H | Me | 2-Oi-Pro—Q1 |
| CF$_3$ | H | Me | 3-Oi-Pro—Q1 |
| CF$_3$ | H | Me | 4-Oi-Pro—Q1 |
| CF$_3$ | H | Me | 4-OBu—Q1 |
| CF$_3$ | H | Me | 4-Oi-Bu—Q1 |
| CF$_3$ | H | Me | 2-CF$_3$—Q1 |
| CF$_3$ | H | Me | 3-CF$_3$—Q1 |
| CF$_3$ | H | Pro | 3-CF$_3$—Q1 |
| CF$_3$ | Me | Me | 3-CF$_3$—Q1 |
| CF$_3$ | H | Me | 4-CF$_3$—Q1 |
| CF$_3$ | H | Me | 2-CH$_2$Cl—Q1 |
| CF$_3$ | H | Me | 3-CH$_2$Cl—Q1 |
| CF$_3$ | H | Me | 4-CH$_2$Cl—Q1 |
| CF$_3$ | H | Me | 2-CH$_2$CH$_2$Cl—Q1 |
| CF$_3$ | H | Me | 3-CH$_2$CH$_2$Cl—Q1 |
| CF$_3$ | H | Me | 2-OCF$_3$—Q1 |
| CF$_3$ | H | Me | 3-OCF$_3$—Q1 |
| CF$_3$ | H | Me | 4-OCF$_3$—Q1 |
| CF$_3$ | H | Me | 2-OCHF$_2$—Q1 |
| CF$_3$ | H | Me | 3-OCHF$_2$—Q1 |
| CF$_3$ | H | Me | 4-OCHF$_2$—Q1 |
| CF$_3$ | H | Me | 2-OCH$_2$CH$_2$Cl—Q1 |
| CF$_3$ | H | Me | 3-OCH$_2$CH$_2$Cl—Q1 |
| CF$_3$ | H | Me | 2-OCH$_2$CF$_3$—Q1 |
| CF$_3$ | H | Me | 3-OCH$_2$CF$_3$—Q1 |
| CF$_3$ | H | Me | 4-OCH$_2$CF$_3$—Q1 |
| CF$_3$ | H | Me | 2-SMe—Q1 |
| CF$_3$ | H | Me | 3-SMe—Q1 |
| CF$_3$ | H | Me | 4-SMe—Q1 |
| CF$_3$ | H | Me | 2-SEt—Q1 |
| CF$_3$ | H | Me | 3-SEt—Q1 |
| CF$_3$ | H | Me | 4-SEt—Q1 |
| CF$_3$ | H | Me | 2-SPro—Q1 |
| CF$_3$ | H | Me | 3-SBu—Q1 |
| CF$_3$ | H | Me | 2-SOMe—Q1 |
| CF$_3$ | H | Me | 4-SOMe—Q1 |
| CF$_3$ | H | Me | 4-SOEt—Q1 |
| CF$_3$ | H | Me | 4-SOPro—Q1 |
| CF$_3$ | H | Me | 4-SOBu—Q1 |
| CF$_3$ | H | Me | 2-SO$_2$Me—Q1 |
| CF$_3$ | H | Me | 3-SO$_2$Me—Q1 |
| CF$_3$ | H | Me | 4-SO$_2$Me—Q1 |
| CF$_3$ | H | Me | 4-SO$_2$Et—Q1 |
| CF$_3$ | H | Me | 4-SO$_2$Pro—Q1 |
| CF$_3$ | H | Me | 4-SO$_2$Bu—Q1 |
| CF$_3$ | H | Me | 2-COMe—Q1 |
| CF$_3$ | H | Me | 3-COMe—Q1 |
| CF$_3$ | H | Me | 2-COEt—Q1 |
| CF$_3$ | H | Me | 3-COEt—Q1 |
| CF$_3$ | H | Me | 4-COEt—Q1 |
| CF$_3$ | H | Me | 2-COi-Pro—Q1 |
| CF$_3$ | H | Me | 4-COBu—Q1 |
| CF$_3$ | H | Me | 2-CO$_2$Me—Q1 |
| CF$_3$ | H | Me | 3-CO$_2$Me—Q1 |
| CF$_3$ | H | Me | 4-CO$_2$Et—Q1 |
| CF$_3$ | H | Me | 2-CO$_2$Pro—Q1 |
| CF$_3$ | H | Me | 2-CN—Q1 |
| CF$_3$ | H | Me | 3-CN—Q1 |
| CF$_3$ | H | Me | 4-CN—Q1 |
| CF$_3$ | H | Me | 2-NH$_2$—Q1 |
| CF$_3$ | H | Me | 2-OH—Q1 |
| CF$_3$ | H | Me | 3-CO$_2$H—Q1 |
| CF$_3$ | H | Me | 2,3-F$_2$—Q1 |
| CF$_3$ | H | Et | 2,3-F$_2$—Q1 |
| CF$_3$ | H | Pro | 2,3-F$_2$—Q1 |
| CF$_3$ | H | i-Pro | 2,3-F$_2$—Q1 |
| CF$_3$ | Me | Me | 2,3-F$_2$—Q1 |
| CF$_3$ | Cl | Me | 2,3-F$_2$—Q1 |
| CF$_3$ | Br | Me | 2,3-F$_2$—Q1 |
| CF$_3$ | NO$_2$ | Me | 2,3-F$_2$—Q1 |
| CF$_3$CF$_2$ | H | Me | 2,3-F$_2$—Q1 |
| CF$_3$ | H | Me | 2,4-F$_2$—Q1 |
| CF$_3$ | H | Et | 2,4-F$_2$—Q1 |
| CF$_3$ | H | Pro | 2,4-F$_2$—Q1 |
| CF$_3$ | H | i-Pro | 2,4-F$_2$—Q1 |
| CF$_3$ | Me | Me | 2,4-F$_2$—Q1 |
| CF$_3$ | Cl | Me | 2,4-F$_2$—Q1 |
| CF$_3$ | Br | Me | 2,4-F$_2$—Q1 |
| CF$_3$ | NO$_2$ | Me | 2,4-F$_2$—Q1 |
| CF$_3$CF$_2$ | H | Me | 2,4-F$_2$—Q1 |
| CF$_3$ | H | Me | 2,5-F$_2$—Q1 |
| CF$_3$ | H | i-Pro | 2,5-F$_2$—Q1 |
| CF$_3$ | H | Me | 2,6-F$_2$—Q1 |
| CF$_3$ | H | Me | 3,4-F$_2$—Q1 |
| CF$_3$ | H | Me | 2-F-3-Cl—Q1 |
| CF$_3$ | Me | Me | 2-F-3-Cl—Q1 |
| CF$_3$CF$_2$ | H | Me | 2-F-3-Cl—Q1 |
| CF$_3$ | H | Me | 2-F-3-Br—Q1 |
| CF$_3$ | Me | Me | 2-F-3-Br—Q1 |
| CF$_3$CF$_2$ | H | Me | 2-F-3-Br—Q1 |
| CF$_3$ | H | Me | 2-F-3-I—Q1 |
| CF$_3$ | Me | Me | 2-F-3-I—Q1 |
| CF$_3$CF$_2$ | H | Me | 2-F-3-I—Q1 |
| CF$_3$ | H | Me | 2-F-3-Me—Q1 |
| CF$_3$ | Me | Me | 2-F-3-Me—Q1 |
| CF$_3$CF$_2$ | H | Me | 2-F-3-Me—Q1 |
| CF$_3$ | H | Me | 2-F-3-Et—Q1 |
| CF$_3$ | Me | Me | 2-F-3-Et—Q1 |

TABLE 3-1-continued

| | | | |
|---|---|---|---|
| CF$_3$CF$_2$ | H | Me | 2-F-3-Et—Q1 |
| CF$_3$ | H | Me | 2-F-3-i-Pro—Q1 |
| CF$_3$ | H | Me | 2-F-3-OMe—Q1 |
| CF$_3$ | Me | Me | 2-F-3-OMe—Q1 |
| CF$_3$CF$_2$ | H | Me | 2-F-3-OMe—Q1 |
| CF$_3$ | H | Me | 2-F-3-OEt—Q1 |
| CF$_3$ | Me | Me | 2-F-3-OEt—Q1 |
| CF$_3$CF$_2$ | H | Me | 2-F-3-OEt—Q1 |
| CF$_3$ | H | Me | 2-F-3-Oi-Pro—Q1 |
| CF$_3$ | H | Me | 2-F-4-Cl—Q1 |
| CF$_3$ | H | Et | 2-F-4-Cl—Q1 |
| CF$_3$ | Me | Me | 2-F-4-Cl—Q1 |
| CF$_3$ | Cl | Me | 2-F-4-Cl—Q1 |
| CF$_3$ | Br | Me | 2-F-4-Cl—Q1 |
| CF$_3$ | I | Me | 2-F-4-Cl—Q1 |
| CF$_3$CF$_2$ | H | Me | 2-F-4-Cl—Q1 |
| CF$_3$ | H | Me | 2-F-4-Br—Q1 |
| CF$_3$CF$_2$ | H | Me | 2-F-4-Br—Q1 |
| CF$_3$ | H | Me | 2-F-4-I—Q1 |
| CF$_3$ | H | Me | 2-F-4-Me—Q1 |
| CF$_3$ | H | Me | 2-F-4-OMe—Q1 |
| CF$_3$ | H | Me | 2,3-Cl$_2$—Q1 |
| CF$_3$ | H | Pro | 2,3-Cl$_2$—Q1 |
| CF$_3$ | H | i-Pro | 2,3-Cl$_2$—Q1 |
| CF$_3$ | H | allyl | 2,3-Cl$_2$—Q1 |
| CF$_3$ | H | t-Bu | 2,3-Cl$_2$—Q1 |
| CF$_3$ | H | c-Hex | 2,3-Cl$_2$—Q1 |
| CF$_3$ | H | NH$_2$ | 2,3-Cl$_2$—Q1 |
| CF$_3$ | Me | Me | 2,3-Cl$_2$—Q1 |
| CF$_3$ | Et | Me | 2,3-Cl$_2$—Q1 |
| CF$_3$ | Pro | Me | 2,3-Cl$_2$—Q1 |
| CF$_3$ | NO$_2$ | Me | 2,3-Cl$_2$—Q1 |
| CF$_3$CF$_2$ | H | Me | 2,3-Cl$_2$—Q1 |
| CF$_3$CF$_2$ | Me | Me | 2,3-Cl$_2$—Q1 |
| CF$_3$CF$_2$CF$_2$ | H | Me | 2,3-Cl$_2$—Q1 |
| CF$_3$CF$_2$CF$_2$CF$_2$ | H | Me | 2,3-Cl$_2$—Q1 |
| CF$_3$ | H | Me | 2,4-Cl$_2$—Q1 |
| CF$_3$ | H | NH$_2$ | 2,4-Cl$_2$—Q1 |
| CF$_3$ | Me | Me | 2,4-Cl$_2$—Q1 |
| CF$_3$CF$_2$ | H | Me | 2,4-Cl$_2$—Q1 |
| CF$_3$ | H | Me | 2,5-Cl$_2$—Q1 |
| CF$_3$ | H | Me | 2,6-Cl$_2$—Q1 |
| CF$_3$ | H | Me | 2-Cl-3-Br—Q1 |
| CF$_3$ | H | Et | 2-Cl-3-Br—Q1 |
| CF$_3$ | H | Pr | 2-Cl-3-Br—Q1 |
| CF$_3$ | H | i-Pro | 2-Cl-3-Br—Q1 |
| CF$_3$ | H | allyl | 2-Cl-3-Br—Q1 |
| CF$_3$ | Me | Me | 2-Cl-3-Br—Q1 |
| CF$_3$CF$_2$ | H | Me | 2-Cl-3-Br—Q1 |
| CF$_3$ | H | Me | 2-Cl-3-I—Q1 |
| CF$_3$ | H | NH$_2$ | 2-Cl-3-I—Q1 |
| CF$_3$ | Me | Me | 2-Cl-3-I—Q1 |
| CF$_3$CF$_2$ | H | Me | 2-Cl-3-I—Q1 |
| CF$_3$ | H | Me | 2-Cl-3-Me—Q1 |
| CF$_3$ | H | NH$_2$ | 2-Cl-3-Me—Q1 |
| CF$_3$ | Me | Me | 2-Cl-3-Me—Q1 |
| CF$_3$CF$_2$ | H | Me | 2-Cl-3-Me—Q1 |
| CF$_3$ | H | Me | 2-Cl-3-Et—Q1 |
| CF$_3$ | H | NH$_2$ | 2-Cl-3-Et—Q1 |
| CF$_3$ | Me | Me | 2-Cl-3-Et—Q1 |
| CF$_3$CF$_2$ | H | Me | 2-Cl-3-Et—Q1 |
| CF$_3$ | H | Me | 2-Cl-3-i-Pro—Q1 |
| CF$_3$ | H | NH$_2$ | 2-Cl-3-i-Pro—Q1 |
| CF$_3$ | Me | Me | 2-Cl-3-i-Pro—Q1 |
| CF$_3$CF$_2$ | H | Me | 2-Cl-3-i-Pro—Q1 |
| CF$_3$ | H | Me | 2-Cl-3-Pro—Q1 |
| CF$_3$ | H | Me | 2-Cl-3-Bu—Q1 |
| CF$_3$ | H | Me | 2-Cl-3-t-Bu—Q1 |
| CF$_3$ | H | Me | 2-Cl-3-OMe—Q1 |
| CF$_3$ | H | NH$_2$ | 2-Cl-3-OMe—Q1 |
| CF$_3$ | Me | Me | 2-Cl-3-OMe—Q1 |
| CF$_3$CF$_2$ | H | Me | 2-Cl-3-OMe—Q1 |
| CF$_3$ | H | Me | 2-Cl-3-OEt—Q1 |
| CF$_3$ | H | NH$_2$ | 2-Cl-3-OEt—Q1 |
| CF$_3$ | Me | Me | 2-Cl-3-OEt—Q1 |
| CF$_3$CF$_2$ | H | Me | 2-Cl-3-OEt—Q1 |
| CF$_3$ | H | Me | 2-Cl-3-Oi-Pro—Q1 |
| CF$_3$ | H | NH$_2$ | 2-Cl-3-Oi-Pro—Q1 |
| CF$_3$ | Me | Me | 2-Cl-3-Oi-Pro—Q1 |
| CF$_3$CF$_2$ | H | Me | 2-Cl-3-Oi-Pro—Q1 |
| CF$_3$ | H | Me | 2-Cl-3-OPro—Q1 |
| CF$_3$ | H | Me | 2-Cl-3-CF$_3$—Q1 |
| CF$_3$ | H | NH$_2$ | 2-Cl-3-CF$_3$—Q1 |
| CF$_3$ | Me | Me | 2-Cl-3-CF$_3$—Q1 |
| CF$_3$CF$_2$ | H | Me | 2-Cl-3-CF$_3$—Q1 |
| CF$_3$ | H | Me | 2-Cl-3-CH$_2$Cl—Q1 |
| CF$_3$ | H | Me | 2-Cl-3-CH$_2$Br—Q1 |
| CF$_3$ | H | Me | 2-Cl-3-OCF$_3$—Q1 |
| CF$_3$ | H | Me | 2-Cl-3-OCHF$_2$—Q1 |
| CF$_3$ | H | Me | 2-Cl-3-CH$_2$OMe—Q1 |
| CF$_3$ | H | Me | 2-Cl-3-CH$_2$OEt—Q1 |
| CF$_3$ | H | Me | 2-Cl-3-CH$_2$CH$_2$OMe—Q1 |
| CF$_3$ | H | Me | 2-Cl-3-CH$_2$CH$_2$OEt—Q1 |
| CF$_3$ | H | Me | 2-Cl-3-SMe—Q1 |
| CF$_3$ | H | Me | 2-Cl-3-SEt—Q1 |
| CF$_3$ | H | Me | 2-Cl-3-SOMe—Q1 |
| CF$_3$ | H | Me | 2-Cl-3-SO$_2$Me—Q1 |
| CF$_3$ | H | Me | 2-Cl-3-CN—Q1 |
| CF$_3$ | H | Me | 2-Cl-3-CO$_2$Me—Q1 |
| CF$_3$ | H | Me | 2-Cl-3-CO$_2$Et—Q1 |
| CF$_3$ | H | Me | 2-Cl-4-F—Q1 |
| CF$_3$ | H | Me | 2-Cl-4-Br—Q1 |
| CF$_3$ | H | Me | 2-Cl-4-I—Q1 |
| CF$_3$ | H | Me | 2-Cl-4-Me—Q1 |
| CF$_3$ | H | Me | 2-Cl-4-OMe—Q1 |
| CF$_3$ | H | Me | 2-Cl-4-OEt—Q1 |
| CF$_3$ | H | Me | 2-Cl-4-SMe—Q1 |
| CF$_3$ | H | Me | 2-Cl-5-Me—Q1 |
| CF$_3$ | H | Me | 2-Cl-4-OMe—Q1 |
| CF$_3$ | H | Me | 2,3-Br$_2$—Q1 |
| CF$_3$ | H | NH$_2$ | 2,3-Br$_2$—Q1 |
| CF$_3$ | Me | Me | 2,3-Br$_2$—Q1 |
| CF$_3$CF$_2$ | H | Me | 2,3-Br$_2$—Q1 |
| CF$_3$ | H | Me | 2,4-Br$_2$—Q1 |
| CF$_3$ | H | Me | 2-Br-3-Me—Q1 |
| CF$_3$CF$_2$ | H | Me | 2-Br-3-Me—Q1 |
| CF$_3$ | H | Me | 2-Br-3-Et—Q1 |
| CF$_3$CF$_2$ | H | Me | 2-Br-3-Et—Q1 |
| CF$_3$ | H | Me | 2-Br-3-OMe—Q1 |
| CF$_3$CF$_2$ | H | Me | 2-Br-3-OMe—Q1 |
| CF$_3$ | H | Me | 2-Br-3-OEt—Q1 |
| CF$_3$ | H | Me | 2-Br-3-CF$_3$—Q1 |
| CF$_3$ | H | Me | 2-Br-3-OCHF$_2$—Q1 |
| CF$_3$ | H | Me | 2-Br-3-OCF$_3$—Q1 |
| CF$_3$ | H | Me | 2-Br-3-CH$_2$OMe—Q1 |
| CF$_3$ | H | Me | 2-Br-3-SMe—Q1 |
| CF$_3$ | H | Me | 2-Br-3-CN—Q1 |
| CF$_3$ | H | Me | 2-Br-4-F—Q1 |
| CF$_3$ | H | Me | 2-Br-4-Cl—Q1 |
| CF$_3$ | H | Me | 2-Br-4-OMe—Q1 |
| CF$_3$ | H | Me | 2-Br-4-CF$_3$—Q1 |
| CF$_3$ | H | Me | 2-Br-4-t-Bu—Q1 |
| CF$_3$ | H | Me | 2-Br-4-Me—Q1 |
| CF$_3$ | H | Me | 2-I-3-Me—Q1 |
| CF$_3$ | H | Me | 2-I-3-Cl—Q1 |
| CF$_3$ | H | Me | 2-I-3-Br—Q1 |
| CF$_3$ | H | Me | 2-I-4-Cl—Q1 |
| CF$_3$ | H | Me | 2,3-Me$_2$—Q1 |
| CF$_3$ | H | Et | 2,3-Me$_2$—Q1 |
| CF$_3$ | H | Pro | 2,3-Me$_2$—Q1 |
| CF$_3$ | H | allyl | 2,3-Me$_2$—Q1 |
| CF$_3$ | H | i-Bu | 2,3-Me$_2$—Q1 |
| CF$_3$ | H | Hex | 2,3-Me$_2$—Q1 |
| CF$_3$ | H | NH$_2$ | 2,3-Me$_2$—Q1 |
| CF$_3$ | H | CH$_2$C≡CH | 2,3-Me$_2$—Q1 |
| CF$_3$ | Me | Me | 2,3-Me$_2$—Q1 |
| CF$_3$ | Et | Me | 2,3-Me$_2$—Q1 |
| CF$_3$ | Pro | Me | 2,3-Me$_2$—Q1 |
| CF$_3$ | i-Pro | Me | 2,3-Me$_2$—Q1 |
| CF$_3$ | CF$_3$ | Me | 2,3-Me$_2$—Q1 |
| CF$_3$ | NO$_2$ | Me | 2,3-Me$_2$—Q1 |
| CF$_3$ | Cl | Me | 2,3-Me$_2$—Q1 |
| CF$_3$ | Br | Me | 2,3-Me$_2$—Q1 |
| CF$_3$CF$_2$ | H | Me | 2,3-Me$_2$—Q1 |
| CF$_3$CF$_2$ | Me | Me | 2,3-Me$_2$—Q1 |

TABLE 3-1-continued

| | | | |
|---|---|---|---|
| CF$_3$ | H | Me | 2,4-Me$_2$—Q1 |
| CF$_3$ | H | Me | 2,5-Me$_2$—Q1 |
| CF$_3$ | H | Me | 2,6-Me$_2$—Q1 |
| CF$_3$ | H | Me | 3,4-Me$_2$—Q1 |
| CF$_3$ | H | Me | 2-Me-3-F—Q1 |
| CF$_3$ | Me | Me | 2-Me-3-F—Q1 |
| CF$_3$CF$_2$ | H | Me | 2-Me-3-F—Q1 |
| CF$_3$ | H | Me | 2-Me-3-Cl—Q1 |
| CF$_3$ | H | Et | 2-Me-3-Cl—Q1 |
| CF$_3$ | H | Pro | 2-Me-3-Cl—Q1 |
| CF$_3$ | H | i-Pr | 2-Me-3-Cl—Q1 |
| CF$_3$ | H | NH$_2$ | 2-Me-3-Cl—Q1 |
| CF$_3$ | H | c-Hex | 2-Me-3-Cl—Q1 |
| CF$_3$ | H | allyl | 2-Me-3-Cl—Q1 |
| CF$_3$ | Me | Me | 2-Me-3-Cl—Q1 |
| CF$_3$ | Et | Me | 2-Me-3-Cl—Q1 |
| CF$_3$ | Pro | Me | 2-Me-3-Cl—Q1 |
| CF$_3$ | F | Me | 2-Me-3-Cl—Q1 |
| CF$_3$ | Cl | Me | 2-Me-3-Cl—Q1 |
| CF$_3$ | Br | Me | 2-Me-3-Cl—Q1 |
| CF$_3$ | NO$_2$ | Me | 2-Me-3-Cl—Q1 |
| CF$_3$CF$_2$ | H | Me | 2-Me-3-Cl—Q1 |
| CF$_3$CF$_2$ | Cl | Me | 2-Me-3-Cl—Q1 |
| CF$_3$CF$_2$ | Me | Me | 2-Me-3-Cl—Q1 |
| CF$_3$CF$_2$ | NO$_2$ | Me | 2-Me-3-Cl—Q1 |
| CF$_3$CF$_2$CF$_2$ | H | Me | 2-Me-3-Cl—Q1 |
| CF$_3$ | H | Me | 2-Me-3-Br—Q1 |
| CF$_3$ | H | Et | 2-Me-3-Br—Q1 |
| CF$_3$ | H | Pro | 2-Me-3-Br—Q1 |
| CF$_3$ | H | i-Pro | 2-Me-3-Br—Q1 |
| CF$_3$ | H | Bu | 2-Me-3-Br—Q1 |
| CF$_3$ | H | s-Bu | 2-Me-3-Br—Q1 |
| CF$_3$ | H | t-Bu | 2-Me-3-Br—Q1 |
| CF$_3$ | H | Pen | 2-Me-3-Br—Q1 |
| CF$_3$ | H | Hex | 2-Me-3-Br—Q1 |
| CF$_3$ | H | c-Hex | 2-Me-3-Br—Q1 |
| CF$_3$ | H | allyl | 2-Me-3-Br—Q1 |
| CF$_3$ | H | NH$_2$ | 2-Me-3-Br—Q1 |
| CF$_3$ | Me | Me | 2-Me-3-Br—Q1 |
| CF$_3$ | Cl | Me | 2-Me-3-Br—Q1 |
| CF$_3$ | Et | Me | 2-Me-3-Br—Q1 |
| CF$_3$ | CF$_3$ | Me | 2-Me-3-Br—Q1 |
| CF$_3$ | NO$_2$ | Me | 2-Me-3-Br—Q1 |
| CF$_3$CF$_2$ | H | Me | 2-Me-3-Br—Q1 |
| CF$_3$CF$_2$ | H | NH$_2$ | 2-Me-3-Br—Q1 |
| CF$_3$CF$_2$ | Me | Me | 2-Me-3-Br—Q1 |
| CF$_3$CF$_2$CF$_2$ | H | Me | 2-Me-3-Br—Q1 |
| CF$_3$CF$_2$CF$_2$ | Me | Me | 2-Me-3-Br—Q1 |
| CF$_3$ | H | Me | 2-Me-3-I—Q1 |
| CF$_3$ | H | Et | 2-Me-3-I—Q1 |
| CF$_3$ | H | Pro | 2-Me-3-I—Q1 |
| CF$_3$ | H | i-Pro | 2-Me-3-I—Q1 |
| CF$_3$ | H | Bu | 2-Me-3-I—Q1 |
| CF$_3$ | H | s-Bu | 2-Me-3-I—Q1 |
| CF$_3$ | H | t-Bu | 2-Me-3-I—Q1 |
| CF$_3$ | H | Pen | 2-Me-3-I—Q1 |
| CF$_3$ | H | Hex | 2-Me-3-I—Q1 |
| CF$_3$ | H | c-Hex | 2-Me-3-I—Q1 |
| CF$_3$ | H | allyl | 2-Me-3-I—Q1 |
| CF$_3$ | H | NH$_2$ | 2-Me-3-I—Q1 |
| CF$_3$ | Me | Me | 2-Me-3-I—Q1 |
| CF$_3$ | Cl | Me | 2-Me-3-I—Q1 |
| CF$_3$ | Et | Me | 2-Me-3-I—Q1 |
| CF$_3$ | CF$_3$ | Me | 2-Me-3-I—Q1 |
| CF$_3$ | NO$_2$ | Me | 2-Me-3-I—Q1 |
| CF$_3$CF$_2$ | H | Me | 2-Me-3-I—Q1 |
| CF$_3$CF$_2$ | H | NH$_2$ | 2-Me-3-I—Q1 |
| CF$_3$CF$_2$ | Me | Me | 2-Me-3-I—Q1 |
| CF$_3$CF$_2$CF$_2$ | H | Me | 2-Me-3-I—Q1 |
| CF$_3$CF$_2$CF$_2$ | Me | Me | 2-Me-3-I—Q1 |
| CF$_3$CF$_2$CF$_2$CF$_2$ | H | Me | 2-Me-3-I—Q1 |
| CF$_3$ | H | Me | 2-Me-3-Et—Q1 |
| CF$_3$ | H | NH$_2$ | 2-Me-3-Et—Q1 |
| CF$_3$ | Me | Me | 2-Me-3-Et—Q1 |
| CF$_3$CF$_2$ | H | Me | 2-Me-3-Et—Q1 |
| CF$_3$ | H | Me | 2-Me-3-i-Pro—Q1 |
| CF$_3$ | H | NH$_2$ | 2-Me-3-i-Pro—Q1 |
| CF$_3$ | Me | Me | 2-Me-3-i-Pro—Q1 |
| CF$_3$CF$_2$ | H | Me | 2-Me-3-i-Pro—Q1 |
| CF$_3$ | H | Me | 2-Me-3-OMe—Q1 |
| CF$_3$ | H | Et | 2-Me-3-OMe—Q1 |
| CF$_3$ | H | Pro | 2-Me-3-OMe—Q1 |
| CF$_3$ | H | i-Pro | 2-Me-3-OMe—Q1 |
| CF$_3$ | H | NHz | 2-Me-3-OMe—Q1 |
| CF$_3$ | H | allyl | 2-Me-3-OMe—Q1 |
| CF$_3$ | Me | Me | 2-Me-3-OMe—Q1 |
| CF$_3$ | F | Me | 2-Me-3-OMe—Q1 |
| CF$_3$ | Br | Me | 2-Me-3-OMe—Q1 |
| CF$_3$ | NO$_2$ | Me | 2-Me-3-OMe—Q1 |
| CF$_3$CF$_2$ | H | Me | 2-Me-3-OMe—Q1 |
| CF$_3$CF$_2$ | Me | Me | 2-Me-3-OMe—Q1 |
| CF$_3$CF$_2$CF$_2$ | H | Me | 2-Me-3-OMe—Q1 |
| CF$_3$CF$_2$CF$_2$ | Me | Me | 2-Me-3-OMe—Q1 |
| CF$_3$ | H | Me | 2-Me-3-OEt—Q1 |
| CF$_3$ | H | Pro | 2-Me-3-OEt—Q1 |
| CF$_3$ | H | NH$_2$ | 2-Me-3-OEt—Q1 |
| CF$_3$ | Cl | Me | 2-Me-3-OEt—Q1 |
| CF$_3$ | NO$_2$ | Me | 2-Me-3-OEt—Q1 |
| CF$_3$CF$_2$ | H | Me | 2-Me-3-OEt—Q1 |
| CF$_3$CF$_2$ | Me | Me | 2-Me-3-OEt—Q1 |
| CF$_3$ | H | Me | 2-Me-3-OPro—Q1 |
| CF$_3$ | Me | Me | 2-Me-3-OPro—Q1 |
| CF$_3$CF$_2$ | H | Me | 2-Me-3-OPro—Q1 |
| CF$_3$ | H | Me | 2-Me-3-Oi-Pro—Q1 |
| CF$_3$ | Me | Me | 2-Me-3-Oi-Pro—Q1 |
| CF$_3$CF$_2$ | H | Me | 2-Me-3-Oi-Pro—Q1 |
| CF$_3$ | H | Me | 2-Me-3-OBu—Q1 |
| CF$_3$ | H | Me | 2-Me-3-Os—Bu—Q1 |
| CF$_3$ | H | Me | 2-Me-3-CF$_3$—Q1 |
| CF$_3$ | Me | Me | 2-Me-3-CF$_3$—Q1 |
| CF$_3$CF$_2$ | H | Me | 2-Me-3-CF$_3$—Q1 |
| CF$_3$ | H | Me | 2-Me-3-CH$_2$Cl—Q1 |
| CF$_3$ | H | Me | 2-Me-3-OCF$_3$—Q1 |
| CF$_3$ | H | Me | 2-Me-3-OCHF$_2$—Q1 |
| CF$_3$ | H | Me | 2-Me-3-OCH$_2$CF$_3$—Q1 |
| CF$_3$ | H | Me | 2-Me-3-CH$_2$OMe—Q1 |
| CF$_3$CF$_2$ | H | Me | 2-Me-3-CH$_2$OMe—Q1 |
| CF$_3$ | H | Me | 2-Me-3-CH$_2$OEt—Q1 |
| CF$_3$ | H | Me | 2-Me-3-CHCH$_2$OMe—Q1 |
| CF$_3$ | H | Me | 2-Me-3-SMe—Q1 |
| CF$_3$CF$_2$ | H | Me | 2-Me-3-SMe—Q1 |
| CF$_3$ | H | Me | 2-Me-3-SEt—Q1 |
| CF$_3$ | H | Me | 2-Me-3-SOMe—Q1 |
| CF$_3$ | H | Me | 2-Me-3-SOEt—Q1 |
| CF$_3$ | H | Me | 2-Me-3-SO$_2$Me—Q1 |
| CF$_3$ | H | Me | 2-Me-3-SO$_2$Et—Q1 |
| CF$_3$ | H | Me | 2-Me-3-CN—Q1 |
| CF$_3$ | H | Me | 2-Me-3-CO$_2$Me—Q1 |
| CF$_3$ | H | Me | 2-Me-3-CO$_2$Et—Q1 |
| CF$_3$ | H | Me | 2-Me-4-F—Q1 |
| CF$_3$ | H | Me | 2-Me-4-Cl—Q1 |
| CF$_3$ | H | Me | 2-Me-4-OMe—Q1 |
| CF$_3$ | H | Me | 2-Me-4-OEt—Q1 |
| CF$_3$ | H | Me | 2-Me-5-Cl—Q1 |
| CF$_3$ | H | Me | 2-Et-3-Cl—Q1 |
| CF$_3$ | Me | Me | 2-Et-3-Cl—Q1 |
| CF$_3$CF$_2$ | H | Me | 2-Et-3-Cl—Q1 |
| CF$_3$ | H | Me | 2-Et-3-Br—Q1 |
| CF$_3$ | Me | Me | 2-Et-3-Br—Q1 |
| CF$_3$CF$_2$ | H | Me | 2-Et-3-Br—Q1 |
| CF$_3$ | H | Me | 2-Et-3-I—Q1 |
| CF$_3$ | Me | Me | 2-Et-3-I—Q1 |
| CF$_3$CF$_2$ | H | Me | 2-Et-3-I—Q1 |
| CF$_3$ | H | Me | 2-Et-3-Me—Q1 |
| CF$_3$ | Me | Me | 2-Et-3-Me—Q1 |
| CF$_3$CF$_2$ | H | Me | 2-Et-3-Me—Q1 |
| CF$_3$ | H | Me | 2,3-Et$_2$—Q1 |
| CF$_3$ | Me | Me | 2,3-Et$_2$—Q1 |
| CF$_3$CF$_2$ | H | Me | 2,3-Et$_2$—Q1 |
| CF$_3$ | H | Me | 2-Et-3-OMe—Q1 |
| CF$_3$ | Me | Me | 2-Et-3-OMe—Q1 |
| CF$_3$CF$_2$ | H | Me | 2-Et-3-OMe—Q1 |
| CF$_3$ | H | Me | 2-Et-3-OEt—Q1 |
| CF$_3$ | H | Me | 2-Et-3-Oi-Pro—Q1 |
| CF$_3$ | H | Me | 2-Et-3-OCHF$_2$—Q1 |
| CF$_3$ | H | Me | 2-Et-3-CH$_2$OMe—Q1 |
| CF$_3$ | H | Me | 2-Et-3-SMe—Q1 |
| CF$_3$ | H | Me | 2-Et-3-SOMe—Q1 |

TABLE 3-1-continued

| | | | |
|---|---|---|---|
| CF$_3$ | H | Me | 2-Et-3-SO$_2$Me—Q1 |
| CF$_3$ | H | Me | 2-Et-3-CN—Q1 |
| CF$_3$ | H | Me | 2-Et-3-CO$_2$CH$_3$—Q1 |
| CF$_3$ | H | Me | 2,3-(OMe)$_2$—Q1 |
| CF$_3$ | H | Et | 2,3-(OMe)$_2$—Q1 |
| CF$_3$ | H | Pr | 2,3-(OMe)$_2$—Q1 |
| CF$_3$ | H | allyl | 2,3-(OMe)$_2$—Q1 |
| CF$_3$ | H | NH$_2$ | 2,3-(OMe)$_2$—Q1 |
| CF$_3$ | Me | Me | 2,3-(OMe)$_2$—Q1 |
| CF$_3$ | Br | Me | 2,3-(OMe)$_2$—Q1 |
| CF$_3$ | NO$_2$ | Me | 2,3-(OMe)$_2$—Q1 |
| CF$_3$CF$_2$ | H | Me | 2,3-(OMe)$_2$—Q1 |
| CF$_3$CF$_2$ | Me | Me | 2,3-(OMe)$_2$—Q1 |
| CF$_3$ | H | Me | 2,4-(OMe)$_2$—Q1 |
| CF$_3$ | H | Me | 3,4-(OMe)$_2$—Q1 |
| CF$_3$ | H | Me | 3,5-(OMe)$_2$—Q1 |
| CF$_3$ | H | Me | 2-OMe-3-F—Q1 |
| CF$_3$ | Me | Me | 2-OMe-3-F—Q1 |
| CF$_3$CF$_2$ | H | Me | 2-OMe-3-F—Q1 |
| CF$_3$ | H | Me | 2-OMe-3-Cl—Q1 |
| CF$_3$ | H | NH$_2$ | 2-OMe-3-Cl—Q1 |
| CF$_3$ | H | Et | 2-OMe-3-Cl—Q1 |
| CF$_3$ | H | Pro | 2-OMe-3-Cl—Q1 |
| CF$_3$ | H | i-Pro | 2-OMe-3-Cl—Q1 |
| CF$_3$ | H | t-Bu | 2-OMe-3-Cl—Q1 |
| CF$_3$ | H | allyl | 2-OMe-3-Cl—Q1 |
| CF$_3$ | H | c-Hex | 2-OMe-3-Cl—Q1 |
| CF$_3$ | H | Hex | 2-OMe-3-Cl—Q1 |
| CF$_3$ | Me | Me | 2-OMe-3-Cl—Q1 |
| CF$_3$ | Et | Me | 2-OMe-3-Cl—Q1 |
| CF$_3$ | F | Me | 2-OMe-3-Cl—Q1 |
| CF$_3$ | Cl | Me | 2-OMe-3-Cl—Q1 |
| CF$_3$ | Br | Me | 2-OMe-3-Cl—Q1 |
| CF$_3$ | NO$_2$ | Me | 2-OMe-3-Cl—Q1 |
| CF$_3$CF$_2$ | H | Me | 2-OMe-3-Cl—Q1 |
| CF$_3$CF$_2$ | H | NH$_2$ | 2-OMe-3-Cl—Q1 |
| CF$_3$CF$_2$ | Me | Me | 2-OMe-3-Cl—Q1 |
| CF$_3$CF$_2$CF$_2$ | H | Me | 2-OMe-3-Cl—Q1 |
| CF$_3$CF$_2$CF$_2$ | Me | Me | 2-OMe-3-Cl—Q1 |
| CF$_3$ | H | Me | 2-OMe-3-Br—Q1 |
| CF$_3$ | H | Et | 2-OMe-3-Br—Q1 |
| CF$_3$ | H | Pr | 2-OMe-3-Br—Q1 |
| CF$_3$ | H | NH$_2$ | 2-OMe-3-Br—Q1 |
| CF$_3$ | Me | Me | 2-OMe-3-Br—Q1 |
| CF$_3$ | NO$_2$ | Me | 2-OMe-3-Br—Q1 |
| CF$_3$CF$_2$ | H | Me | 2-OMe-3-Br—Q1 |
| CF$_3$ | H | Me | 2-OMe-3-I—Q1 |
| CF$_3$ | H | NH$_2$ | 2-OMe-3-I—Q1 |
| CF$_3$ | Me | Me | 2-OMe-3-I—Q1 |
| CF$_3$CF$_2$ | H | Me | 2-OMe-3-I—Q1 |
| CF$_3$CF$_2$ | Me | Me | 2-OMe-3-I—Q1 |
| CF$_3$ | H | Me | 2-OMe-3-Me—Q1 |
| CF$_3$ | Me | Me | 2-OMe-3-Me—Q1 |
| CF$_3$CF$_2$ | H | Me | 2-OMe-3-Me—Q1 |
| CF$_3$ | H | Me | 2-OMe-3-Et—Q1 |
| CF$_3$ | Me | Me | 2-OMe-3-Et—Q1 |
| CF$_3$CF$_2$ | H | Me | 2-OMe-3-Et—Q1 |
| CF$_3$ | H | Me | 2-OMe-3-Pro—Q1 |
| CF$_3$ | H | Me | 2-OMe-3-i-Pro—Q1 |
| CF$_3$ | H | Me | 2-OMe-3-OEt—Q1 |
| CF$_3$ | H | Me | 2-OMe-3-CF$_3$—Q1 |
| CF$_3$ | H | Me | 2-OMe-3-CH$_2$Cl—Q1 |
| CF$_3$ | H | Me | 2-OMe-3-OCF$_3$—Q1 |
| CF$_3$ | H | Me | 2-OMe-3-OCHF$_2$—Q1 |
| CF$_3$ | H | Me | 2-OMe-3-CH$_2$OMe—Q1 |
| CF$_3$ | H | Me | 2-OMe-3-CN—Q1 |
| CF$_3$ | H | Me | 2-OMe-3-CO$_2$Me—Q1 |
| CF$_3$ | H | Me | 2-OMe-4-Cl—Q1 |
| CF$_3$ | H | Me | 2-OMe-4-Br—Q1 |
| CF$_3$ | H | Me | 2-OMe-4-I—Q1 |
| CF$_3$ | H | Me | 2-OMe-4-CF$_3$—Q1 |
| CF$_3$ | H | Me | 2-OMe-4-CO$_2$Me—Q1 |
| CF$_3$ | H | Me | 2-OMe-5-Cl—Q1 |
| CF$_3$ | H | Me | 2-OMe-5-Br—Q1 |
| CF$_3$ | H | Me | 2-OMe-5-I—Q1 |
| CF$_3$ | H | Me | 2-OMe-5-CN—Q1 |
| CF$_3$ | H | Me | 2-OMe-5-Me—Q1 |
| CF$_3$ | H | Me | 2-OMe-5-CO$_2$Me—Q1 |
| CF$_3$ | H | Me | 2-OMe-6-Cl—Q1 |

TABLE 3-1-continued

| | | | |
|---|---|---|---|
| CF$_3$ | H | Me | 2-OMe-6-Me—Q1 |
| CF$_3$ | H | Me | 2-OEt-3-F—Q1 |
| CF$_3$ | H | Me | 2-OEt-3-Cl—Q1 |
| CF$_3$ | H | Me | 2-OEt-3-Br—Q1 |
| CF$_3$ | H | Me | 2-OEt-3-I—Q1 |
| CF$_3$ | H | Me | 2-OEt-3-Me—Q1 |
| CF$_3$ | H | Me | 2-OEt-3-Et—Q1 |
| CF$_3$ | H | Me | 2-OEt-3-CF$_3$—Q1 |
| CF$_3$ | H | Me | 2-OEt-4-Cl—Q1 |
| CF$_3$ | H | Me | 2-CF$_3$-3-Cl—Q1 |
| CF$_3$ | H | Me | 2-CF$_3$-3-Br—Q1 |
| CF$_3$ | H | Me | 2-OCHF$_2$-3-Me—Q1 |
| CF$_3$ | Me | Me | 2-OCHF$_2$-3-Me—Q1 |
| CF$_3$CF$_2$ | H | Me | 2-OCHF$_2$-3-Me—Q1 |
| CF$_3$ | H | Me | 2-OCHF$_2$-3-F—Q1 |
| CF$_3$ | H | Me | 2-OCHF$_2$-3-Cl—Q1 |
| CF$_3$ | H | Me | 2-OCHF$_2$-3-Br—Q1 |
| CF$_3$ | H | Me | 2-OCHF$_2$-3-I—Q1 |
| CF$_3$ | H | Me | 2-OCF$_3$-3-Me—Q1 |
| CF$_3$ | H | Me | 2-OCF$_3$-3-Cl—Q1 |
| CF$_3$ | H | Me | 2-CH$_2$Cl-3-Cl—Q1 |
| CF$_3$ | H | Me | 2-CH$_2$Cl-3-Br—Q1 |
| CF$_3$ | H | Me | 2-CH$_2$Cl-3-I—Q1 |
| CF$_3$ | H | Me | 2-CH$_2$OMe-3-Cl—Q1 |
| CF$_3$ | H | Me | 2-SMe-3-Me—Q1 |
| CF$_3$ | H | Me | 2-SMe-3-Cl—Q1 |
| CF$_3$ | Me | Me | 2-SMe-3-Cl—Q1 |
| CF$_3$ | H | Me | 2-SOMe-3-Cl—Q1 |
| CF$_3$ | H | Me | 2-SO$_2$Me-3-Cl—Q1 |
| CF$_3$ | H | Me | 2-CN-3-Me—Q1 |
| CF$_3$ | H | Me | 2-CN-3-Cl—Q1 |
| CF$_3$ | H | Me | 2-CN-3-OMe—Q1 |
| CF$_3$ | H | Me | 2-CN-3-SMe—Q1 |
| CF$_3$ | H | Me | 2,3,4-F$_3$—Q1 |
| CF$_3$ | H | Me | 2,3,4-Cl$_3$—Q1 |
| CF$_3$ | H | Me | 2,4,5-Cl$_3$—Q1 |
| CF$_3$ | H | Me | 2-F-4-Cl-5-Br—Q1 |
| CF$_3$ | H | Me | 3,4,5-(OMe)$_3$—Q1 |
| CF$_3$ | H | Me | 2,3,4-Me$_3$—Q1 |
| CF$_3$ | H | Me | 2,3,4,6-F$_4$—Q1 |
| CF$_3$ | H | Me | 2,3,5,6-F$_4$—Q1 |
| CF$_3$ | H | Me | 2,3,4,5,6-F$_5$—Q1 |
| CF$_3$ | H | Me | Q2 |
| CF$_3$ | H | Me | 1-Me—Q2 |
| CF$_3$ | H | Me | Q3 |
| CF$_3$ | H | Me | 4-Cl—Q3 |
| CF$_3$ | H | Me | 4-Me—Q3 |
| CF$_3$ | H | Me | 4-OMe—Q3 |
| CF$_3$ | H | Me | Q4 |
| CF$_3$ | H | Me | 1-Me—Q4 |
| CF$_3$ | H | Me | 1-Cl—Q4 |
| CF$_3$ | H | Me | 1-OMe—Q4 |
| CF$_3$ | H | Me | Q5 |
| CF$_3$ | Me | Me | Q5 |
| CF$_3$CF$_2$ | H | Me | Q5 |
| CF$_3$ | H | Me | 4-Cl—Q5 |
| CF$_3$ | H | Me | 4-Me—Q5 |
| CF$_3$ | H | Me | 4-OMe—Q5 |
| CF$_3$ | H | Me | Q6 |
| CF$_3$ | H | Me | 7-Cl—Q6 |
| CF$_3$ | H | Me | 7-Me—Q6 |
| CF$_3$ | H | Me | 7-OMe—Q6 |
| CF$_3$ | H | Me | Q7 |
| CF$_3$ | H | Me | 4-Cl—Q7 |
| CF$_3$ | H | Me | 4-Me—Q7 |
| CF$_3$ | H | Me | 4-OMe—Q7 |
| CF$_3$ | H | Me | Q8 |
| CF$_3$ | Me | Me | Q8 |
| CF$_3$CF$_2$ | H | Me | Q8 |
| CF$_3$ | H | Me | 7-Cl—Q8 |
| CF$_3$ | H | Me | 7-Me—Q8 |
| CF$_3$ | H | Me | 7-OMe—Q8 |
| CF$_3$ | H | Me | Q9 |
| CF$_3$ | Me | Me | Q9 |
| CF$_3$CF$_2$ | H | Me | Q9 |
| CF$_3$ | H | Me | 4-Cl—Q9 |
| CF$_3$ | H | Me | 4-Me—Q9 |
| CF$_3$ | H | Me | 4-OMe—Q9 |
| CF$_3$ | H | Me | Q10 |

TABLE 3-1-continued

| | | | |
|---|---|---|---|
| CF$_3$ | H | Me | 4-Cl—Q10 |
| CF$_3$ | H | Me | 4-Me—Q10 |
| CF$_3$ | H | Me | 4-OMe—Q10 |
| CF$_3$ | H | Me | Q11 |
| CF$_3$ | H | Et | Q11 |
| CF$_3$ | H | Pr | Q11 |
| CF$_3$ | H | NH$_2$ | Q11 |
| CF$_3$ | Me | Me | Q11 |
| CF$_3$ | Cl | Me | Q11 |
| CF$_3$ | NO$_2$ | Me | Q11 |
| CF$_3$CF$_2$ | H | Me | Q11 |
| CF$_3$CF$_2$ | Me | Me | Q11 |
| CF$_3$CF$_2$CF$_2$ | H | Me | Q11 |
| CF$_3$ | H | Me | 7-Cl—Q11 |
| CF$_3$ | H | Me | 7-Me—Q11 |
| CF$_3$ | H | Me | 7-OMe—Q11 |
| CF$_3$ | H | Me | Q12 |
| CF$_3$ | H | Me | 4-Me—Q12 |
| CF$_3$ | H | Me | 4-Cl—Q12 |
| CF$_3$ | H | Me | 4-OMe—Q12 |
| CF$_3$ | H | Me | Q13 |
| CF$_3$ | H | Me | 7-Cl—Q13 |
| CF$_3$ | H | Me | 7-Me—Q13 |
| CF$_3$ | H | Me | 7-OMe—Q13 |
| CF$_3$ | H | Me | Q14 |
| CF$_3$CF$_2$ | H | Me | Q14 |
| CF$_3$ | H | Me | 7-Cl—Q14 |
| CF$_3$ | H | Me | 7-Me—Q14 |
| CF$_3$ | H | Me | 7-OMe—Q14 |
| CF$_3$ | H | Me | Q15 |
| CF$_3$ | Me | Me | Q15 |
| CF$_3$CF$_2$ | H | Me | Q15 |
| CF$_3$ | H | Me | 4-Cl—Q15 |
| CF$_3$ | H | Me | 4-Me—Q15 |
| CF$_3$ | H | Me | 4-OMe—Q15 |
| CF$_3$ | H | Me | Q16 |
| CF$_3$ | H | Me | 4-Cl—Q16 |
| CF$_3$ | H | Me | Q17 |
| CF$_3$ | H | Me | 7-Cl—Q17 |
| CF$_3$ | H | Me | Q18 |
| CF$_3$ | H | Me | 5-Cl—Q18 |
| CF$_3$ | H | Me | 5-Me—Q18 |
| CF$_3$ | H | Me | Q19 |
| CF$_3$ | H | Me | 8-Me—Q19 |
| CF$_3$ | H | Me | 8-Cl—Q19 |
| CF$_3$ | H | Me | Q20 |
| CF$_3$ | H | Me | 2-Me—Q20 |
| CF$_3$ | H | Me | Q21 |
| CF$_3$ | H | Me | Q22 |
| CF$_3$ | H | Me | 5-Cl—Q22 |
| CF$_3$ | H | Me | 5-Me—Q22 |
| CF$_3$ | H | Me | Q23 |
| CF$_3$ | H | Me | 3-Cl—Q23 |
| CF$_3$ | H | Me | 3-Br—Q23 |
| CF$_3$ | H | Me | 3-Me—Q23 |
| CF$_3$ | H | Me | 3-OMe—Q23 |
| CF$_3$ | H | Me | 4-Me—Q23 |
| CF$_3$ | H | Me | 5-Cl—Q23 |
| CF$_3$ | H | Me | 5-Me—Q23 |
| CF$_3$ | H | Me | 3,4-Cl$_2$—Q23 |
| CF$_3$ | H | Me | 3-Cl-4-OMe—Q23 |
| CF$_3$ | H | Me | 3,5-Cl$_2$—Q23 |
| CF$_3$ | H | Me | 3,5-Br$_2$—Q23 |
| CF$_3$ | H | Me | 3-Cl-5-CF$_3$—Q23 |
| CF$_3$ | H | Me | 3,5-Cl$_2$-4-OMe—Q23 |
| CF$_3$ | H | Me | Q24 |
| CF$_3$ | H | Me | 2-Cl—Q24 |
| CF$_3$ | H | Me | 2-OMe—Q24 |
| CF$_3$ | H | Me | 2-CF$_3$—Q24 |
| CF$_3$ | H | Me | 2-Br—Q24 |
| CF$_3$ | H | Me | 4-Cl-5-CF$_3$—Q24 |
| CF$_3$ | H | Me | 4-Me—Q24 |
| CF$_3$ | H | Me | 4-OMe—Q24 |
| CF$_3$ | H | Me | 4-Me-5-Cl—Q24 |
| CF$_3$ | H | Me | 4-OMe-5-Cl—Q24 |
| CF$_3$ | H | Me | Q25 |
| CF$_3$ | H | Me | 2,3-Cl$_2$—Q25 |
| CF$_3$ | H | Me | 2-OMe-3-Cl—Q25 |
| CF$_3$ | H | Me | 2-F-3-CF$_3$—Q1 |

TABLE 3-1-continued

| | | | |
|---|---|---|---|
| CF$_3$ | H | Et | 3-CF$_3$—Q1 |
| CF$_3$ | H | NH2 | 3-CF$_3$—Q1 |
| CF$_3$ | H | allyl | 3-CF$_3$—Q1 |
| CF$_3$ | H | c-Hex | 3-CF$_3$—Q1 |
| CF$_3$ | H | c-Hex | 4-Cl—Q1 |
| CF$_3$ | H | c-Hex | 2-Me—Q1 |
| CF$_3$ | H | allyl | 4-OMe—Q1 |
| CF$_3$ | H | Me | 2-NMe$_2$—Q1 |
| CF$_3$ | H | Me | 2-OCH$_2$OMe—Q1 |
| CF$_3$ | H | Me | 3-Oallyl-Q1 |
| CF$_3$ | H | Me | 3-OCH$_2$OMe—Q1 |
| CF$_3$ | H | Me | 3-OCH$_2$OEt—Q1 |
| CF$_3$ | H | Me | 3-OCH$_2$CH$_2$OMe—Q1 |
| CF$_3$ | H | Me | 3-OCH$_2$C≡CH—Q1 |
| CF$_3$ | H | Me | 3-OCH$_2$CO$_2$Me—Q1 |
| CF$_3$ | H | Me | 3-OCHMeCO$_2$Me—Q1 |
| CF$_3$ | H | Me | 4-OCH$_2$OMe—Q1 |
| CF$_3$ | H | Me | 4-OCH$_2$OEt—Q1 |
| CF$_3$ | H | Me | 4-OCH$_2$CH$_2$OMe—Q1 |
| CF$_3$ | H | Me | 4-OCH$_2$CO$_2$Me—Q1 |
| CF$_3$ | H | Me | 2-Me-3-NH$_2$—Q1 |
| CF$_3$ | H | Me | 2-Me-3-NMe$_2$—Q1 |
| CF$_3$ | H | Me | 2-Me-3-NEt$_2$—Q1 |
| CF$_3$ | H | Me | 2-Me-3-NHSO$_2$Me—Q1 |
| CF$_3$ | H | Me | 2-Me-3-NHCOMe$_2$—Q1 |
| CF$_3$ | H | Me | 2-Me-3-OH—Q1 |
| CF$_3$ | H | Me | 2-Me-3-OC(O)Me—Q1 |
| CF$_3$ | H | Me | 2-Me-3-Oallyl-Q1 |
| CF$_3$ | H | Me | 2-Me-3-OCH$_2$C≡CH—Q1 |
| CF$_3$ | H | Me | 2-Me-3-OCH$_2$OMe—Q1 |
| CF$_3$ | H | Me | 2-Me-3-OCH$_2$OEt—Q1 |
| CF$_3$ | H | Me | 2-Me-3-OCH$_2$CH$_2$OMe—Q1 |
| CF$_3$ | H | Me | 2-Me-3-OCH$_2$CH$_2$OEt—Q1 |
| CF$_3$ | H | Me | 2-Me-3-OCH$_2$CO$_2$H—Q1 |
| CF$_3$ | H | Me | 2-Me-3-OCH$_2$CO$_2$Me—Q1 |
| CF$_3$ | H | Me | 2-Me-3-OCH$_2$CO$_2$Et—Q1 |
| CF$_3$ | H | Me | 2-Me-3-OCHMeCO$_2$H—Q1 |
| CF$_3$ | H | Me | 2-Me-3-OCHMeCO$_2$Me—Q1 |
| CF$_3$ | H | Me | 2-Me-3-OCHMeCO$_2$Et—Q1 |
| CF$_3$ | H | Me | 2-Me-4-OCH$_2$OMe—Q1 |
| CF$_3$ | H | Me | 2-Me-4-OCH$_2$OEt—Q1 |
| CF$_3$ | H | Me | 2-Me-4-OCH$_2$CH$_2$OMe—Q1 |
| CF$_3$ | H | Me | 2-Me-4-OCH$_2$CO$_2$H—Q1 |
| CF$_3$ | H | Me | 2-Me-4-OCH$_2$CO$_2$Me—Q1 |
| CF$_3$ | H | Me | 2-Me-4-OCHMeCO$_2$Me—Q1 |
| CF$_3$ | H | Me | 2-Me-4-OCHMeCO$_2$Et—Q1 |
| CF$_3$ | H | Me | 2-Me-3-allyl-Q1 |
| CF$_3$ | H | Me | 2-Me-3-CH$_2$CO$_2$H—Q1 |
| CF$_3$ | H | Me | 2-Me-3-CH$_2$CO$_2$Me—Q1 |
| CF$_3$ | H | Me | 2-Me-3-SH—Q1 |
| CF$_3$ | H | Me | 2-F-3-Oallyl-Q1 |
| CF$_3$ | H | Me | 2-F-3-OCH$_2$OMe—Q1 |
| CF$_3$ | H | Et | 2-F-3-CF$_3$—Q1 |
| CF$_3$ | H | NH$_2$ | 2-F-3-CF$_3$—Q1 |
| CF$_3$ | H | Me | 2-Cl-3-OH—Q1 |
| CF$_3$ | H | Me | 2-F-4-OCH$_2$OMe—Q1 |
| CF$_3$ | H | Me | 2-F-4-OCH$_2$OEt—Q1 |
| CF$_3$ | H | Me | 2-F-4-OCH$_2$CH$_2$OMe—Q1 |
| CF$_3$ | H | Me | 2-F-4-OCH$_2$CO$_2$H—Q1 |
| CF$_3$ | H | Me | 2-F-4-OCH$_2$CO$_2$Me—Q1 |
| CF$_3$ | H | Me | 2-F-4-OCH$_2$CO$_2$Et—Q1 |
| CF$_3$ | H | Me | 2-F-4-OCHMeCO$_2$Me—Q1 |
| CF$_3$ | H | Me | 2-Cl-4-OCH$_2$OMe—Q1 |
| CF$_3$ | H | Me | 2-Cl-4-OCH$_2$OEt—Q1 |
| CF$_3$ | H | Me | 2-Cl-4-OCH$_2$CH$_2$OMe—Q1 |
| CF$_3$ | H | Me | 2-Cl-4-OCH$_2$CO$_2$H—Q1 |
| CF$_3$ | H | Me | 2-Cl-4-OCH$_2$CO$_2$Me—Q1 |
| CF$_3$ | H | Me | 2-Cl-4-OCH$_2$CO$_2$Et—Q1 |
| CF$_3$ | H | Me | 2-Cl-4-OCHMeCO$_2$Me—Q1 |
| CF$_2$H | H | Me | 2-Me-3-Cl—Q1 |
| CF$_2$H | H | Me | 2-Me-3-Br—Q1 |
| CF$_2$H | H | Me | 2-Me-3-I—Q1 |
| CF$_2$H | H | Me | 2-F-3-CF$_3$—Q1 |
| CF$_2$Cl | H | Me | 2-Me-3-Cl—Q1 |

TABLE 3-1-continued

| | | | |
|---|---|---|---|
| CF$_2$Cl | H | Me | 2-Me-3-Br—Q1 |
| CF$_2$Cl | H | Me | 2-Me-3-I—Q1 |
| CF$_2$Cl | H | Me | 2-F-3-CF$_3$—Q1 |
| CCl$_3$ | H | Me | 2-Me-3-Cl—Q1 |
| CCl$_3$ | H | Me | 2-Me-3-Br—Q1 |
| CCl$_3$ | H | Me | 2-Me-3-I—Q1 |
| CCl$_3$ | H | Me | 2-F-3-CF$_3$—Q1 |
| CF$_3$ | H | Me | 2-Me—Q8 |
| CF$_3$ | H | Me | 2,3-Me$_2$—Q8 |
| CF$_3$ | H | Me | 2-Me—Q9 |
| CF$_3$ | H | Me | 3-Me—Q9 |
| CF$_3$ | H | Me | 3-OH—Q9 |
| CF$_3$ | H | Me | 3-OMe—Q9 |
| CF$_3$ | H | Me | 1-Me—Q11 |
| CF$_3$ | H | Me | 2-Me—Q11 |
| CF$_3$ | H | Me | 3-Me—Q11 |
| CF$_3$ | H | Me | 1,1-Me$_2$—Q11 |
| CF$_3$ | H | Me | 1,1,3-Me$_3$—Q11 |
| CF$_3$ | H | Me | 1,1-Me$_2$-3-Et—Q11 |
| CF$_3$ | H | Me | 1-OMe—Q11 |
| CF$_3$ | H | Me | 1-OH—Q11 |
| CF$_3$ | H | Me | 2-OMe—Q11 |
| CF$_3$ | H | Me | 2-OH—Q11 |
| CF$_3$ | H | Me | 2,3-Me$_2$—Q14 |
| CF$_3$ | H | Me | 2-Me—Q15 |
| CF$_3$ | H | Me | 3-Me—Q15 |
| CF$_3$ | H | Me | 2,2-Me$_2$—Q15 |
| CF$_3$ | H | Me | 2,2-Me$_2$—Q17 |
| CF$_3$ | H | Me | 2,2-Me$_2$—Q20 |
| CF$_3$ | H | Me | 2-Me-2-Et—Q20 |
| CF$_3$ | H | Me | Q26 |
| CF$_3$ | H | Me | 2-Me—Q26 |
| CF$_3$ | H | Me | 7-Me—Q26 |
| CF$_3$ | H | Me | 7,7-Me$_2$—Q26 |
| CF$_3$ | H | Me | 2,7,7-Me$_3$—Q26 |
| CF$_3$ | H | Me | 2-Et-7,7-Me$_2$—Q26 |
| CF$_3$ | H | Me | Q27 |
| CF$_3$ | H | Me | 7-Me—Q27 |
| CF$_3$ | H | Me | 7-OMe—Q27 |
| CF$_3$ | H | Me | Q28 |
| CF$_3$ | H | Me | Q29 |
| CF$_3$ | H | Me | 3-Me—Q29 |
| CF$_3$ | H | Me | Q30 |
| CF$_3$ | H | Me | Q31 |
| CF$_3$ | H | Me | Q32 |
| CF$_3$ | H | Me | Q33 |
| CF$_3$ | H | Me | Q34 |
| CF$_3$ | H | Me | Q35 |
| CF$_3$ | H | Me | Q36 |
| CF$_3$ | H | Me | Q37 |
| CF$_3$ | H | Me | 2,2-Me$_2$—Q37 |
| CF$_3$ | H | Me | Q38 |
| CF$_3$ | H | Me | 2,2-Me$_2$—Q38 |
| CF$_3$ | H | Me | Q39 |
| CF$_3$ | H | Me | Q40 |
| CF$_3$ | H | Me | Q41 |
| CF$_3$ | H | Me | Q42 |
| CF$_3$ | H | Me | Q43 |
| CF$_3$ | H | Me | Q44 |
| CF$_3$ | H | Me | Q45 |
| CF$_3$ | H | Me | 4-Me—Q45 |
| CF$_3$ | H | Me | Q46 |
| CF$_3$ | H | Me | Q47 |
| CF$_3$ | H | Me | 2-Me—Q47 |
| CF$_3$ | H | Me | Q48 |
| CF$_3$ | H | Me | 2-Me—Q48 |
| CF$_3$ | H | Me | Q49 |
| CF$_3$ | H | Me | Q50 |
| CF$_3$ | H | Me | Q51 |
| CF$_3$ | H | Me | Q52 |
| CF$_3$ | H | Me | Q53 |
| CF$_3$ | H | Me | Q54 |
| CF$_3$ | H | Me | Q55 |
| CF$_3$ | H | Me | Q56 |
| CF$_3$ | H | Me | Q57 |
| CF$_3$ | H | Me | 2-Me—Q57 |
| CF$_3$ | H | Me | 7-Me—Q57 |
| CF$_2$H | H | Me | Q5 |
| CF$_2$H | H | Me | Q8 |
| CF$_2$H | H | Me | 2-Me—Q8 |
| CF$_2$H | H | Me | Q9 |
| CF$_2$H | H | Me | 2-Me—Q9 |
| CF$_2$H | H | Me | 3-Me—Q9 |
| CF$_2$H | H | Me | Q11 |
| CF$_2$H | H | Me | 3-Me—Q11 |
| CF$_2$H | H | Me | 1,1,3-Me$_3$—Q11 |
| CF$_2$H | H | Me | 1-OH—Q11 |
| CF$_2$H | H | Me | 1-OMe—Q11 |
| CF$_2$H | H | Me | 2-OH—Q11 |
| CF$_2$H | H | Me | 2-OMe—Q1 |
| CF$_2$H | H | Me | Q14 |
| CF$_2$H | H | Me | Q15 |
| CF$_2$H | H | Me | 2,2-Me$_2$—Q15 |
| CF$_2$H | H | Me | 2-Me—Q15 |
| CF$_2$H | H | Me | Q17 |
| CF$_2$H | H | Me | Q19 |
| CF$_2$H | H | Me | Q20 |
| CF$_2$H | H | Me | Q26 |
| CF$_2$H | H | Me | 7,7-Me$_2$—Q26 |
| CF$_2$H | H | Me | 2,7,7-Me$_3$—Q26 |
| CF$_2$H | H | Me | Q28 |
| CF$_2$H | H | Me | Q49 |
| CF$_2$H | H | Me | Q54 |
| CF$_2$H | H | Me | Q56 |
| CF$_2$Cl | H | Me | Q5 |
| CF$_2$Cl | H | Me | Q8 |
| CF$_2$Cl | H | Me | 2-Me—Q8 |
| CF$_2$Cl | H | Me | Q9 |
| CF$_2$Cl | H | Me | 2-Me—Q9 |
| CF$_2$Cl | H | Me | 3-Me—Q9 |
| CF$_2$Cl | H | Me | Q11 |
| CF$_2$Cl | H | Me | 3-Me—Q11 |
| CF$_2$Cl | H | Me | 1,1,3-Me$_3$—Q11 |
| CF$_2$Cl | H | Me | 1-OH—Q11 |
| CF$_2$Cl | H | Me | 1-OMe—Q1 |
| CF$_2$Cl | H | Me | 2-OH—Q11 |
| CF$_2$Cl | H | Me | 2-OMe—Q11 |
| CF$_2$Cl | H | Me | Q14 |
| CF$_2$Cl | H | Me | Q15 |
| CF$_2$Cl | H | Me | 2,2-Me$_2$—Q15 |
| CF$_2$Cl | H | Me | 2-Me—Q15 |
| CF$_2$Cl | H | Me | Q17 |
| CF$_2$Cl | H | Me | Q19 |
| CF$_2$Cl | H | Me | Q20 |
| CF$_2$Cl | H | Me | Q26 |
| CF$_2$Cl | H | Me | 7,7-Me$_2$—Q26 |
| CF$_2$Cl | H | Me | 2,7,7-Me$_3$—Q26 |
| CF$_2$Cl | H | Me | Q28 |
| CF$_2$Cl | H | Me | Q49 |
| CF$_2$Cl | H | Me | Q54 |
| CF$_2$Cl | H | Me | Q56 |
| CCl$_3$ | H | Me | Q5 |
| CCl$_3$ | H | Me | Q8 |
| CCl$_3$ | H | Me | 2-Me—Q8 |
| CCl$_3$ | H | Me | Q9 |
| CCl$_3$ | H | Me | 2-Me—Q9 |
| CCl$_3$ | H | Me | 3-Me—Q9 |
| CCl$_3$ | H | Me | Q11 |
| CCl$_3$ | H | Me | 3-Me—Q11 |
| CCl$_3$ | H | Me | 1,1,3-Me$_3$—Q11 |
| CCl$_3$ | H | Me | 1-OH—Q11 |
| CCl$_3$ | H | Me | 1-OMe—Q11 |
| CCl$_3$ | H | Me | 2-OH—Q11 |
| CCl$_3$ | H | Me | 2-OMe—Q11 |
| CCl$_3$ | H | Me | Q14 |
| CCl$_3$ | H | Me | Q15 |
| CCl$_3$ | H | Me | 2,2-Me$_2$—Q15 |
| CCl$_3$ | H | Me | 2-Me—Q15 |
| CCl$_3$ | H | Me | Q17 |
| CCl$_3$ | H | Me | Q19 |
| CCl$_3$ | H | Me | Q20 |
| CCl$_3$ | H | Me | Q26 |
| CCl$_3$ | H | Me | 7,7-Me$_2$—Q26 |
| CCl$_3$ | H | Me | 2,7,7-Me$_2$—Q26 |
| CCl$_3$ | H | Me | Q28 |
| CCl$_3$ | H | Me | Q49 |
| CCl$_3$ | H | Me | Q54 |
| CCl$_3$ | H | Me | Q56 |

TABLE 3-1-continued

| | | | |
|---|---|---|---|
| CF$_3$ | H | Me | 2-Me-4-Oi-Pro—Q1 |
| CF$_3$ | H | Me | 2-Me-4-Oallyl-Q1 |
| CF$_3$ | H | Me | 2-F-4-OEt—Q1 |
| CF$_3$ | H | Me | 2,4-F$_2$-3-SMe—Q1 |
| CF$_3$ | H | Me | 2,4-F$_2$-3-Cl—Q1 |
| CF$_3$ | H | Me | 2,4-F$_2$-3-Br—Q1 |
| CF$_3$ | H | Me | 2,4-F$_2$-3-I—Q1 |
| CF$_3$ | H | Me | 2,4-F$_2$-3-OMe—Q1 |
| CF$_3$ | H | Me | 2,4-F$_2$-3-OCH$_2$OMe—Q1 |
| CF$_3$ | H | Me | 2,4-F$_2$-3-OEt—Q1 |
| CF$_3$ | H | Me | 2,4-F$_2$-3-OCHF$_2$—Q1 |
| CF$_3$ | H | Me | 2,4-F$_2$-3-OCF$_3$—Q1 |
| CF$_3$ | H | Me | 2,4-F$_2$-3-CN—Q1 |
| CF$_3$ | H | Me | 2,4-F$_2$-3-Me—Q1 |
| CF$_3$ | H | Me | 2,4-F$_2$-3-CF$_3$—Q1 |
| CF$_3$ | H | Me | 2,4-Cl$_2$-3-F—Q1 |
| CF$_3$ | H | Me | 2,4-Cl$_2$-3-Br—Q1 |
| CF$_3$ | H | Me | 2,4-Cl$_2$-3-I—Q1 |
| CF$_3$ | H | Me | 2,4-Cl$_2$-3-CF$_3$—Q1 |
| CF$_3$ | H | Me | 2-F-3,4-Cl$_2$—Q1 |
| CF$_3$ | H | Me | 2-F-3-Br-4-Cl—Q1 |
| CF$_3$ | H | Me | 2,3-F$_2$-4-Cl—Q1 |
| CF$_3$ | H | Me | 2,4-F$_2$-3,5-Cl$_2$—Q1 |
| CF$_3$ | H | Me | 2-F-3-Cl-4-Br—Q1 |
| CF$_3$ | H | Me | 2,3,4,5-F$_4$—Q1 |
| CF$_3$ | H | Me | 2,3,4,5-Cl$_4$—Q1 |
| CF$_3$ | H | Me | 2-Me—Q12 |
| CF$_3$ | H | Me | 6-Me—Q23 |
| CF$_2$H | H | Me | 2-F-3-Cl—Q1 |
| CF$_2$H | H | Me | 2-F-3-Br—Q1 |
| CF$_2$H | H | Me | 2-F-3-I—Q1 |
| CF$_2$H | H | Me | 2,4-F$_2$-3-Cl—Q1 |
| CF$_2$H | H | Me | 2,4-F$_2$-3-Br—Q1 |
| CF$_2$H | H | Me | 2,4-F$_2$-3-I—Q1 |
| CF$_2$H | H | Me | 2,4-F$_2$-3,5-Cl$_2$—Q1 |
| CF$_2$Cl | H | Me | 2-F-3-Cl—Q1 |
| CF$_2$Cl | H | Me | 2-F-3-Br—Q1 |
| CF$_2$Cl | H | Me | 2-F-3-I—Q1 |
| CF$_2$Cl | H | Me | 2,4-F$_2$-3-Cl—Q1 |
| CF$_2$Cl | H | Me | 2,4-F$_2$-3-Br—Q1 |
| CF$_2$Cl | H | Me | 2,4-F$_2$-3-I—Q1 |
| CF$_2$Cl | H | Me | 2,4-F$_2$-3,5-Cl$_2$—Q1 |
| CCl$_3$ | H | Me | 2-F-3-Cl—Q1 |
| CCl$_3$ | H | Me | 2-F-3-Br—Q1 |
| CCl$_3$ | H | Me | 2-F-3-I—Q1 |
| CCl$_3$ | H | Me | 2,4-F$_2$-3-Cl—Q1 |
| CCl$_3$ | H | Me | 2,4-F$_2$-3-Br—Q1 |
| CCl$_3$ | H | Me | 2,4-F$_2$-3-I—Q1 |
| CCl$_3$ | H | Me | 2,4-F$_2$-3,5-Cl$_2$—Q1 |
| CF$_3$ | H | Me | 2,4-F$_2$-3-CO$_2$Me—Q1 |
| CF$_3$ | H | Me | 2,4-Cl$_2$-3-Me—Q1 |
| CF$_3$ | H | Me | 1-MeCO$_2$—Q11 |
| CF$_3$ | H | Me | 2-Me—Q12 |
| CF$_3$ | H | Me | 2,4,6-F$_3$—Q1 |
| CF$_3$ | H | Me | 2,3,6-F$_3$—Q1 |
| CF$_3$ | H | Me | 2,6-Cl$_2$-4-CF$_3$—Q1 |
| CF$_3$ | H | Me | 2,4,6-Cl$_3$—Q1 |
| CF$_3$ | H | Me | 2,6-F$_2$-4-CF$_3$—Q1 |
| CF$_3$ | H | Me | 2,3-Me$_2$-4-OMe—Q1 |
| CF$_3$ | H | Me | 2-Cl-3,4-Me$_2$—Q1 |
| CF$_3$ | H | Me | 2-Me-3-Cl-4-F—Q1 |
| CF$_3$ | H | Me | 2-Me-3-Br-4-F—Q1 |
| CF$_3$ | H | Me | 2-Me-3-I-4-F—Q1 |
| CF$_3$ | H | Me | 2-Me-3-OMe-4-F—Q1 |
| CF$_3$ | H | Me | 2,3-Cl$_2$-4-F—Q1 |
| CF$_3$ | H | Me | 2-Cl-3-Br-4-F—Q1 |
| CF$_3$ | H | Me | 2-Cl-3-I-4-F—Q1 |
| CF$_3$ | H | Me | 2-Cl-3-OMe-4-F—Q1 |
| CF$_3$ | H | Me | 2-OMe-3-F-4-Cl—Q11 |
| CF$_3$ | H | Me | 2-OMe-3,4-Cl$_2$—Q1 |
| CF$_3$ | H | Me | 2,4-(OMe)$_2$-3-Cl—Q1 |
| CF$_3$ | H | Me | 2-F-3,4-Me$_2$—Q1 |
| CF$_3$ | H | Me | 2-OMe-3,4-Me$_2$—Q1 |
| CF$_3$ | H | Me | 2-Br-3,4-Me$_2$—Q1 |
| CF$_3$ | H | Me | 2,4-Cl$_2$-3-OMe—Q1 |
| CF$_3$ | H | Me | 2,4-Cl$_2$-3-CH$_2$OMe—Q1 |
| CF$_3$ | H | Me | 2,4-F$_2$-3-CH$_2$OMe—Q1 |
| CF$_3$ | H | Me | 7-F—Q17 |
| CF$_3$ | H | Me | 2-OMe-3,4-F$_2$—Q1 |
| CF$_3$ | H | Me | 2-OMe-3-Cl-4-F—Q1 |
| CF$_3$ | H | Me | 2-OMe-3-Br-4-F—Q1 |
| CF$_3$ | H | Me | 2,4,5-F$_3$—Q1 |
| CF$_3$ | H | Me | 2-SMe-3-Cl-4-F—Q1 |
| CF$_3$ | H | Me | 2,4-Me$_2$-3-Br—Q1 |
| CF$_3$ | H | Me | 2,4-Me$_2$-3-I—Q1 |

TABLE 3-2

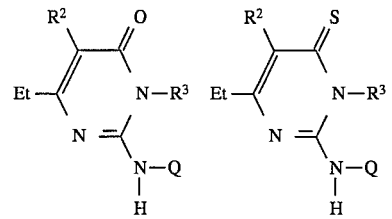

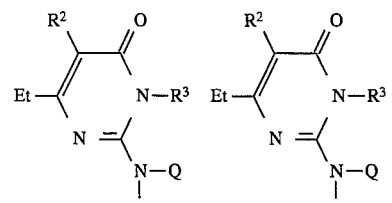

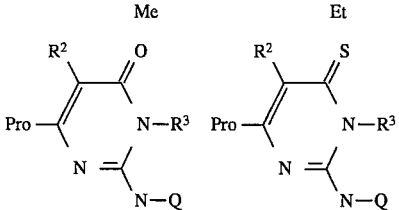

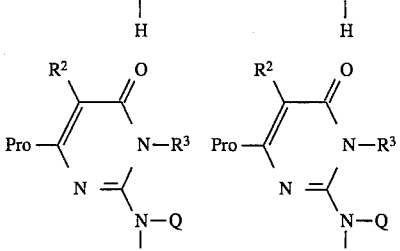

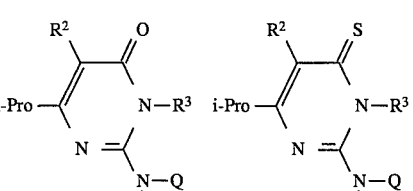

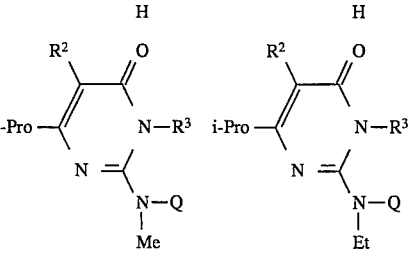

TABLE 3-2-continued

TABLE 3-2-continued

TABLE 3-2-continued

TABLE 3-2-continued

TABLE 3-2-continued
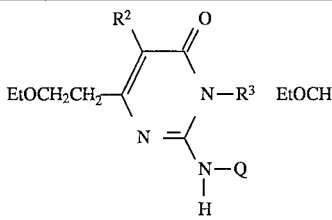

TABLE 3-2-continued
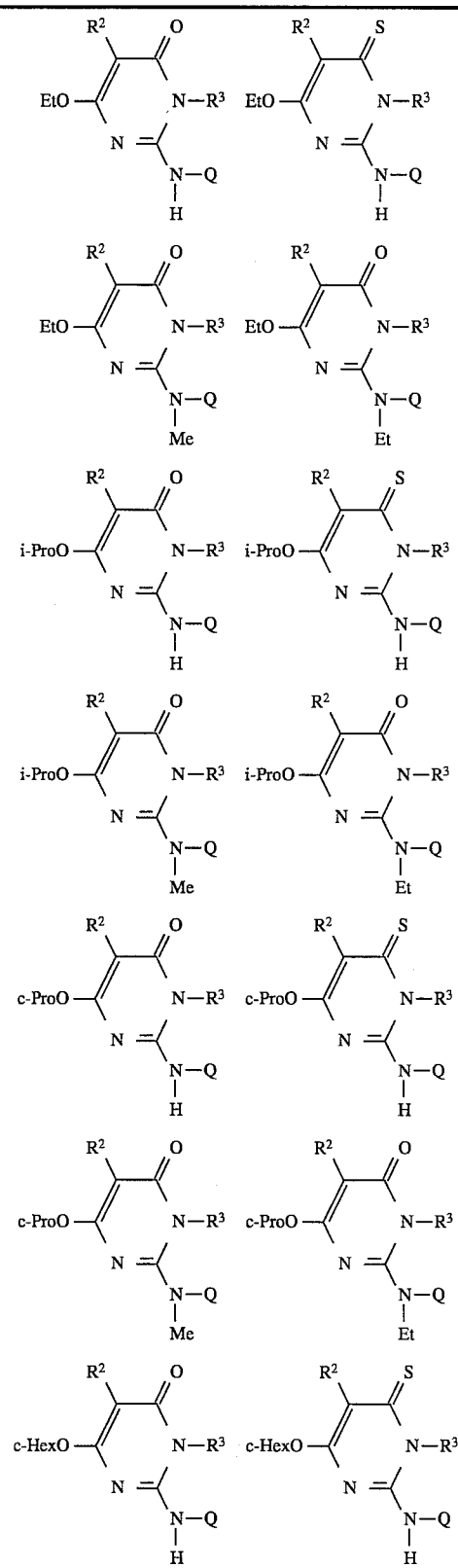
TABLE 3-2-continued
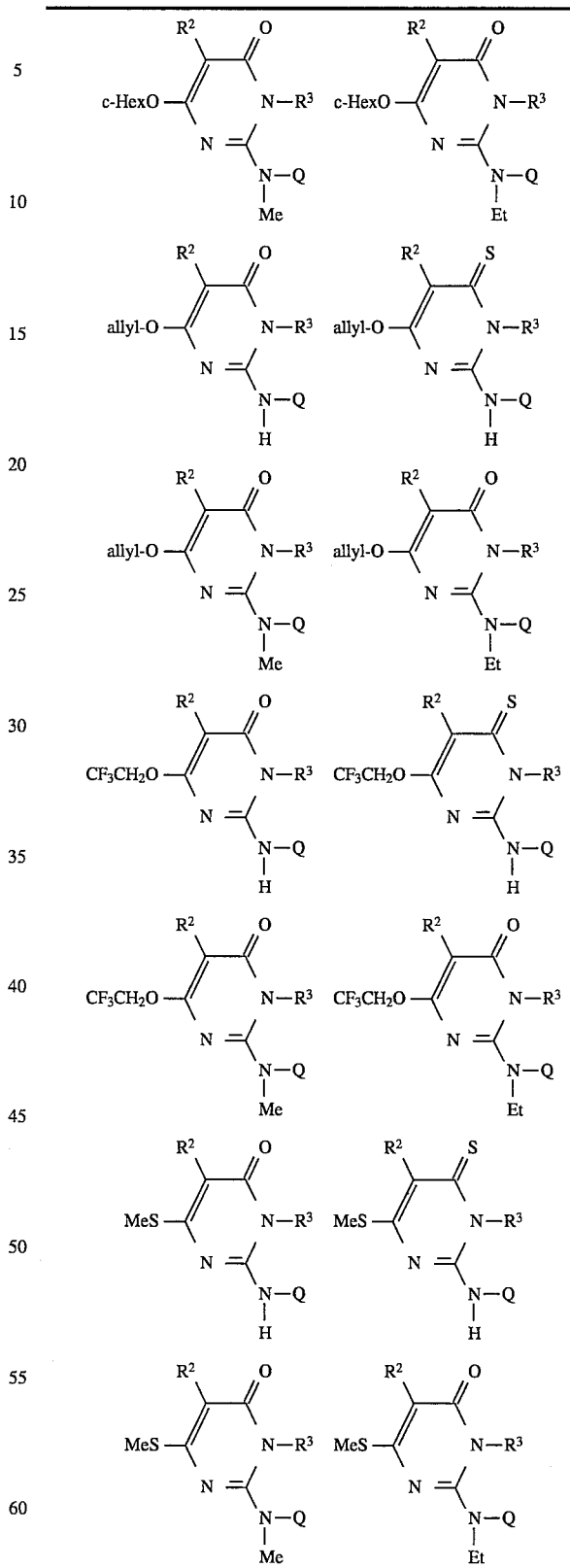

TABLE 3-2-continued

TABLE 3-2-continued
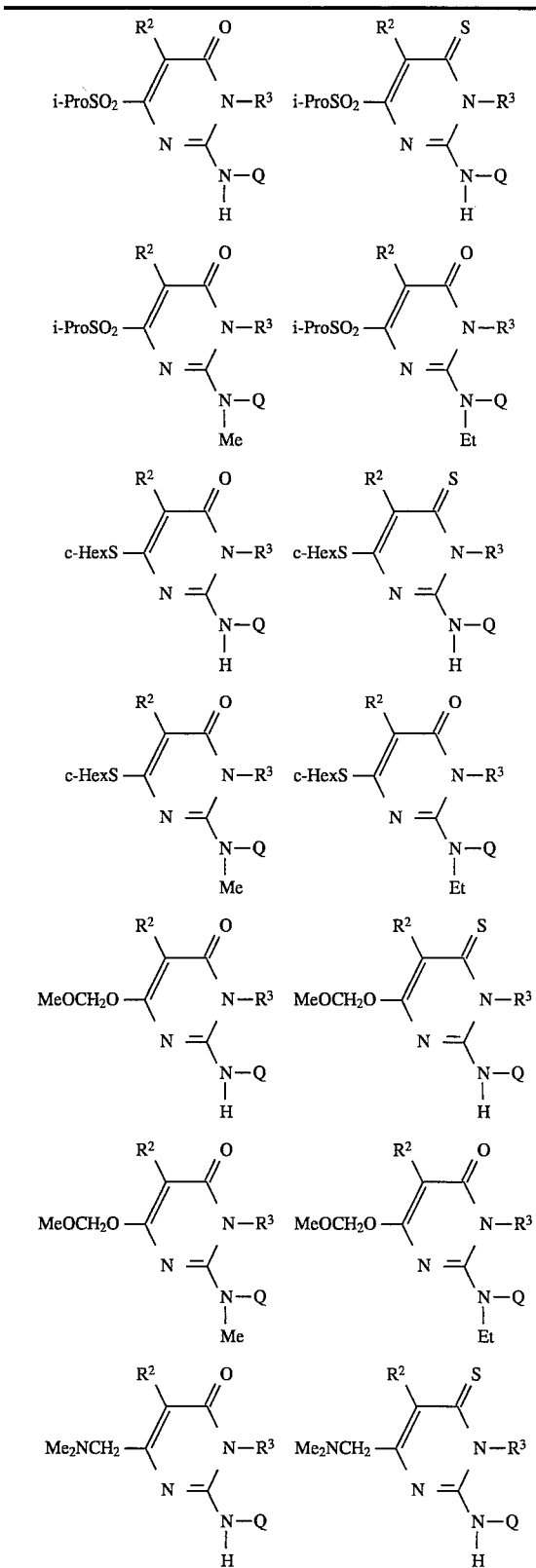
TABLE 3-2-continued
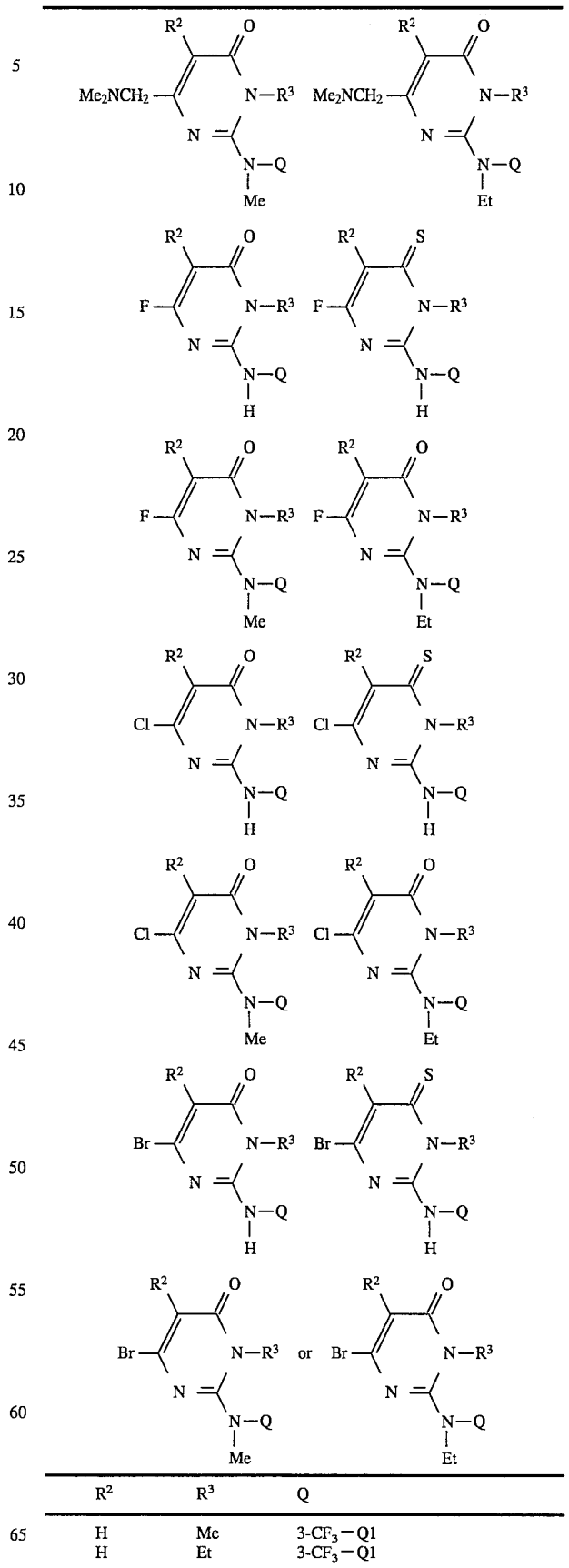
| $R^2$ | $R^3$ | Q |
|---|---|---|
| H | Me | 3-CF$_3$—Q1 |
| H | Et | 3-CF$_3$—Q1 |

TABLE 3-2-continued

| | | |
|---|---|---|
| Me | Me | 3-CF$_3$—Q1 |
| H | Me | 2-OCH$_2$OMe—Q1 |
| H | Me | 3-OCH$_2$OMe—Q1 |
| H | Me | 4-OCH$_2$OMe—Q1 |
| H | Me | 3-OCH$_2$OEt—Q1 |
| H | Me | 4-OCH$_2$OEt—Q1 |
| H | Me | 3-OCH$_2$CH$_2$OMe—Q1 |
| H | Me | 4-OCH$_2$CH$_2$OMe—Q1 |
| H | Me | 3-OCH$_2$CO$_2$H—Q1 |
| H | Me | 4-OCH$_2$CO$_2$H—Q1 |
| H | Me | 3-OCH$_2$CO$_2$Me—Q1 |
| H | Me | 4-OCH$_2$CO$_2$Me—Q1 |
| H | Me | 3-OCHMeCO$_2$Me—Q1 |
| H | Me | 4-OCHMeCO$_2$Me—Q1 |
| H | Me | 2,3-Cl$_2$—Q1 |
| H | NH$_2$ | 2,3-Cl$_2$—Q1 |
| H | Me | 2, 4-Cl$_2$—Q1 |
| H | Me | 2-Me-3-Cl—Q1 |
| H | Me | 2-Me-3-Br—Q1 |
| H | Me | 2-Me-3-I—Q1 |
| H | Me | 2-Me-3-OMe—Q1 |
| H | Me | 2-Me-3-Oallyl-Q1 |
| H | Me | 2-Me-3-OCH$_2$OMe—Q1 |
| H | Me | 2-Me-3-OCH$_2$OEt—Q1 |
| H | Me | 2-Me-3-OCH$_2$CH$_2$OMe—Q1 |
| H | Me | 2-Me-3-OCH$_2$CO$_2$H—Q1 |
| H | Me | 2-Me-3-OCH$_2$CO$_2$Me—Q1 |
| H | Me | 2-Me-4-Oallyl-Q1 |
| H | Me | 2-Me-4-OCH$_2$OMe—Q1 |
| H | Me | 2-Me-4-OCH$_2$OET—Q1 |
| H | Me | 2-Me-4-OCH$_2$CH$_2$OMe—Q1 |
| H | Me | 2-Me-4-OCH$_2$CO$_2$H—Q1 |
| H | Me | 2-Me-4-OCH$_2$CO$_2$Me—Q1 |
| H | Me | 2-Me-4-OCHMeCO$_2$Me—Q1 |
| H | Me | 2-F-3-CF$_3$—Q1 |
| H | Me | 2-Cl-3-CF$_3$—Q1 |
| H | Me | 2-F-4-OCH$_2$OMe—Q1 |
| H | Me | 2-Cl-4-OCH$_2$OMe—Q1 |
| H | Me | 2-F-4-OCH$_2$OEt—Q1 |
| H | Me | 2-Cl-4-OCH$_2$OEt—Q1 |
| H | Me | 2-F-4-OCH$_2$CH$_2$OMe—Q1 |
| H | Me | 2-Cl-4-OCH$_2$CH$_2$OMe—Q1 |
| H | Me | 2-F-4-OCH$_2$CO$_2$H—Q1 |
| H | Me | 2-Cl-4-OCH$_2$CO$_2$H—Q1 |
| H | Me | 2-F-4-OCH$_2$CO$_2$Me—Q1 |
| H | Me | 2-C-4-OCH$_2$CO$_2$Me—Q1 |
| H | Me | 2-F-4-OCHMeCO$_2$Me—Q1 |
| H | Me | 2-Cl-4-OCHMeCO$_2$Me—Q1 |
| H | Me | 2,3-(OMe)$_2$—Q1 |
| H | Me | 2-OMe-3-Cl—Q1 |
| H | Me | 2-OMe-3-CF$_3$—Q1 |
| H | Me | 2,3,4-F$_3$ |
| H | Me | 2,3,4-Cl$_3$ |
| H | Me | Q3 |
| H | Me | Q5 |
| H | Me | Q8 |
| H | Me | 2-Me—Q8 |
| H | Me | 2,3-Me2—Q8 |
| H | Me | Q9 |
| H | Me | 2-Me—Q9 |
| H | Me | 3-Me—Q9 |
| H | Me | 3-OH—Q9 |
| H | Me | 3-OMe—Q9 |
| H | Me | Q11 |
| H | Me | 1-Me—Q11 |
| H | Me | 2-Me-Q11 |
| H | Me | 3-Me-Q11 |
| H | Me | 1,1-Me$_2$—Q1 |
| H | Me | 1,1,3-Me$_3$—Q1 |
| H | Me | 1,1-Me$_2$-3-Et—Q11 |
| H | Me | 1-OME—Q11 |
| H | Me | 1-OH—Q1 |
| H | Me | 2-OMe—Q11 |
| H | Me | 2-OH—Q1 |
| H | Me | Q14 |
| H | Me | 2,3-Me$_2$—Q14 |
| H | Me | Q15 |
| H | Me | 2-Me—Q15 |
| H | Me | 3-Me—Q15 |
| H | Me | 2,2-Me2—Q15 |
| H | Me | Q17 |
| H | Me | 2,2-Me$_2$—Q17 |
| H | Me | Q20 |
| H | Me | 2,2-Me$_2$—Q20 |
| H | Me | 2-Me-2-Et—Q20 |
| H | Me | Q26 |
| H | Me | 2-Me—Q26 |
| H | Me | 7-Me-Q26 |
| H | Me | 7,7-Me$_2$—Q26 |
| H | Me | 2,7,7-Me$_3$—Q26 |
| H | Me | 2-Et-7,7-Me$_2$—Q26 |
| H | Me | Q27 |
| H | Me | 7-Me—Q27 |
| H | Me | 7-OMe—Q27 |
| H | Me | Q28 |
| H | Me | Q29 |
| H | Me | 3-Me—Q29 |
| H | Me | Q30 |
| H | Me | Q31 |
| H | Me | Q32 |
| H | Me | Q33 |
| H | Me | Q34 |
| H | Me | Q35 |
| H | Me | Q36 |
| H | Me | Q37 |
| H | Me | 2,2-Me$_2$—Q37 |
| H | Me | Q38 |
| H | Me | 2,2-Me$_2$—Q38 |
| H | Me | Q39 |
| H | Me | Q40 |
| H | Me | Q41 |
| H | Me | Q42 |
| H | Me | Q43 |
| H | Me | Q44 |
| H | Me | Q45 |
| H | Me | 4-Me—Q45 |
| H | Me | Q46 |
| H | Me | Q47 |
| H | Me | 2-Me—Q47 |
| H | Me | Q48 |
| H | Me | 2-Me—Q48 |
| H | Me | Q49 |
| H | Me | Q50 |
| H | Me | Q51 |
| H | Me | Q52 |
| H | Me | Q53 |
| H | Me | Q54 |
| H | Me | Q55 |
| H | Me | Q56 |
| H | Me | Q57 |
| H | Me | 2-Me—Q57 |
| H | Me | 7-Me—Q57 |
| H | Me | 2-F-3-Cl—Q1 |
| H | Me | 2-F-3-Br—Q1 |
| H | Me | 2-F-3-I—Q1 |
| H | Me | 2,4-F$_2$-3-Cl—Q1 |
| H | Me | 2,4-F$_2$-3-Br—Q1 |
| H | Me | 2,4-F$_2$-3-I—Q1 |
| H | Me | 2,4-F$_2$-3-OMe—Q1 |
| H | Me | 2,4-F$_2$-3-OCH$_2$OMe—Q1 |
| H | Me | 2,4-F$_2$-3-OEt—Q1 |
| H | Me | 2,4-F$_2$-3-OCHF$_2$—Q1 |
| H | Me | 2,4-F$_2$-3-OCF$_3$—Q1 |
| H | Me | 2,4-F$_2$-3-CN—Q1 |
| H | Me | 2,4-F$_2$-3-Me—Q1 |
| H | Me | 2,4-F$_2$-3-CF$_3$—Q1 |
| H | Me | 2, 4-Cl$_2$-3-F—Q1 |
| H | Me | 2,4-Cl$_2$-3-Br—Q1 |
| H | Me | 2,4-Cl$_2$-3-I—Q1 |
| H | Me | 2,4-Cl$_2$-3-CF$_3$—Q1 |
| H | Me | 2-F-3,4-Cl$_2$—Q1 |
| H | Me | 2-F-3-Br-4-Cl—Q1 |
| H | Me | 2,3-F$_2$-4-Cl—Q1 |
| H | Me | 2,4-F$_2$-3,5-Cl$_2$—Q1 |
| H | Me | 2-F-3-Cl-4-Br—Q1 |
| H | Me | 2,3,4,5-F$_4$—Q1 |
| H | Me | 2,3,4,5-Cl$_4$—Q1 |
| H | Me | 2,4-F$_2$-3-CO$_2$Me—Q1 |

TABLE 3-2-continued

| | | |
|---|---|---|
| H | Me | 2,4-Cl$_2$-3-Me—Q1 |
| H | Me | 1-MeCO$_2$—Q11 |
| H | Me | 2-Me—Q12 |
| H | Me | 2,4,6-F$_3$—Q1 |
| H | Me | 2,3,6-F$_3$—Q1 |
| H | Me | 2,6-Cl$_2$-4-CF$_3$—Q1 |
| H | Me | 2,4,6-Cl$_3$—Q1 |
| H | Me | 2,6-F$_2$-4-CF$_3$—Q1 |
| H | Me | 2,3-Me$_2$-4-OMe—Q1 |
| H | Me | 2-Cl-3,4-Me$_2$—Q1 |
| H | Me | 2-Me-3-Cl-4-F—Q1 |
| H | Me | 2-Me-3-Br-4-F—Q1 |
| H | Me | 2-Me-3-I-4-F—Q1 |
| H | Me | 2-Me-3-OMe-4-F—Q1 |
| H | Me | 2,3-Cl$_2$-4-F—Q1 |
| H | Me | 2-Cl-3-Br-4-F—Q1 |
| H | Me | 2-Cl-3-I-4-F—Q1 |
| H | Me | 2-Cl-3-OMe-4-F—Q1 |
| H | Me | 2-OMe-3-F-4-Cl—Q1 |
| H | Me | 2-OMe-3,4-Cl$_2$—Q1 |
| H | Me | 2,4-(OMe)$_2$-3-Cl—Q1 |
| H | Me | 2-F-3,4-Me$_2$—Q1 |
| H | Me | 2-OMe-3,4-Me$_2$—Q1 |
| H | Me | 2-Br-3,4-Me$_2$—Q1 |
| H | Me | 2,4-Cl$_2$-3-OMe—Q1 |
| H | Me | 2,4-Cl$_2$-3-CH$_2$OMe—Q1 |
| H | Me | 2,4-F$_2$-3-CH$_2$OMe—Q1 |
| H | Me | 7-F—Q17 |
| H | Me | 2-OMe-3,4-F$_2$—Q1 |
| H | Me | 2-OMe-3-Cl-4-F—Q1 |
| H | Me | 2-OMe-3-Br-4-F—Q1 |
| H | Me | 2,4,5-F$_3$—Q1 |
| H | Me | 2-SMe-3-Cl-4-F—Q1 |
| H | Me | 2,4-Me$_2$-3-Br—Q1 |
| H | Me | 2,4-Me$_2$-3-I—Q1 |

In Table 3-1 and Table 3-2, Q1 and Q57 represent the following formulae.

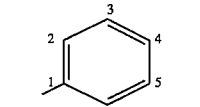 Q1

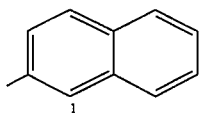 Q2

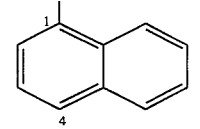 Q3

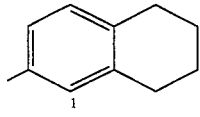 Q4

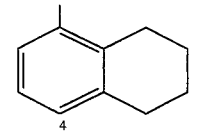 Q5

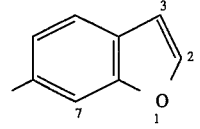 Q6

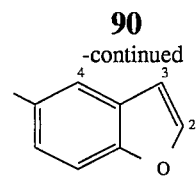 Q7

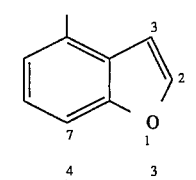 Q8

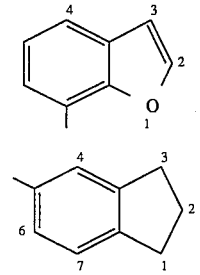 Q9

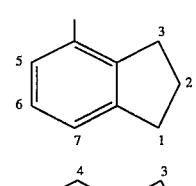 Q10

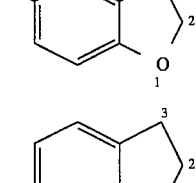 Q11

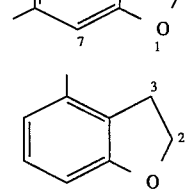 Q12

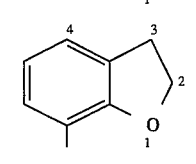 Q13

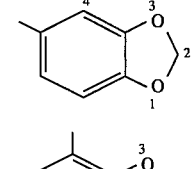 Q14

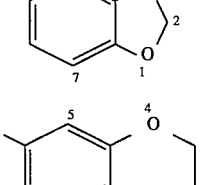 Q15

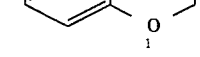 Q16

Q17

Q18

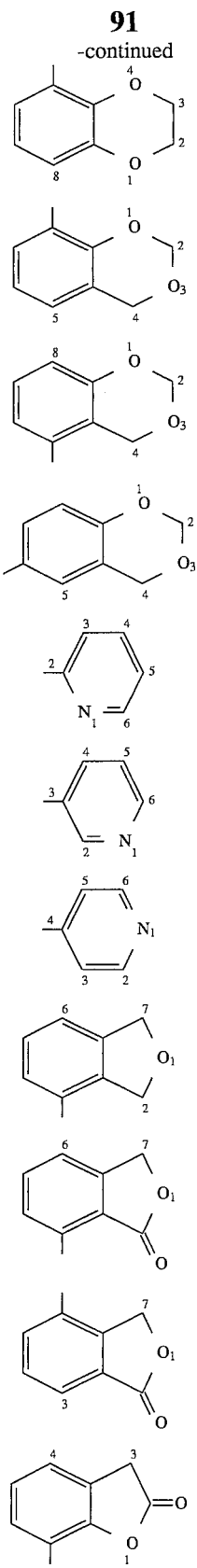
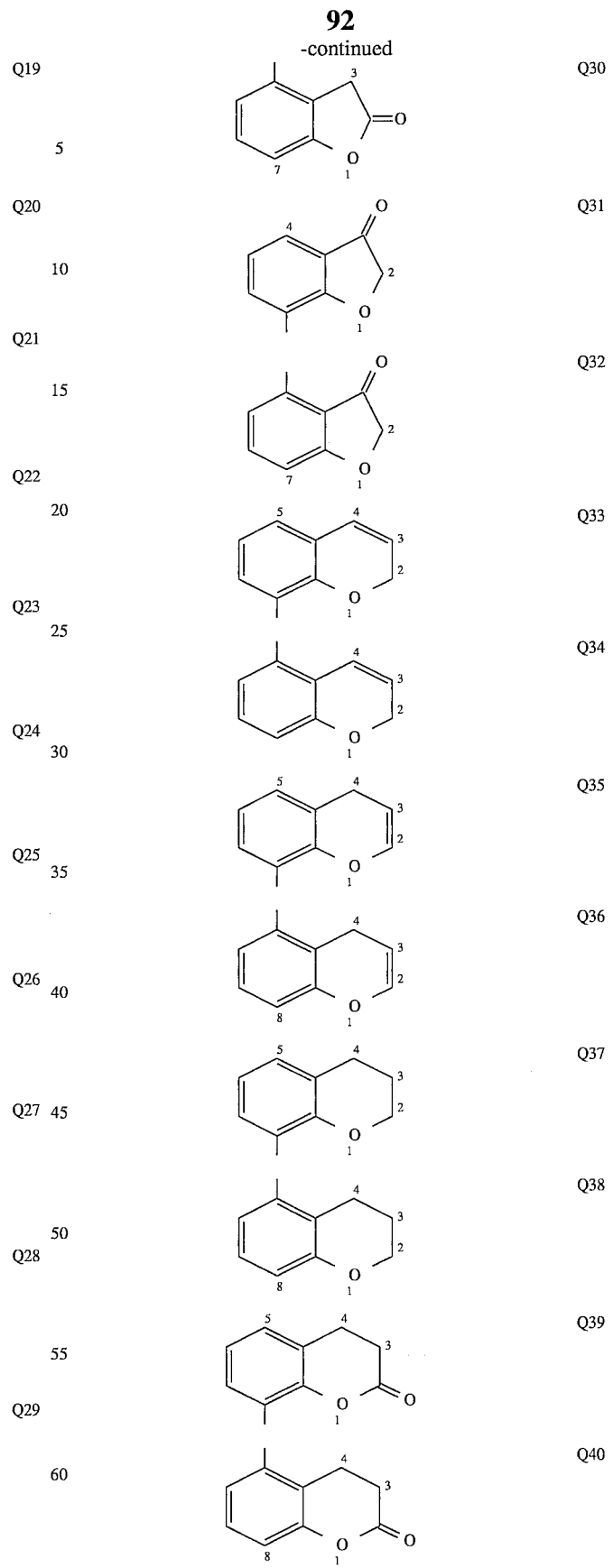

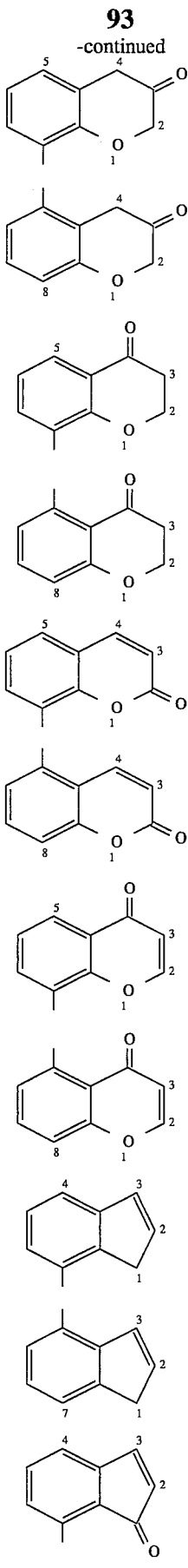
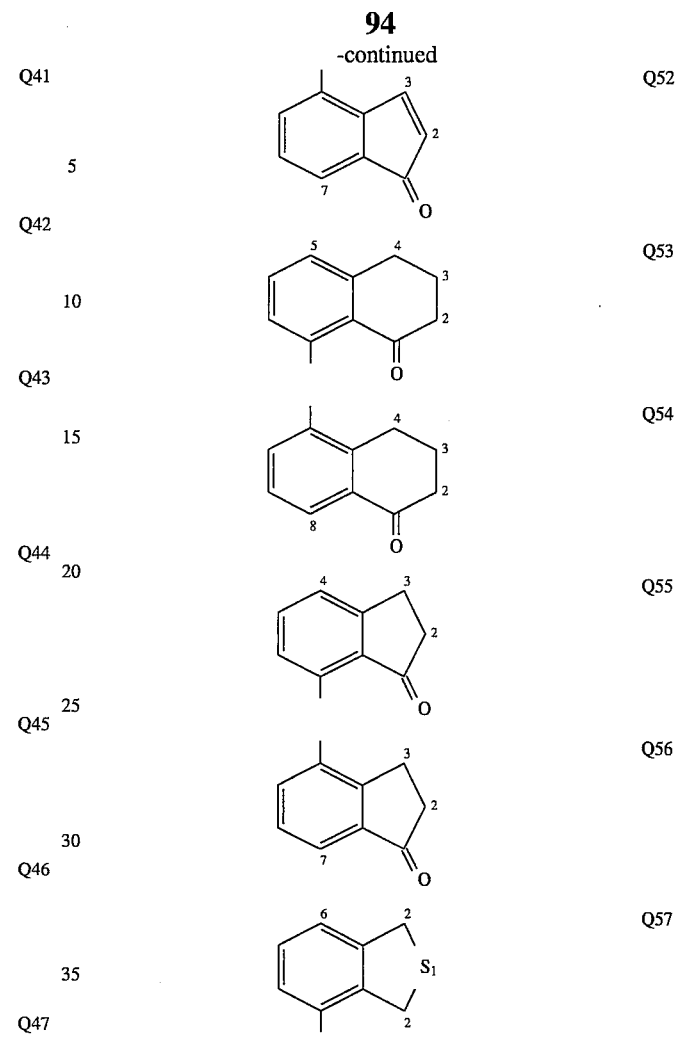

When the compound of the present invention is used as a herbicide or a plant growth regulator, it can be generally used by mixing with a suitable carrier, for example, a solid carrier such as clay, talc, bentonite, diatomaceous earth, white carbon, etc. or a liquid carrier such as water, alcohols (isopropanol, butanol, benzyl alcohol, furfuryl alcohol, etc.), aromatic hydrocarbons (toluene, xylene, etc.), ethers (anisoles), ketones (cyclohexanone and isophorones), esters (butyl acetate, etc.), acid amides (N-methylpyrrolidone, etc.), halogenated hydrocarbons (chlorobenzene, etc.) and others. If desired, by adding a surfactant, an emulsifying agent, a dispersant, a penetrant, a spreading agent, a thickener, an antifreezing agent, an anticoagulant, a stabilizer, etc., the compound of the present invention can be provided for practical use in any desired preparation form such as a liquid agent, an emulsion, a wettable powder, a dry flowable agent, a flowable agent, a powder, a granule, etc.

Further, the compound of the present invention may be mixed with other kind of herbicide, various insecticides, fungicides, plant growth regulators and synergists, etc. at the time of preparation or spraying, if necessary.

Particularly when the compound of the present invention is mixed with another herbicide, there can be expected cost which is reduced because a dose of the compound of the present invention to be used is decreased, a grass-killing spectrum enlarged by synergism of the mixed chemicals and a higher grass-killing effect. Also, the compound of the present invention can be mixed with plural known herbicides simultaneously. As a kind of the herbicide to be mixed with the compound of the present invention, there may be mentioned, for example, compounds described in Farm Chemicals Handbook (1990), etc.

As a preferred chemical to be used by mixing with the compound of the present invention, there may be mentioned, for example, pyrazosulfuron ethyl (general name), bensulfuron methyl (general name), cinosulfuron (general name), imazosulfuron (general name), pretilachlor (general name), esprocarb (general name), pyrazolate (general name), pyrazoxyfen (general name), benzofenap (general name), dymron (general name), bromobutide (general name), naproanilide (general name), clomeprop (general name), CNP (general name), chlomethoxynil (general name), bifenox (general name), oxadiazon (general name), mefenacet (general name), butachlor (general name), butenachlor (general name), dithiopyr (general name), benfuresate (general name), pyributicarb (general name), benthiocarb (general name), dimepiperate (general name), molinate (general name), butamifos (general name), quinclorac (general name), cinmethylin (general name), propanil (general name), simetryn (general name), SAP (bensulide/(general name)), dimethametryn (general name), MCPA, MCPB, 2',3'-dichloro-ethoxymethoxybenzanilide (test name: HW-52), 1-(2-chlorobenzyl)-3-($\alpha,\alpha$-dimethylbenzyl)urea (test name: JC-940), N-[2'-(3'-methoxy)thienylmethyl]-N-chloroacetyl-2,6-dimethylanilide (test name: NSK-850), Compound (II) described in Japanese Provisional Patent Publication No. 25009/1993, etc.

The dose of the compound of the present invention to be used as a herbicide varies depending on application place, application time, application method, crops to be grown, etc., but its dose as an active ingredient is generally suitably about 0.0001 to 10 kg, preferably about 0.001 to 5 kg per hectare (ha).

Further, the application concentration of the compound of the present invention as a plant growth regulator varies depending on application purpose, kinds of target crops or true grasses, application time, application method, etc., but its concentration as an active ingredient is generally suitably about 1 to 10,000 ppm, preferably about 10 to 2,000 ppm.

In the following, formulation examples of preparations when the compound of the present invention is used are shown specifically. However, formulation examples of the present invention are not limited to these. In the following Formulation examples, "part" means "part by weight".

[Wettable powder]

| Compound of the present invention | 5 to 80 parts |
|---|---|
| Solid carrier | 10 to 85 parts |
| Surfactant | 1 to 10 parts |
| Others | 1 to 5 parts |

As others, there may be mentioned, for example, an anticoagulant, etc.

[Emulsion]

| Compound of the present invention | 1 to 30 parts |
|---|---|
| Liquid carrier | 30 to 95 parts |
| Surfactant | 5 to 15 parts |

[Flowable agent]

| Compound of the present invention | 5 to 70 parts |
|---|---|
| Liquid carrier | 15 to 65 parts |
| Surfactant | 5 to 12 parts |
| Others | 5 to 30 parts |

As others, there may be mentioned, for example, an antifreezing agent, a thickener, etc.

[Granular wettable powder (dry flowable agent)]

| Compound of the present invention | 20 to 90 parts |
|---|---|
| Solid carrier | 9 to 60 parts |
| Surfactant | 1 to 20 parts |

[Granule]

| Compound of the present invention | 0.01 to 10 parts |
|---|---|
| Solid carrier | 90 to 9.99 parts |
| Others | 0 to 5 parts |

Formulation Example 1

Wettable powder

| Compound A-1 of the present invention | 50 parts |
|---|---|
| Ziegleit PFP (kaolin type clay: trade name, produced by Ziegleit Kogyo K.K.) | 43 parts |
| Solpol 5050 (anionic surfactant: trade name, produced by Toho Kagaku Kogyo K.K.) | 2 parts |
| Runox 1000C (anionic surfactant: trade name, produced by Toho Kagaku Kogyo K.K.) | 3 parts |
| Carplex #80 (anticoagulant) (white carbon: trade name, produced by Shionogi Seiyaku K.K.) | 2 parts |

The above components are mixed uniformly and pulverized to prepare a wettable powder.

Formulation Example 2

Emulsion

| Compound A-28 of the present invention | 3 parts |
|---|---|
| Xylene | 76 parts |
| Isophorone | 15 parts |
| Solpol 3005X (mixture of nonionic surfactant and anionic surfactant: trade name, produced by Toho Kagaku Kogyo K.K.) | 6 parts |

The above components are mixed uniformly to prepare an emulsion.

Formulation Example 3

Flowable agent

| Compound B-26 of the present invention | 35 parts |
|---|---|
| Agrisol S-711 (nonionic surfactant: trade name, produced by Kao K.K.) | 8 parts |
| Runox 1000C (anionic surfactant: trade name, produced by Toho Kagaku Kogyo K.K.) | 0.5 part |
| 1% Rodopol solution (thickener: trade name, produced by Rohne Poulainc Co.) | 20 parts |
| Ethylene glycol (antifreezing agent) | 8 parts |
| Water | 28.5 parts |

The above components are mixed uniformly to prepare a flowable agent.

Formulation Example 4

Granular wettable powder (dry flowable agent)

| Compound A-78 of the present invention | 75 parts |
|---|---|
| Isobam No. 1 (anionic surfactant: trade name, produced by Kuraray Isoprene Chemical K.K.) | 10 parts |

-continued

| | |
|---|---|
| Vanilex N (anionic surfactant: trade name, produced by Sanyo Kokusaku Pulp K.K.) | 5 parts |
| Carplex #80 (white carbon: trade name, produced by Shionogi Seiyaku K.K.) | 10 parts |

The above components are mixed uniformly and pulverized finely to prepare a dry flowable agent.

Formulation Example 5

Granule

| | |
|---|---|
| Compound A-73 of the present invention | 0.1 part |
| Bentonite | 55.0 parts |
| Talc | 44.9 parts |

The above components are mixed uniformly and pulverized, and then a small amount of water is added thereto. The mixture was stirred, mixed and kneaded, and granulated by an extrusion type granulator, followed by drying, to prepare a granule.

Formulation Example 6

Wettable powder

| | |
|---|---|
| Compound A-94 of the present invention | 50 parts |
| Ziegleit PFP (kaolin type clay: trade name, produced by Ziegleit Kogyo K.K.) | 43 parts |
| Solpol 5050 (anionic surfactant: trade name, produced by Toho Kagaku Kogyo K.K.) | 2 parts |
| Runox 1000C (anionic surfactant: trade name, produced by Toho Kagaku Kogyo K.K.) | 3 parts |
| Carplex #80 (anticoagulant) (white carbon: trade name, produced by Shionogi Seiyaku K.K.) | 2 parts |

The above components are mixed uniformly and pulverized to prepare a wettable powder.

Formulation Example 7

Emulsion

| | |
|---|---|
| Compound A-88 of the present invention | 3 parts |
| Xylene | 76 parts |
| Isophorone | 15 parts |
| Solpol 3005X (mixture of nonionic surfactant and anionic surfactant: trade name, produced by Toho Kagaku Kogyo K.K.) | 6 parts |

The above components are mixed uniformly to prepare an emulsion.

Formulation Example 8

Flowable agent

| | |
|---|---|
| Compound A-83 of the present invention | 35 parts |
| Agrisol S-711 (nonionic surfactant: trade name, produced by Kao K.K.) | 8 parts |
| Runox 1000C (anionic surfactant: trade name, produced by Toho Kagaku Kogyo K.K.) | 0.5 part |
| 1% Rodopol solution (thickener: trade name, produced by Rohne Poulainc Co.) | 20 parts |
| Ethylene glycol (antifreezing agent) | 8 parts |
| Water | 28.5 parts |

The above components are mixed uniformly to prepare a flowable agent.

Formulation Example 9

Granular wettable powder (dry flowable agent)

| | |
|---|---|
| Compound A-85 of the present invention | 75 parts |
| Isobam No. 1 (anionic surfactant: trade name, produced by Kuraray Isoprene Chemical K.K.) | 10 parts |
| Vanilex N (anionic surfactant: trade name, produced by Sanyo Kokusaku Pulp K.K.) | 5 parts |
| Carplex #80 (white carbon: trade name, produced by Shionogi Seiyaku K.K.) | 10 parts |

The above components are mixed uniformly and pulverized finely to prepare a dry flowable agent.

Formulation Example 10

Granule

| | |
|---|---|
| Compound A-93 of the present invention | 0.1 part |
| Bentonite | 55.0 parts |
| Talc | 44.9 parts |

The above components are mixed uniformly and pulverized, and then a small amount of water is added thereto. The mixture was stirred, mixed, and kneaded, and granulated by an extrusion type granulator, followed by drying, to prepare a granule.

Formulation Example 11

Flowable agent

| | |
|---|---|
| Compound B-1 of the present invention | 35 parts |
| Agrisol S-711 (nonionic surfactant: trade name, produced by Kao K.K.) | 8 parts |
| Runox 1000 C (anionic surfactant: trade name, produced by Toho Kagaku Kogyo K.K.) | 0.5 part |
| 1% Rodopol solution (thickener: trade name, produced by Rohne Poulainc Co.) | 20 parts |
| Ethylene glycol (antifreezing agent) | 8 parts |
| Water | 28.5 parts |

The above components are mixed uniformly to prepare a flowable agent.

Formulation Example 12

Granule

| | |
|---|---|
| Compound B-7 of the present invention | 0.1 part |
| Bentonite | 55.0 parts |
| Talc | 44.9 parts |

Formulation Example 13

Granule

| | |
|---|---|
| Compound A-73 of the present invention | 10.0 part |
| Pyrazosulfuron ethyl | 0.07 part |
| Bentonite | 55.0 parts |
| Talc | 34.93 parts |

The above components are mixed uniformly and pulverized, and then a small amount of water is added thereto. The mixture was stirred, mixed and kneaded, and granulated by an extrusion type granulator, followed by drying, to prepare a granule.

Formulation Example 14

Granule

| | |
|---|---|
| Compound A-73 of the present invention | 10.0 part |
| Bensulfuron methyl | 0.25 part |
| Bentonite | 55 parts |
| Talc | 34.75 parts |

The above components are mixed uniformly and pulverized, and then a small amount of water is added thereto. The mixture was stirred, mixed and kneaded, and granulated by an extrusion type granulator, followed by drying, to prepare a granule.

Formulation Example 15

Granule

| | |
|---|---|
| Compound A-73 of the present invention | 10.0 part |
| Pyrazolate | 6 parts |
| Bentonite | 55 parts |
| Talc | 29 parts |

The above components are mixed uniformly and pulverized, and then a small amount of water is added thereto. The mixture was stirred, mixed and kneaded, and granulated by an extrusion type granulator, followed by drying, to prepare a granule.

When the above wettable powder, emulsion, flowable agent or granular wettable powder is used, it is diluted to 50 to 1000-fold with water and so sprayed that its active ingredient is 1 to 10,000 ppm or its active ingredient per hectare (ha) is 0.0001 to 10 kg.

Next, usefulness of the compound of the present invention as a herbicide is described in detail by referring to the following Test examples.

Test Example 1

Test of herbicidal effects by soil treatment

Plastic boxes each having a length of 15 cm, a width of 22 cm and a depth of 6 cm were packed with sterilized diluvial soil, planted with barnyardgrass, crabgrass, foxtail, corn, rice and soy bean randomly and covered with about 1.5 cm of soil. Then, chemical solutions were uniformly sprayed on the soil surfaces by small sprays so that the amounts of the active ingredients became specific ratios. The chemical solutions for spraying were used by diluting preparations suitably prepared according to Formulation examples described above, etc. with water and sprayed on the whole surfaces. Four weeks after spraying the chemical solutions, herbicidal effects on the crops and various weeds were examined according to a judgement standard described below.

The results are shown in Table 4.

Some of the compounds of the present invention have selectivities to certain kinds of crops.

Judgement standard

5: Completely killed or 90% or more of control
4: 70 to 90% of control
3: 40 to 70% of control
2: 20 to 40% of control
1: 5 to 20% of control
0: 5% or less of control The degree of control was determined by observation with naked eyes.

Test Example 2

Test of herbicidal effects by treatment before weeds are grown under submerging condition Wagner pots each having an area of 1/5000 are were packed with alluvial soil and water was poured into the pots to make a submerging condition of a water depth being 4 cm. After seeds of barnyardgrass were sowed in the above pots, seedlings of rice at 2.5 leaf stage were transplanted. The pots were placed in a greenhouse at 25° to 30° C. and the plants were grown. One day after sowing, diluted solutions of the chemicals were subjected to dropwise treatment to the water surfaces by measuring pipettes so that predetermined doses were used. Three weeks after dropwise treatment with the chemical solution, herbicidal effects on rice and barnyardgrass were examined according to the judgement standard of Test example 1. The results are shown in Table 5.

Test Example 3

Test of herbicidal effects by treatment during weeds are grown under submerging condition Wagner pots each having an area of 1/5000 are were packed with alluvial soil and water was poured into the pots to make a submerging condition of a water depth being 4 cm. After seeds of barnyardgrass were sowed in the above pots, seedlings of rice at 2.5 leaf stage were transplanted. The pots were placed in a greenhouse at 25° to 30° C. and the plants were grown. When barnyardgrass came up to 2 leaf stage and rice came up to 4 leaf stage, diluted solutions of the chemicals were subjected to dropwise treatment to the water surfaces by measuring pipettes so that predetermined doses were used. Three weeks after dropwise treatment with the chemicals, herbicidal effects on rice and barnyardgrass were examined according to the judgement standard of Test example 1. The results are shown in Table 6.

Test Example 4

Test of growth control effect on lawn

Plastic pots each having a diameter of 12 cm were packed with-sterilized diluvial soil, and seeds of bent grass and Bermuda grass were sowed therein. 14 days after sowing, preparations suitably prepared according to Formulation examples described above, etc. were so diluted with water to have predetermined concentrations, and 5 ml of each solution was uniformly sprayed on whole stem and leaf portions by using a small spray. 14 days after treatment, lengths of the plants were measured.

The results are shown in Table 7. A figure in the table shows a ratio (%) of the length of the plant to that of the untreated one.

Some of the compounds of the present invention exhibited growth control effects, and no chemical damage was observed.

Test Example 5

Test of herbicidal effects by mixing with pyrazosulfuron ethyl under submerging condition Wagner pots each having an area of 1/5000 are were packed with alluvial soil and water was poured into the pots to make a submerging condition of a water depth being 4 cm. Thereafter, seeds of barnyardgrass, bulrush, monochoria and toothcup were sowed, and tubers of arrowhead and flatstage and seedlings of rice at 2.5 leaf stage were planted. The pots were placed in a greenhouse at 25° to 30° C. and the plants were grown. When barnyardgrass, monochoria, toothcup, bulrush, arrowhead and flatstage came up to 1 to 2 leaf stage, diluted solutions of the chemicals were subjected to dropwise treatment to the water surfaces by measuring pipettes so that predetermined doses were used. Three weeks after treatment with the chemicals, herbicidal effects were examined according to the judgement standard of Test example 1. The results are shown in Table 8.

Marks in the respective tables have the following meanings.

N (barnyardgrass), M (crabgrass), E (foxtail), T (corn), R (rice) and S (soy bean).

TABLE 4

| Compound No. | Dosage (kg/ha) | N | M | E | T | R | S |
| --- | --- | --- | --- | --- | --- | --- | --- |
| A-1 | 2.5 | 5 | 5 | 5 | 0 | 0 | 0 |
| A-5 | 2.5 | 5 | 5 | 5 | 0 | 0 | 0 |
| A-6 | 2.5 | 5 | 5 | 5 | 0 | 0 | 0 |
| A-8 | 2.5 | 5 | 5 | 5 | 0 | 0 | 0 |
| A-10 | 2.5 | 5 | 5 | 5 | 0 | 0 | 0 |
| A-11 | 2.5 | 5 | 5 | 5 | 0 | 0 | 0 |
| A-18 | 2.5 | 5 | 5 | 5 | 0 | 0 | 0 |
| A-19 | 2.5 | 5 | 5 | 5 | 0 | 0 | 0 |
| A-20 | 2.5 | 5 | 5 | 5 | 0 | 0 | 0 |
| A-24 | 2.5 | 5 | 5 | 5 | 0 | 0 | 0 |
| A-27 | 2.5 | 5 | 5 | 5 | 0 | 0 | 0 |
| A-28 | 2.5 | 5 | 5 | 5 | 0 | 0 | 0 |
| A-29 | 2.5 | 5 | 5 | 5 | 0 | 0 | 0 |
| A-30 | 2.5 | 5 | 5 | 5 | 0 | 0 | 0 |
| A-31 | 2.5 | 5 | 5 | 5 | 0 | 0 | 0 |
| A-32 | 2.5 | 5 | 5 | 5 | 0 | 0 | 0 |
| A-35 | 2.5 | 5 | 5 | 5 | 0 | 0 | 0 |
| A-37 | 2.5 | 5 | 5 | 5 | 0 | 0 | 0 |
| A-40 | 2.5 | 5 | 5 | 5 | 0 | 0 | 0 |
| A-46 | 2.5 | 5 | 5 | 5 | 0 | 0 | 0 |
| A-51 | 2.5 | 5 | 5 | 5 | 0 | 0 | 0 |
| A-52 | 2.5 | 5 | 5 | 5 | 0 | 0 | 0 |
| A-56 | 2.5 | 5 | 5 | 5 | 0 | 0 | 0 |
| A-67 | 2.5 | 5 | 5 | 5 | 0 | 0 | 0 |
| A-72 | 2.5 | 5 | 5 | 5 | 0 | 0 | 0 |
| A-73 | 2.5 | 5 | 5 | 5 | 0 | 0 | 0 |
| A-76 | 2.5 | 5 | 5 | 5 | 0 | 0 | 0 |
| A-78 | 2.5 | 5 | 5 | 5 | 0 | 0 | 0 |
| A-83 | 2.5 | 5 | 5 | 5 | 0 | 0 | 0 |
| A-88 | 2.5 | 5 | 5 | 5 | 0 | 0 | 0 |
| A-91 | 2.5 | 5 | 5 | 5 | 0 | 0 | 0 |
| A-93 | 2.5 | 5 | 5 | 5 | 0 | 0 | 0 |
| A-94 | 2.5 | 5 | 5 | 5 | 0 | 0 | 0 |
| A-95 | 2.5 | 5 | 5 | 5 | 0 | 0 | 0 |
| A-96 | 2.5 | 5 | 5 | 5 | 0 | 0 | 0 |
| A-98 | 2.5 | 5 | 5 | 5 | 0 | 0 | 0 |
| A-100 | 2.5 | 5 | 5 | 5 | 0 | 0 | 0 |
| A-101 | 2.5 | 5 | 5 | 5 | 0 | 0 | 0 |
| A-102 | 2.5 | 5 | 5 | 5 | 0 | 0 | 0 |
| A-105 | 2.5 | 5 | 5 | 5 | 0 | 0 | 0 |
| A-106 | 2.5 | 5 | 5 | 5 | 0 | 0 | 0 |
| A-111 | 2.5 | 5 | 5 | 5 | 0 | 0 | 0 |
| A-119 | 2.5 | 5 | 5 | 5 | 0 | 0 | 0 |
| A-121 | 2.5 | 5 | 5 | 5 | 0 | 0 | 0 |
| A-124 | 2.5 | 5 | 5 | 5 | 0 | 0 | 0 |
| A-125 | 2.5 | 5 | 5 | 5 | 0 | 0 | 0 |
| A-126 | 2.5 | 5 | 5 | 5 | 0 | 0 | 0 |
| A-130 | 2.5 | 5 | 5 | 5 | 0 | 0 | 0 |
| A-131 | 2.5 | 5 | 5 | 5 | 0 | 0 | 0 |
| A-133 | 2.5 | 5 | 5 | 5 | 0 | 0 | 0 |
| A-135 | 2.5 | 5 | 5 | 5 | 0 | 0 | 0 |

TABLE 4-continued

| Compound No. | Dosage (kg/ha) | N | M | E | T | R | S |
| --- | --- | --- | --- | --- | --- | --- | --- |
| A-137 | 2.5 | 5 | 5 | 5 | 0 | 0 | 0 |
| A-145 | 2.5 | 5 | 5 | 5 | 0 | 0 | 0 |
| A-149 | 2.5 | 5 | 5 | 5 | 0 | 0 | 0 |
| A-156 | 2.5 | 5 | 5 | 5 | 0 | 0 | 0 |
| A-160 | 2.5 | 5 | 5 | 5 | 0 | 0 | 0 |
| A-164 | 2.5 | 5 | 5 | 5 | 0 | 0 | 0 |
| A-168 | 2.5 | 5 | 5 | 5 | 0 | 0 | 0 |
| A-169 | 2.5 | 5 | 5 | 5 | 0 | 0 | 0 |
| A-174 | 2.5 | 5 | 5 | 5 | 0 | 0 | 0 |
| A-177 | 2.5 | 5 | 5 | 5 | 0 | 0 | 0 |
| A-180 | 2.5 | 5 | 5 | 5 | 0 | 0 | 0 |
| A-181 | 2.5 | 5 | 5 | 5 | 0 | 0 | 0 |
| A-184 | 2.5 | 5 | 5 | 5 | 0 | 0 | 0 |
| A-185 | 2.5 | 5 | 5 | 5 | 0 | 0 | 0 |
| B-1 | 2.5 | 5 | 5 | 5 | 0 | 0 | 0 |
| B-5 | 2.5 | 5 | 5 | 5 | 0 | 0 | 0 |
| B-6 | 2.5 | 5 | 5 | 5 | 0 | 0 | 0 |
| B-7 | 2.5 | 5 | 5 | 5 | 0 | 0 | 0 |
| B-8 | 2.5 | 5 | 5 | 5 | 0 | 0 | 0 |
| B-21 | 2.5 | 5 | 5 | 5 | 0 | 0 | 0 |
| B-23 | 2.5 | 5 | 5 | 5 | 0 | 0 | 0 |
| B-26 | 2.5 | 5 | 5 | 5 | 0 | 0 | 0 |
| B-28 | 2.5 | 5 | 5 | 5 | 0 | 0 | 0 |
| B-32 | 2.5 | 5 | 5 | 5 | 0 | 0 | 0 |
| B-33 | 2.5 | 5 | 5 | 5 | 0 | 0 | 0 |
| B-37 | 2.5 | 5 | 5 | 5. | 0 | 0 | 0 |
| B-40 | 2.5 | 5 | 5 | 5 | 0 | 0 | 0 |
| B-41 | 2.5 | 5 | 5 | 5 | 0 | 0 | 0 |

TABLE 5

| Compound No. | Dosage (g/a) | Barnyardgrass | Transplanted rice |
| --- | --- | --- | --- |
| A-1 | 10 | 5 | 0 |
| A-8 | 10 | 5 | 0 |
| A-18 | 10 | 5 | 0 |
| A-19 | 10 | 5 | 0 |
| A-20 | 10 | 5 | 0 |
| A-24 | 10 | 5. | 0 |
| A-28 | 10 | 5 | 0 |
| A-29 | 10 | 5 | 0 |
| A-30 | 10 | 5 | 0 |
| A-31 | 10 | 5 | 0 |
| A-32 | 10 | 5 | 0 |
| A-33 | 10 | 5 | 0 |
| A-35 | 10 | 5 | 0 |
| A-37 | 10 | 5 | 0 |
| A-40 | 10 | 5 | 0 |
| A-43 | 10 | 5 | 0 |
| A-51 | 10 | 5 | 0 |
| A-56 | 10 | 5 | 0 |
| A-66 | 10 | 5 | 0 |
| A-67 | 10 | 5 | 0 |
| A-68 | 10 | 5 | 0 |
| A-69 | 10 | 5 | 0 |
| A-70 | 10 | 5 | 0 |
| A-71 | 10 | 5 | 0 |
| A-72 | 10 | 5 | 0 |
| A-73 | 10 | 5 | 0 |
| A-74 | 10 | 5 | 0 |
| A-76 | 10 | 5 | 0 |
| A-78 | 10 | 5 | 0 |
| A-83 | 10 | 5 | 0 |
| A-85 | 10 | 5 | 0 |
| A-88 | 10 | 5 | 0 |
| A-91 | 10 | 5 | 0 |
| A-92 | 10 | 5 | 0 |
| A-93 | 10 | 5 | 0 |
| A-94 | 10 | 5 | 0 |
| A-95 | 10 | 5 | 0 |
| A-96 | 10 | 5 | 0 |
| A-98 | 10 | 5 | 0 |

TABLE 5-continued

| Compound No. | Dosage (g/a) | Barnyard-grass | Transplanted rice |
|---|---|---|---|
| A-100 | 10 | 5 | 0 |
| A-101 | 10 | 5 | 0 |
| A-102 | 10 | 5 | 0 |
| A-103 | 10 | 5 | 0 |
| A-104 | 10 | 5 | 0 |
| A-105 | 10 | 5 | 0 |
| A-106 | 10 | 5 | 0 |
| A-111 | 10 | 5 | 0 |
| A-112 | 10 | 5 | 0 |
| A-113 | 10 | 5 | 0 |
| A-119 | 10 | 5 | 0 |
| A-120 | 10 | 5 | 0 |
| A-121 | 10 | 5 | 0 |
| A-123 | 10 | 5 | 0 |
| A-124 | 10 | 5 | 0 |
| A-125 | 10 | 5 | 0 |
| A-126 | 10 | 5 | 0 |
| A-130 | 10 | 5 | 0 |
| A-131 | 10 | 5 | 0 |
| A-132 | 10 | 5 | 0 |
| A-133 | 10 | 5 | 0 |
| A-135 | 10 | 5 | 0 |
| A-137 | 10 | 5 | 0 |
| A-141 | 10 | 5 | 0 |
| A-142 | 10 | 5 | 0 |
| A-143 | 10 | 5 | 0 |
| A-149 | 10 | 5 | 0 |
| A-151 | 10 | 5 | 0 |
| A-156 | 10 | 5 | 0 |
| A-159 | 10 | 5 | 0 |
| A-160 | 10 | 5 | 0 |
| A-161 | 10 | 5 | 0 |
| A-162 | 10 | 5 | 0 |
| A-163 | 10 | 5 | 0 |
| A-164 | 10 | 5 | 0 |
| A-165 | 10 | 5 | 0 |
| A-167 | 10 | 5 | 0 |
| A-168 | 10 | 5 | 0 |
| A-169 | 10 | 5 | 0 |
| A-171 | 10 | 5 | 0 |
| A-174 | 10 | 5 | 0 |
| A-177 | 10 | 5 | 0 |
| A-178 | 10 | 5 | 0 |
| A-180 | 10 | 5 | 0 |
| A-181 | 10 | 5 | 0 |
| A-184 | 10 | 5 | 0 |
| A-185 | 10 | 5 | 0 |
| A-191 | 10 | 5 | 0 |
| B-1 | 10 | 5 | 0 |
| B-4 | 10 | 5 | 0 |
| B-5 | 10 | 5 | 0 |
| B-6 | 10 | 5 | 0 |
| B-7 | 10 | 5 | 0 |
| B-8 | 10 | 5 | 0 |
| B-19 | 10 | 5 | 0 |
| B-21 | 10 | 5 | 0 |
| B-23 | 10 | 5 | 0 |
| B-24 | 10 | 5 | 0 |
| B-26 | 10 | 5 | 0 |
| B-27 | 10 | 5 | 0 |
| B-28 | 10 | 5 | 0 |
| B-31 | 10 | 5 | 0 |
| B-32 | 10 | 5 | 0 |
| B-33 | 10 | 5 | 0 |
| B-34 | 10 | 5 | 0 |
| B-35 | 10 | 5 | 0 |
| B-36 | 10 | 5 | 0 |
| B-37 | 10 | 5 | 0 |
| B-40 | 10 | 5 | 0 |
| B-41 | 10 | 5 | 0 |

TABLE 6

| Compound No. | Dosage (g/a) | Barnyard-grass | Transplanted rice |
|---|---|---|---|
| A-1 | 40 | 5 | 0 |
| A-18 | 40 | 5 | 0 |
| A-19 | 40 | 5 | 0 |
| A-20 | 40 | 5 | 0 |
| A-24 | 40 | 5 | 0 |
| A-28 | 40 | 5 | 0 |
| A-29 | 40 | 5 | 0 |
| A-30 | 40 | 5 | 0 |
| A-31 | 40 | 5 | 0 |
| A-32 | 40 | 5 | 0 |
| A-33 | 40 | 5 | 0 |
| A-35 | 40 | 5 | 0 |
| A-37 | 40 | 5 | 0 |
| A-40 | 40 | 5 | 0 |
| A-43 | 40 | 5 | 0 |
| A-51 | 40 | 5 | 0 |
| A-56 | 40 | 5 | 0 |
| A-66 | 40 | 5 | 0 |
| A-67 | 40 | 5 | 0 |
| A-68 | 40 | 5 | 0 |
| A-69 | 40 | 5 | 0 |
| A-70 | 40 | 5 | 0 |
| A-71 | 40 | 5 | 0 |
| A-72 | 40 | 5 | 0 |
| A-73 | 40 | 5 | 0 |
| A-74 | 40 | 5 | 0 |
| A-76 | 40 | 5 | 0 |
| A-78 | 40 | 5 | 0 |
| A-83 | 40 | 5 | 0 |
| A-85 | 40 | 5 | 0 |
| A-88 | 40 | 5 | 0 |
| A-91 | 40 | 5 | 0 |
| A-92 | 40 | 5 | 0 |
| A-93 | 40 | 5 | 0 |
| A-94 | 40 | 5 | 0 |
| A-95 | 40 | 5 | 0 |
| A-96 | 40 | 5 | 0 |
| A-98 | 40 | 5 | 0 |
| A-100 | 40 | 5 | 0 |
| A-101 | 40 | 5 | 0 |
| A-102 | 40 | 5 | 0 |
| A-103 | 40 | 5 | 0 |
| A-104 | 40 | 5 | 0 |
| A-105 | 40 | 5 | 0 |
| A-106 | 40 | 5 | 0 |
| A-111 | 40 | 5 | 0 |
| A-112 | 40 | 5 | 0 |
| A-113 | 40 | 5 | 0 |
| A-119 | 40 | 5 | 0 |
| A-120 | 40 | 5 | 0 |
| A-121 | 40 | 5 | 0 |
| A-123 | 40 | 5 | 0 |
| A-124 | 40 | 5 | 0 |
| A-125 | 40 | 5 | 0 |
| A-126 | 40 | 5 | 0 |
| A-130 | 40 | 5 | 0 |
| A-131 | 40 | 5 | 0 |
| A-132 | 40 | 5 | 0 |
| A-133 | 40 | 5 | 0 |
| A-135 | 40 | 5 | 0 |
| A-137 | 40 | 5 | 0 |
| A-141 | 40 | 5 | 0 |
| A-142 | 40 | 5 | 0 |
| A-149 | 40 | 5 | 0 |
| A-151 | 40 | 5 | 0 |
| A-156 | 40 | 5 | 0 |
| A-159 | 40 | 5 | 0 |
| A-160 | 40 | 5 | 0 |
| A-161 | 40 | 5 | 0 |
| A-162 | 40 | 5 | 0 |
| A-163 | 40 | 5 | 0 |
| A-164 | 40 | 5 | 0 |
| A-165 | 40 | 5 | 0 |
| A-167 | 40 | 5 | 0 |
| A-168 | 40 | 5 | 0 |
| A-169 | 40 | 5 | 0 |

TABLE 6-continued

| Compound No. | Dosage (g/a) | Barnyard-grass | Transplanted rice |
|---|---|---|---|
| A-171 | 40 | 5 | 0 |
| A-174 | 40 | 5 | 0 |
| A-177 | 40 | 5 | 0 |
| A-178 | 40 | 5 | 0 |
| A-180 | 40 | 5 | 0 |
| A-181 | 40 | 5 | 0 |
| A-185 | 40 | 5 | 0 |
| B-7 | 40 | 5 | 0 |
| B-8 | 40 | 5 | 0 |
| B-23 | 40 | 5 | 0 |
| B-26 | 40 | 5 | 0 |
| B-28 | 40 | 5 | 0 |
| B-32 | 40 | 5 | 0 |
| B-37 | 40 | 5 | 0 |
| B-40 | 40 | 5 | 0 |
| B-41 | 40 | 5 | 0 |

TABLE 7

| Compound No. | Chemical concentration (ppm) | Bent grass | Bermuda grass |
|---|---|---|---|
| A-51 | 300 | 85 | 83 |
|  | 1000 | 67 | 65 |
| A-61 | 1000 | 93 | 85 |
| A-72 | 1000 | 84 | 85 |

TABLE 8

| Compound No. | Dosage g/a | Barnyard-grass | Bulrush | Mono-choria | Tooth-cup | Arrow-head | Flat-stage | Transplant-ed rice |
|---|---|---|---|---|---|---|---|---|
| A-73 | 40 | 5 | 0 | 0 | 0 | 0 | 0 | 0 |
| P | 0.21 | 3 | 5 | 5 | 5 | 5 | 5 | 0 |
| A-73 + P | 40 + 0.21 | 5 | 5 | 5 | 5 | 5 | 5 | 0 |

P: Pyrazosulfuron ethyl

We claim:

1. A 2-arylaminopyrimidinone derivative represented by the formula (1):

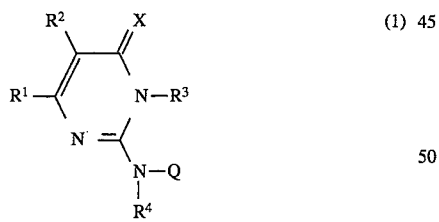

wherein $R^1$ represents a $C_1$ to $C_4$ haloalkyl group, a $C_2$ to $C_6$ alkyl group, a $C_3$ to $C_7$ cycloalkyl group, a $C_2$ to $C_6$ alkenyl group, a $C_1$ to $C_6$ haloalkyloxy group, a $C_1$ to $C_6$ alkoxy group, a $C_3$ to $C_7$ cycloalkyloxy group, a $C_3$ to $C_6$ alkenyloxy group, a $C_1$ to $C_6$ haloalkylthio group, a $C_1$ to $C_6$ alkylthio group, a $C_3$ to $C_7$ cycloalkylthio group, a $C_3$ to $C_6$ alkenylthio group, a $C_1$ to $C_6$ haloalkylsulfinyl group, a $C_1$ to $C_6$ alkylsulfinyl group, a $C_3$ to $C_7$ cycloalkylsulfinyl group, a $C_3$ to $C_6$ alkenylsulfinyl group, a $C_1$ to $C_6$ haloalkylsulfonyl group, a $C_1$ to $C_6$ alkylsulfonyl group, a $C_3$ to $C_7$ cycloalkylsulfonyl group, a $C_3$ to $C_6$ alkenylsulfonyl group, a $C_1$ to $C_4$ alkoxy ($C_1$ to $C_4$) alkylene group, a $C_1$ to $C_4$ alkylthio ($C_1$ to $C_4$) alkylene group, a $C_1$ to $C_4$ alkoxy ($C_1$ to $C_4$) alkoxy group, a $C_1$ to $C_4$ alkylsulfinyl ($C_1$ to $C_4$) alkylene group, a $C_1$ to $C_4$ alkylsulfonyl ($C_1$ to $C_4$) alkylene group, a $C_1$ to $C_4$ alkylamino ($C_1$ to $C_4$) alkylene group, a $C_3$ to $C_7$ cycloalkyl ($C_1$ to $C_4$) alkylene group, a dimethylamino ($C_1$ to $C_4$) alkylene group, a diethylamino ($C_1$ to $C_4$) alkylene group or a halogen atom, $R^2$ represents a hydrogen atom, a halogen atom, a $C_1$ to $C_4$ alkyl group, a $C_1$ to $C_4$ haloalkyl group or a nitro group, $R^3$ represents a $C_1$ to $C_6$ alkyl group, a $C_3$ to $C_6$ alkenyl group, a $C_3$ to $C_6$ alkynyl group, a $C_3$ to $C_7$ cycloalkyl group or an amino group, $R^4$ represents a hydrogen atom, a $C_1$ to $C_6$ alkyl group, a $C_2$ to $C_6$ alkenyl group, a $C_3$ to $C_6$ alkynyl group, a $C_1$ to $C_6$ haloalkyl group, a $C_1$ to $C_4$ alkoxy ($C_1$ to $C_4$) alkylene group, a hydroxycarbonyl ($C_1$ to $C_4$) alkylene group, a $C_1$ to $C_4$ alkoxycarbonyl ($C_1$ to $C_4$) alkylene group, a formyl group, a $C_1$ to $C_4$ alkylcarbonyl group, a $C_1$ to $C_4$ alkoxycarbonyl group, an aminocarbonyl group, a $C_1$ to $C_6$ alkylaminocarbonyl group, a $C_1$ to $C_6$ alkylsulfonyl group, a dimethylaminocarbonyl group, a diethylaminocarbonyl group or a benzyl group

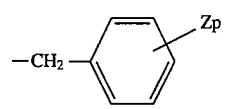

wherein Z represents a halogen atom, a $C_1$ to $C_4$ alkyl group, a $C_1$ to $C_4$ haloalkyl group, a $C_1$ to $C_4$ alkoxy group, a $C_1$ to $C_4$ haloalkoxy group, a $C_1$ to $C_4$ alkoxycarbonyl group, a carboxy group, a cyano group or a nitro group, p represents an integer of 0 to 3, provided that when p is 2 or 3, Zs may be the same or different, X represents an oxygen atom or a sulfur atom and Q represents

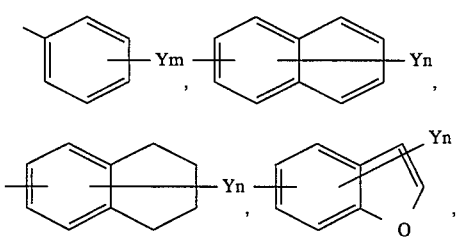

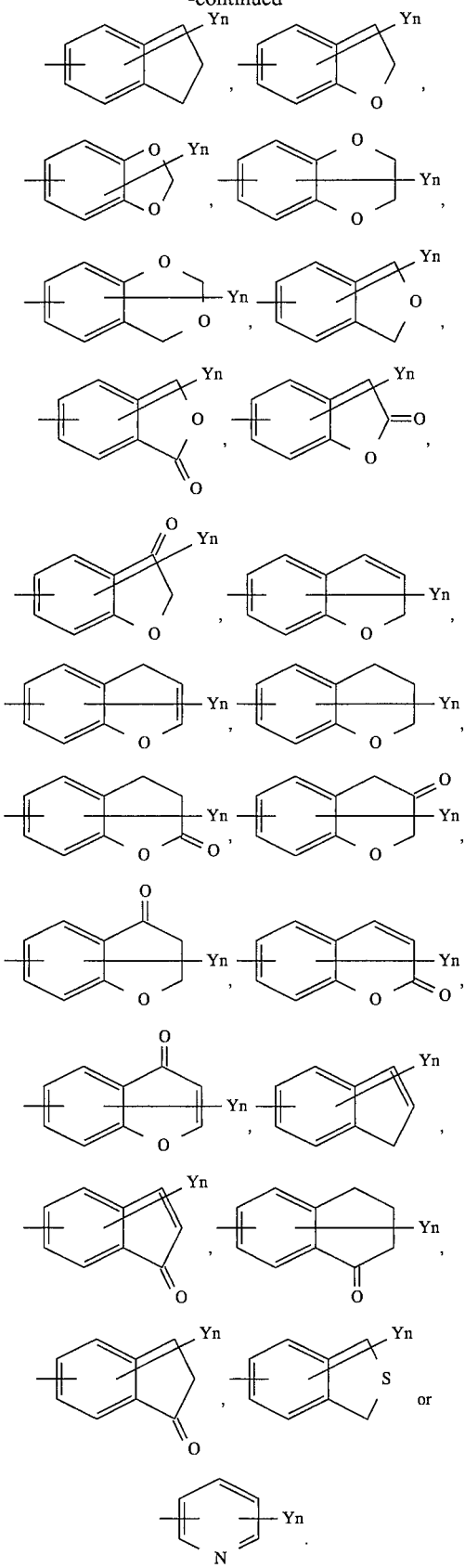

wherein Y represents a halogen atom, a $C_1$ to $C_4$ alkyl group, a $C_1$ to $C_4$ alkoxy group, a $C_1$ to $C_4$ alkoxy ($C_1$ to $C_4$) alkylene group, a $C_1$ to $C_4$ haloalkyl group, a $C_1$ to $C_4$ haloalkoxy group, a $C_1$ to $C_4$ alkylthio group, a $C_1$ to $C_4$ alkylsulfinyl group, a $C_1$ to $C_4$ alkylsulfonyl group, a $C_1$ to $C_4$ alkylcarbonyl group, a $C_1$ to $C_4$ alkoxycarbonyl group, a $C_3$ to $C_6$ alkenyl group, a $C_3$ to $C_6$ alkenyloxy group, a $C_3$ to $C_6$ alkynyloxy group, a $C_1$ to $C_4$ alkylcarbonyloxy group, a $C_1$ to $C_4$ alkoxy ($C_1$ to $C_4$) alkoxy group, a hydroxycarbonyl ($C_1$ to $C_4$) alkylene group, a $C_1$ to $C_4$ alkoxycarbonyl ($C_1$ to $C_4$) alkylene group, a hydroxycarbonyl ($C_1$ to $C_4$) alkoxy group, a $C_1$ to $C_4$ alkoxycarbonyl ($C_1$ to $C_4$) alkoxy group, a $C_1$ to $C_4$ alkylamino group, a dimethylamino group, a diethylamino group, a $C_1$ to $C_4$ alkylcarbonylamino group, a $C_1$ to $C_4$ alkylsulfonylamino group, a thiol group, a cyano group, a carboxy group, an amino group or a hydroxy group, m represents an integer of 1 to 5, n represents an integer of 0 to 3, provided when m is an integer of 2 to 5 or when n is 2 or 3, Ys may be the same or different.

2. The compound according to claim 1, wherein $R^1$ is a $C_1$ to $C_4$ haloalkyl group.

3. The compound according to claim 2, wherein $R^1$ is a trifluoromethyl group, a difluoromethyl group, a chlorodifluoromethyl group or a pentafluoroethyl group.

4. The compound according to claim 1, wherein $R^1$ is a $C_2$ to $C_6$ alkyl group, a $C_3$ to $C_7$ cycloalkyl group, a $C_2$ to $C_6$ alkenyl group, a $C_1$ to $C_4$ alkoxy ($C_1$ to $C_4$) alkyl group or a halogen atom.

5. The compound according to claim 4, wherein $R^1$ is an ethyl group, a n-propyl group, an i-propyl group, a n-butyl group, an i-butyl group, a s-butyl group, a t-butyl group, a 2,2-dimethylpropyl group, a 1,1-dimethylpropyl group, a cyclopropyl group, a 1-propenyl group, a 2-propenyl group, a methoxymethyl group, an ethoxymethyl group, an i-propoxymethyl group, a 2-methoxyethyl group or a 2-ethoxyethyl group.

6. The compound according to claim 1, wherein $R^2$ is a hydrogen atom or a methyl group.

7. The compound according to claim 1, wherein $R^3$ is a $C_1$ to $C_6$ alkyl group or an amino group.

8. The compound according to claim 7, wherein $R^3$ is a methyl group or an ethyl group.

9. The compound according to claim 1, wherein $R^4$ is a hydrogen atom.

10. The compound according to claim 1, wherein $R^4$ is a $C_1$ to $C_6$ alkyl group.

11. The compound according to claim 10, wherein $R^4$ is a methyl group or an ethyl group.

12. The compound according to claim 1, wherein $R^4$ is a benzyl group, a o-chlorobenzyl group, a m-chlorobenzyl group, a p-chlorobenzyl group, a o-methylbenzyl group, a m-methylbenzyl group, a p-methylbenzyl group or a m-trifluoromethylbenzyl group.

13. The compound according to claim 1, wherein $R^4$ is an ethenyl group, a 2-propenyl group, a 2-methyl-2-propenyl group, a 2-butenyl group, a 2-propynyl group, a 2-butynyl group, a difluoromethyl group, a chloromethyl group, a 2-chloroethyl group, a methoxymethyl group, an ethoxymethyl group, a 2-methoxyethyl group, a 2-ethoxyethyl group, a hydroxycarbonylmethyl group, a 1-hydroxycarbonylethyl group, a methoxycarbonylmethyl group, an ethoxycarbonylmethyl group, a 1-methoxycarbonylethyl group, a 1-ethoxycarbonylethyl group, a formyl group, an acetyl group, an ethylcarbonyl group, a n-propylcarbonyl group, an i-propylcarbonyl group, a t-butylcarbonyl group, a methoxycarbonyl group, an ethoxycarbonyl group, a n-propylcarbonyl group, an i-propylcarbonyl group, an aminocarbonyl group, a methylaminocarbonyl group, an ethylaminocarbonyl group, a methylsulfonyl group, a dimethylaminocarbonyl group or a diethylaminocarbonyl group.

14. The compound according to claim 1, wherein X is an oxygen atom.

15. The compound according to claim 1, wherein Q represents

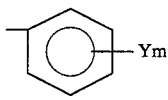

(wherein Y and m have the same meanings as described above).

16. The compound according to claim 1, wherein Q represents

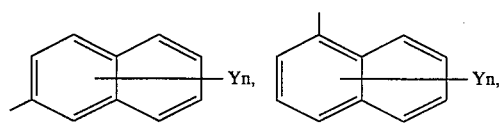

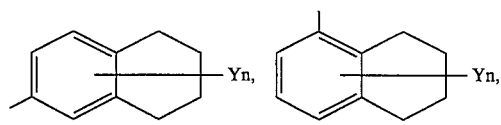

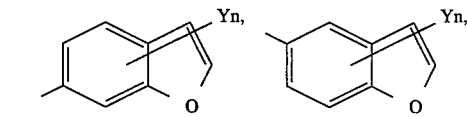

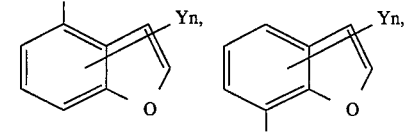

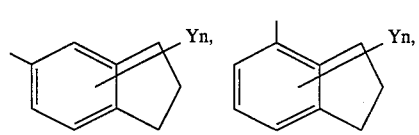

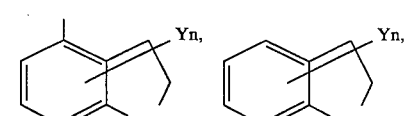

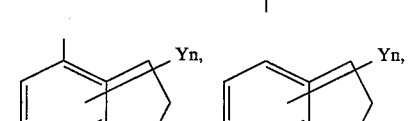

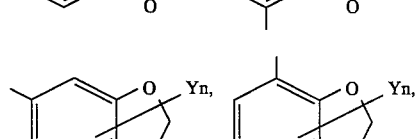

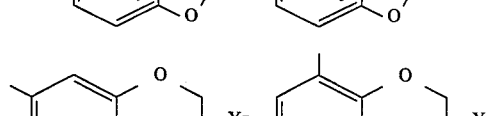

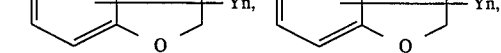

-continued

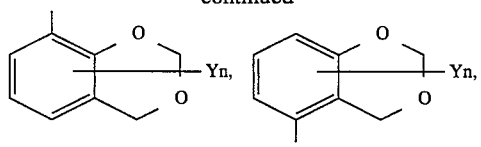

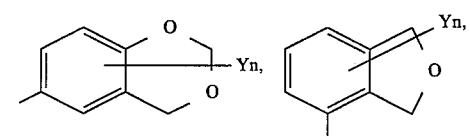

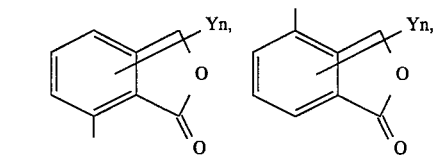

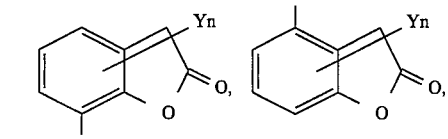

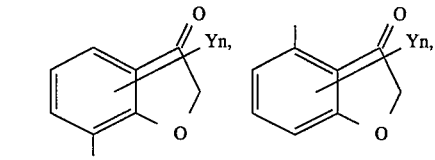

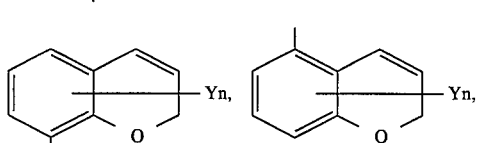

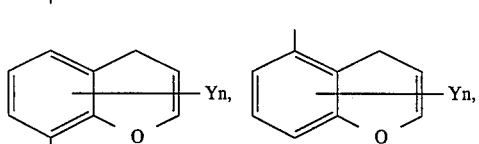

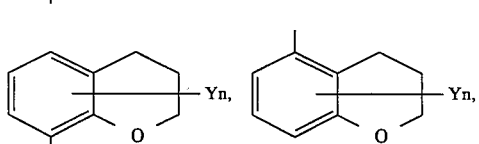

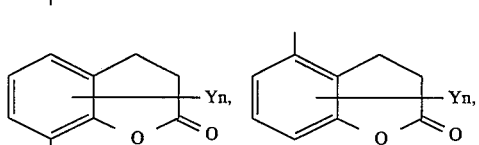

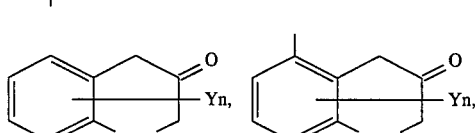

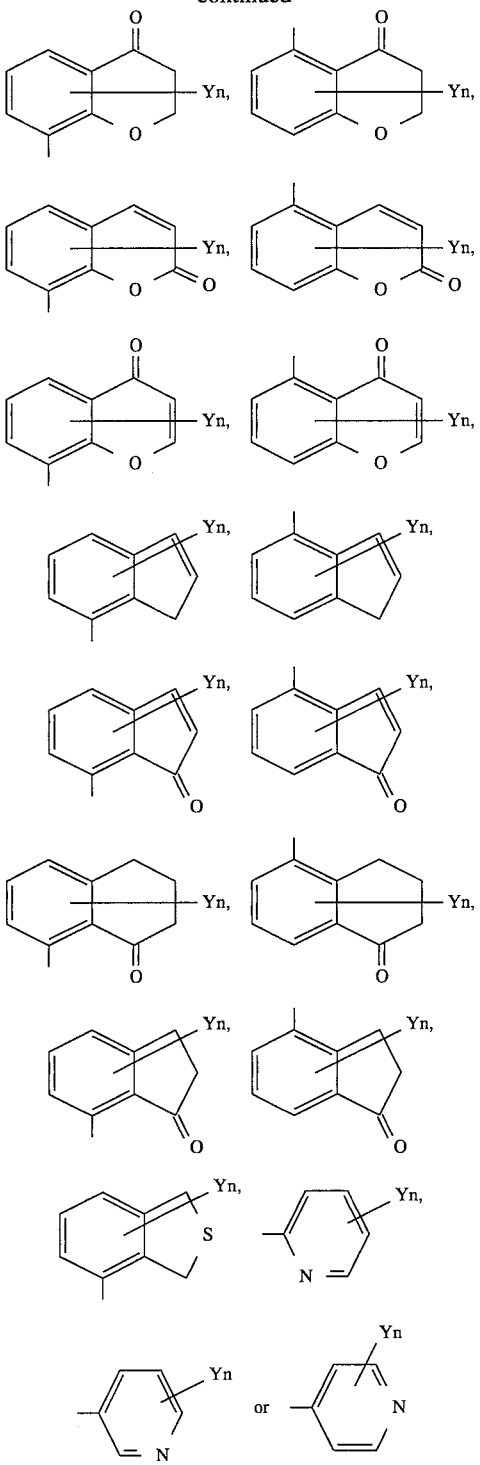

wherein Y and n have the same meanings as described above.

17. The compound according to claim 1 wherein the substituent Y is a group selected from the group consisting of a fluorine atom, a chlorine atom, a bromine atom, an iodine atom, a methyl group, an ethyl group, a n-propyl group, an iso-propyl group, a n-butyl group, an iso-butyl group, a sec-butyl group, a tert-butyl group, a methoxy group, an ethoxy group, a n-propoxy group, an iso-propoxy group, a n-butoxy group, an iso-butoxy group, a sec-butoxy group, a tert-butoxy group, a methoxymethyl group, a 2-methoxyethyl group, an ethoxymethyl group, a 2-ethoxyethyl group, a fluoromethyl group, a chloromethyl group, a bromomethyl group, a trichloromethyl group, a trifluoromethyl group, a 1-chloroethyl group, a 2-chloroethyl group, a 3-chloropropyl group, a trifluoromethoxy group, a difluoromethoxy group, a 2-chloroethoxy group, a 3-chloropropoxy group, a 2-chloro-1-methylethoxy group, a 2,2,2-trifluoroethoxy group, a methylthio group, an ethylthio group, a n-propylthio group, an iso-propylthio group, a n-butylthio group, an iso-butylthio group, a sec-butylthio group, a tert-butylthio group, a methylsulfinyl group, an ethylsulfinyl group, an n-propylsulfinyl group, an iso-propylsulfinyl group, a n-butylsulfinyl group, an iso-butylsulfinyl group, a sec-butylsulfinyl group, a tert-butylsulfinyl group, a methylsulfonyl group, an ethylsulfonyl group, a n-propylsulfonyl group, an iso-propylsulfonyl group, a n-butylsulfonyl group, an iso-butylsulfonyl group, a sec-butylsulfonyl group, an acetyl group, an ethylcarbonyl group, a n-propylcarbonyl group, a methoxycarbonyl group, an ethoxycarbonyl group, a n-propoxycarbonyl group, an iso-propoxycarbonyl group, a n-butoxycarbonyl group, an iso-butoxycarbonyl group, a sec-butoxycarbonyl group, a tert-butoxycarbonyl group, a 2-propenyl group, a 2-propenyloxy group, a 2-methyl, 2-propenyloxy group, a 2-butenyloxy group, a 2-propynyloxy group, a 1-methyl-2-propynyloxy group, an acetoxy group, an ethylcarbonyloxy group, a methoxymethoxy group, an ethoxymethoxy group, an i-propoxymethoxy group, a 2-methoxyethoxy group, a hydroxycarbonylmethyl group, a 1-(hydroxycarbonyl)ethyl group, an methoxycarbonylmethyl group, an ethoxycarbonylmethyl group, a 1-(methoxycarbonyl)ethyl group, a hydroxycarbonylmethoxy group, a 1-(hydroxycarbonyl)ethoxy group, a methoxycarbonylmethoxy group, an ethoxycarbonylmethoxy group, a 1-(methoxycarbonyl)ethoxy group, a methylamino group, an ethylamino group, a n-propylamino group, an i-propylamino group, a n-butylamino group, a dimethylamino group, a diethylamino group, an acetylamino group, a methylsulfonylamino group, an ethylsulfonylamino group, a thiol group, a cyano group, a carboxy group, an amino group and a hydroxy group.

18. The compound according to claim 1 wherein $R^1$ is a trifluoromethyl group, $R^2$ is a hydrogen atom, $R^3$ is a methyl group, $R^4$ is a hydrogen atom or a methyl group and X is an oxygen atom.

19. The compound according to claim 1, wherein said compound is selected from the group consisting of
2-(3-chloro-2,4-difluorophenyl)amino-3-methyl-6-trifluoromethyl- 4(3H)-pyrimidinone,
2-(3-chloro-2-methylphenyl)amino-3-methyl-6-trifluoromethyl- 4(3H)-pyrimidinone,
2-(3-bromo-2-methylphenyl)amino-3-methyl-6-trifluoromethyl- 4(3H)-pyrimidinone,
3-methyl-2-[1-(5,6,7,8-tetrahydronaphthyl)]amino-6-trifluoromethyl- 4(3H)-pyrimidinone,
2-(3-bromo-2,4-dichlorophenyl)amino-3-methyl-6-trifluoromethyl- 4(3H)-pyrimidinone,
2-(2,4-difluoro-3-methylphenyl)amino-3-methyl-6-trifluoromethyl- 4(3H)-pyrimidinone,
3-methyl-2-(1-naphthyl)amino-6-trifluoromethyl-3H-pyrimidine- 4-thion, 2-(2,4-difluoro-3-bromophenyl)amino-3-methyl-6-trifluoromethyl- 4(3H)-pyrimidinone, 2-(3-iodo-2-methylphenyl)amino-3-methyl-6-trifluoromethyl- 4(3H)-pyrimidinone, 2-[N-(3-bromo-2,4-difluorophenyl)-N-methyl]amino-3-methyl- 6-trifluoromethyl-4(3H)-pyrimidinone, 2-[N-(2-fluoro-3-trifluoromethylphenyl)-N-methyl]amino-3-methyl-6-trifluoromethyl-4(3H)-pyrimidinone and 2-[N-(3-chloro-2,4-difluorophenyl)-N-methyl]amino-3-methyl-6-trifluoromethyl-4(3H)-pyrimidinone.

20. A herbicidal composition and a plant growth regulating composition comprising a herbicidally effective amount of the 2-arylaminopyrimidinone derivative according to claim 1.

* * * * *

UNITED STATES PATENT AND TRADEMARK OFFICE
CERTIFICATE OF CORRECTION

PATENT NO. : 5,518,994
DATED : May 21, 1996
INVENTOR(S) : Yasuo KAWAMURA et al.

It is certified that error appears in the above-indentified patent and that said Letters Patent is hereby corrected as shown below:

On title page, item [22], should read as follows:
"Apr. 13, 1993" should read --Apr. 15, 1993--

Signed and Sealed this

Third Day of December, 1996

Attest:

BRUCE LEHMAN

Attesting Officer

Commissioner of Patents and Trademarks